US006706510B2

(12) United States Patent
Webster et al.

(10) Patent No.: US 6,706,510 B2
(45) Date of Patent: Mar. 16, 2004

(54) ISOLATED HUMAN KINASE PROTEINS

(75) Inventors: Marion Webster, San Fransisco, CA (US); Chunhua Yan, Boyds, MD (US); Valentina Di Francesco, Rockville, MD (US); Ellen Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/243,735

(22) Filed: Sep. 16, 2002

(65) Prior Publication Data

US 2003/0022341 A1 Jan. 30, 2003

Related U.S. Application Data

(60) Division of application No. 09/873,404, filed on Jun. 5, 2001, now Pat. No. 6,500,656, which is a continuation-in-part of application No. 09/824,583, filed on Apr. 3, 2001, now abandoned.

(51) Int. Cl.$^7$ .......................... C12N 9/12; C12N 15/00; C12N 5/00; C12N 1/20; C07K 1/00

(52) U.S. Cl. ....................... 435/194; 530/350; 435/325; 435/320.1; 435/252.3; 435/6

(58) Field of Search ............................. 435/194, 320.1, 435/325, 6, 252.3; 530/350

(56) References Cited

U.S. PATENT DOCUMENTS 6,013,455 A 1/2000 Bandman et al. .............. 435/6

OTHER PUBLICATIONS

Results of BLAST search of SEQ ID NO:2 against Derwent (FastAlert and GeneSeqP) and NCBI (pataa) protein patent databases on Sep. 12, 2003.

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

4 Claims, 35 Drawing Sheets

```
   1 CATTGGAGAC CATGGATAAG TACGATGTGA TTAAGGCCAT CGGGCAAGGT
  51 GCCTTCGGGA AAGCATACTT AGCTAAAGGG AAATCAGATA GCAAGCACTG
 101 TGTCATAAAA GAGATCAATT TTGAAAAGAT GCCCATACAA GAAAAAGAAG
 151 CTTCAAAGAA AGAAGTGATT CTTCTGGAAA AGATGAAACA TCCCAACATT
 201 GTAGCCTTCT TCAATTCATT TCAAGAGAAT GGCAGGCTGT TTATTGTAAT
 251 GGAATATTGT GATGGAGGGG ATCTCATGAA AAGGATCAAT AGACAACGGG
 301 GTGTGTTATT TAGTGAAGAT CAGATCCTCG GTTGGTTTGT ACAGATTTCT
 351 CTAGGACTAA AACATATTCA TGACAGGAAG ATATTACACA GGGACATAAA
 401 AGCTCAGAAC ATTTTTCTTA GCAAGAACGG AATGGTGGCA AAGCTTGGGG
 451 ACTTTGGTAT AGCAAGAGTC CTGAATAATT CCATGGAACT TGCTCGAACT
 501 TGTATTGGAA CACCTTACTA CCTGTCCCCA GAGATCTGTC AGAATAAACC
 551 CTACAACAAT AAAACGGATA TTTGGTCTCT TGGCTGTGTC TTATATGAGC
 601 TCTGCACACT TAAACATCCT TTTGAGGGTA ACAACTTACA GCAGCTGGTT
 651 CTGAAGATTT GTCAAGCACA TTTTGCCCCA ATATCTCCGG GGTTTTCTCG
 701 TGAGCTCCAT TCCTTGATAT CTCAGCTCTT TCAAGTATCT CCTCGAGACC
 751 GACCATCCAT AAATTCCATT TTGAAAAGGC CCTTTTTAGA GAATCTTATT
 801 CCCAAATATT TGACTCCTGA GGTCATTCAG GAAGAATTCA GTCACATGCT
 851 TATATGCAGA GCAGGAGCGC CAGCTTCTCG ACATGCTGGG AAGGTGGTCC
 901 AGAAGTGTAA AATACAAAAA GTGAGATTCC GGGGAAAGTG CCCACCAAGA
 951 TCAAGGATAT CTGTGCCAAT TAAAAGGAAT GCTATATTGC ATAGAAATGA
1001 ATGGAGACCA CCAGCTGGAG CCCAGAAGGC CAGATCTATA AAAATGATAG
1051 AAAGACCCAA AATTGCTGCT GTCTGTGGAC ATTATGATTA TTATTATGCT
1101 CAACTTGATA TGCTGAGGAG GAGAGCCCAC AAACCAAGTT ATCACCCTAT
1151 TCCTCAAGAA AATACTGGAG TTGAGGATTA CGGTCAGGAA ACGAGGCATG
1201 GTCCATCCCC AAGTCAATGG CCTGCTGAGT ACCTTCAGAG AAAATTTGAA
1251 GCTCAACAAT ATAAGTTGAA AGTGGAGAAG CAATTGGGTC TTCGTCCATC
1301 TTCTGCCGAG CCAAATTACA ACCAGAGACA AGAGCTAAGA AGTAATGGAG
1351 AAGAGCCTAG ATTCCAGGAG CTGCCATTTA GGAAAAACGA AATGAAGGAA
1401 CAGGAATATT GGAAGCAGTT AGAGGAAATA CGCCAACAGT ACCTCAATGA
1451 CATGAAAGAA ATTAGAAAGA AGATGGGGAG AGAACCAGAG GACATTGAAA
1501 AAGACTTGAA ACAAATGAGG CTTCAGAACA CAAAGGAAAG TAAAAATCCA
1551 GAACAGAAAT ATAAAGCTAA GAAGGGGGTA AAATTTGAAA TTAATTTAGA
1601 CAAATGTATT TCTGATGAAA ACATCCTCCA AGAGGAAGAG GCAATGGATA
1651 TACCAAATGA AACTTTGACC TTTGAGGATG GCATGAAGTT TAAGGAATAT
1701 GAATGTGTAA AGGAGCATGG AGATTATACA GACAAAGCAT TTGAAAAACT
1751 TCACTGCCCA GAAGCAGCAT TTACAGAACT GACTTGGCTC AGTTTCCTCT
1801 TCCTGGAATA CTCTCTGCCT CATTTCCTTC TGGAAAAATC TCCATTCAGC
1851 AGGCATCTTA TTGAGGATCT CCTTTGTGCC AACGACTGCT CACTGAAGGA
1901 CTGGAGTGAG AAGGAAATGG AGCTTAGGAC ATAACCCTAC CACTACATAA
1951 ACAAACTTTG GAGAATCAGG AGAGAGTAAA GCCAAAGGAG GAGAGACAGG
2001 TCATGGGGAG GCACAGGAAT TGGCAGCATC AACTGGAAGA GAAAGGCCAG
2051 ATGAGGGTTT TCCACGCAGA CTGTAGTTGC TGTGGGAAAC AGGAGGCAGT
2101 GGGATGGAGG AGCGCCTCAG ACTCTGCTGC AGATGATGGC AGTGGCCGAC
2151 ATCACCTCCA CCTGCCCCAC GGGGCCTGAC AGTGAGTCTG TGCTTAGTGT
2201 CAGTCGTCAG GAAGGGAAGA CCAAGGACCC GTACAGCCCA GTGCTCATCC
2251 TGATGTGATA GTCTACTTCT CACTATACAC CCTATAGATC TTGTATCAGA
2301 CACTTTCAAA TATGTTGTTT TGATATCTCA AGAAAAAAAA AAAAAAAACA
2351 CTGTCATGCC GTTACGAGCG  (SEQ ID NO:1)
```

FEATURES:

```
5'UTR:         1-11
Start Codon:   12
Stop Codon:    1932
3'UTR:         1935
```

FIGURE 1A

Homologous proteins:
Top 10 BLAST Hits

| | Score | E |
|---|---|---|
| CRA\|18000004898313 /altid=gi\|1709251 /def=sp\|P51954\|NEK1_MOUSE ... | 389 | e-107 |
| CRA\|18000005213056 /altid=gi\|9297022 /def=sp\|Q9R0A5\|NEK3_MOUSE ... | 311 | 2e-83 |
| CRA\|18000005207774 /altid=gi\|6754820 /def=ref\|NP_035978.1\| NIMA... | 311 | 3e-83 |
| CRA\|18000004929662 /altid=gi\|1709253 /def=sp\|P51956\|NEK3_HUMAN ... | 285 | 2e-75 |
| CRA\|108000024647614 /altid=gi\|12729925 /def=ref\|XP_003216.2\| se... | 256 | 1e-66 |
| CRA\|18000005131165 /altid=gi\|2570047 /def=emb\|CAA70436.1\| (Y092... | 254 | 3e-66 |
| CRA\|18000005199482 /altid=gi\|7522642 /def=pir\|\|JC7122 serine (t... | 254 | 3e-66 |
| CRA\|18000005207775 /altid=gi\|6754822 /def=ref\|NP_035979.1\| NIMA... | 254 | 3e-66 |
| CRA\|18000004925928 /altid=gi\|4507277 /def=ref\|NP_003148.1\| seri... | 252 | 1e-65 |
| CRA\|98000043621119 /altid=gi\|12852471 /def=dbj\|BAB29424.1\| (AK0... | 244 | 4e-63 |

BLAST dbEST hits:

| | | |
|---|---|---|
| gi\|12358928 /dataset=dbest /taxon=96... | 252 | 3e-64 |
| gi\|4310159 /dataset=dbest /taxon=9606 ... | 252 | 3e-64 |

EXPRESSION INFORMATION FOR MODULATORY USE:
library source:
From BLAST dbEST hits:
gi|12358928 Lung carcinoma
gi|4310159 Lung carcinoma library source of cDNA clone:
placenta

FIGURE 1B

```
  1 MDKYDVIKAI GQGAFGKAYL AKGKSDSKHC VIKEINFEKM PIQEKEASKK
 51 EVILLEKMKH PNIVAFFNSF QENGRLFIVM EYCDGGDLMK RINRQRGVLF
101 SEDQILGWFV QISLGLKHIH DRKILHRDIK AQNIFLSKNG MVAKLGDFGI
151 ARVLNNSMEL ARTCIGTPYY LSPEICQNKP YNNKTDIWSL GCVLYELCTL
201 KHPFEGNNLQ QLVLKICQAH FAPISPGFSR ELHSLISQLF QVSPRDRPSI
251 NSILKRPFLE NLIPKYLTPE VIQEEFSHML ICRAGAPASR HAGKVVQKCK
301 IQKVRFRGKC PPRSRISVPI KRNAILHRNE WRPPAGAQKA RSIKMIERPK
351 IAAVCGHYDY YYAQLDMLRR RAHKPSYHPI PQENTGVEDY GQETRHGPSP
401 SQWPAEYLQR KFEAQQYKLK VEKQLGLRPS SAEPNYNQRQ ELRSNGEEPR
451 FQELPFRKNE MKEQEYWKQL EEIRQQYLND MKEIRKKMGR EPEDIEKDLK
501 QMRLQNTKES KNPEQKYKAK KGVKFEINLD KCISDENILQ EEEAMDIPNE
551 TLTFEDGMKF KEYECVKEHG DYTDKAFEKL HCPEAAFTEL TWLSFLFLEY
601 SLPHFLLEKS PFSRHLIEDL LCANDCSLKD WSEKEMELRT  (SEQ ID NO:2)

FEATURES:
[1] PDOC00001 PS00001 ASN_GLYCOSYLATION
N-glycosylation site
Number of matches: 3
      1    155-158 NNSM
      2    183-186 NKTD
      3    549-552 NETL

[2] PDOC00005 PS00005 PKC_PHOSPHO_SITE
Protein kinase C phosphorylation site
Number of matches: 7
      1      48-50 SKK
      2    199-201 TLK
      3    243-245 SPR
      4    342-344 SIK
      5    573-575 TDK
      6    627-629 SLK
      7    632-634 SEK

[3] PDOC00006 PS00006 CK2_PHOSPHO_SITE
Casein kinase II phosphorylation site
Number of matches: 9
      1      48-51 SKKE
      2      69-72 SFQE
      3    243-246 SPRD
      4    385-388 TGVE
      5    430-433 SSAE
      6    444-447 SNGE
      7    553-556 TFED
      8    627-630 SLKD
      9    632-635 SEKE

[4] PDOC00007 PS00007 TYR_PHOSPHO_SITE
Tyrosine kinase phosphorylation site
Number Of matches: 2
      1    410-417 RKFEAQQY
      2    511-517 KNPEQKY

[5] PDOC00008 PS00008 MYRISTYL
N-myristoylation site
Number of matches: 4
      1     97-102 GVLFSE
      2    285-290 GAPASR
      3    336-341 GAQKAR
```

FIGURE 2A

```
      4    426-431 GLRPSS

[6] PDOC00017 PS00017 ATP_GTP_A
ATP/GTP-binding site motif A (P-loop)
             18-25 AYLAKGKS

[7] PDOC00100 PS00107 PROTEIN_KINASE_ATP
Protein kinases ATP-binding region signature
             10-33 IGQGAFGKAYLAKGKSDSKHCVIK

[8] PDOC00100 PS00108 PROTEIN_KINASE_ST
Serine/Threonine protein kinases active-site signature
           124-136 ILHRDIKAQNIFL
```

<u>Membrane spanning structure and domains:</u>

| Helix | Begin | End | Score | Certainity |
|---|---|---|---|---|
| 1 | 587 | 607 | 0.898 | Putative |

```
BLAST Alignment to Top Hit:
>CRA|18000004898313 /altid=gi|1709251 /def=sp|P51954|NEK1_MOUSE
            SERINE/THREONINE-PROTEIN KINASE NEK1 (NIMA-RELATED
            PROTEIN KINASE 1) /org=NIMA-RELATED PROTEIN KINASE 1
            /dataset=nraa /length=774
          Length = 774

 Score =  389 bits (988), Expect = e-107
 Identities = 239/631 (37%), Positives = 350/631 (54%), Gaps =
74/631 (11%)
 Frame = +1

Query: 1      MDKYDVIKAIGQGAFGKAYLAKGKSDSKHCVIKEINFEKMPIQEKEASKKEVILLEKMKH 180
M+KY  ++ IG+G+FGKA L K  D +H VIKEIN  +M  +E++ S++EV +L  MKH
Sbjct: 1    MEKYVRLQKIGEGSFGKAVLVKSTEDGRHYVIKEINISRMSDKERQESRREVAVLANMKH 60

Query: 181  PNIVAFFNSFQENGRLFIVMEYCDGGDLMKRINRQRGVLFSEDQILGWFVQISLGLKHIH 360
            PNIV +  SF+ENG L+IVM+YC+GGDL KRIN Q+G LF EDQIL WFVQI L LKH+H
Sbjct: 61   PNIVQYKESFEENGSLYIVMDYCEGGDLFKRINAQKGALFQEDQILDWFVQICLALKHVH 120

Query: 361  DRKILHRDIKAQNIFLSKNGMVAKLGDFGIARVLNNSMELARTCIGTPYYLSPEICQNKP 540
            DRKILHRDIK+QNIFL+K+G V +LGDFGIARVLN+++ELARTCIGTPYYLSPEIC+NKP
Sbjct: 121  DRKILHRDIKSQNIFLTKDGTV-QLGDFGIARVLNSTVELARTCIGTPYYLSPEICENKP 179

Query: 541  YNNKTDIWSLGCVLYELCTLKHPFEGNNLQQLVLKICQAHFAPISPGFSRELHSLISQLF 720
            YNNK+DIW+LGCVLYELCTLKH FE  N++ LVLKI    F P+SP +S +L SL+SQLF
Sbjct: 180  YNNKSDIWALGCVLYELCTLKHAFEAGNMKNLVLKIISGSFPPVSPHYSYDLRSLLSQLF 239

Query: 721  QVSPRDRPSINSILKRPFLENLIPKYLTPEVIQEEFSHMLICRAG--------------- 855
            + +PRDRPS+NSIL++ F+   I K+L+P++I EEF    + + G
Sbjct: 240  KRNPRDRPSVNSILEKGFIAKRIEKFLSPQLIAEEFCLKTLSKFGPQPLPGKRPASGQGV 299

Query: 856  ----------APASRHAGKVVQKCKIQKVRFRGKCPPRSRIS--VPIKRNAILHRNEWRP 999
                         PA+++   +  K    K     K PP+ + +  +P+K+   ++  E R
Sbjct: 300  SSFVPAQKITKPAAKYGVPLTYKKYGDKKLLEKKPPPKHKQAHQIPVKK---MNSGEERK 356

Query: 1000 PAG--AQKARSIKMIERPKIAAVCGHYDYYYAQLDMLRR----------RAHKPSYHPIP 1143
     A K R ++ IE+ K            + + + ++R              RA +  +  +
Sbjct: 357  KMSEEAAKKRRLEFIEKEKKQ----KDQIRFLKAEQMKRQEKQRLERINRAREQGWRNVL 412

Query: 1144 QENTGVE----DYGQETRHGPSPSQWPAEYLQRKFEAQQYKLKVEKQLGLRPSSAEPNYN 1311
            +     E    +G      PSP      +Y         + Y   ++    LR    E  +
Sbjct: 413  RAGGSGEVKASFFGIGGAVSPSPCSPRGQY-------EHYHAIFDQMQRLRAEDNEARWK 465
Query: 1312 ---------QRQELRSNGEEP-RFQELPFRKNEMKEQE--------YWKQLEEIRQQYLN 1437
```

FIGURE 2B

```
                +RQ+      E    + +E    RK E   + +         Y  +L +IR Q   N
Sbjct: 466  GGIYGRWLPERQKGHLAVERANQVEEFLQRKREAMQNKARAEGHVVYLARLRQIRLQNFN 525

Query: 1438 DMKEIRKKMGREPEDI----------EKDLKQMRLQNTKESKNPEQ---KYKAKKGVKFE 1578
             + ++I+ K+   E ++           E D++  ++++ K    N      K + ++  K
Sbjct: 526  ERQQIKAKLRGENKEADGTKGQEATEETDMRLKKMESLKAQTNARAAVLKEQLERKRKEA 585

Query: 1579 INLDKCISDENILQEEEAMDIPNETLTFEDG 1671
               +K + +E+++   ++ D+P      E G
Sbjct: 586  YEREKKVWEEHLVARVKSSDVPLPLELLETG 616 (SEQ ID NO:4)
```

HMM results:

Scores for sequence family classification (score includes all domains):

| Model | Description | Score | E-value | N |
|---|---|---|---|---|
| PF00069 | Eukaryotic protein kinase domain | 299.8 | 3.4e-86 | 1 |
| CE00022 | CE00022 MAGUK_subfamily_d | 28.3 | 3e-08 | 1 |
| CE00031 | CE00031 VEGFR | 21.6 | 1.3e-06 | 1 |
| CE00359 | E00359 bone_morphogenetic_protein_receptor | 8.8 | 0.081 | 1 |
| CE00203 | CE00203 ERBB_RECEPTOR | 2.2 | 2.9 | 1 |
| CE00220 | E00220 ACTIVIN_RECEPTOR | 2.0 | 5.7 | 1 |
| CE00287 | CE00287 PTK_Eph_orphan_receptor | -2.0 | 4.3e-08 | 1 |
| CE00292 | CE00292 PTK_membrane_span | -9.2 | 1.2e-08 | 1 |
| CE00291 | CE00291 PTK_fgf_receptor | -50.8 | 8.8e-06 | 1 |
| CE00289 | CE00289 PTK_PDGF_receptor | -64.6 | 0.17 | 1 |
| CE00290 | CE00290 PTK_Trk_family | -80.7 | 6e-10 | 1 |
| CE00286 | E00286 PTK_EGF_receptor | -84.2 | 5.8e-06 | 1 |
| CE00288 | CE00288 PTK_Insulin_receptor | -175.5 | 2.9e-05 | 1 |
| CE00016 | CE00016 GSK_glycogen_synthase_kinase | -218.2 | 0.00014 | 1 |

Parsed for domains:

| Model | Domain | seq-f | seq-t | | hmm-f | hmm-t | | score | E-value |
|---|---|---|---|---|---|---|---|---|---|
| CE00289 | 1/1 | 3 | 103 | .. | 1 | 109 | [] | -64.6 | 0.17 |
| CE00220 | 1/1 | 124 | 141 | .. | 340 | 357 | .. | 2.0 | 5.7 |
| CE00203 | 1/1 | 106 | 154 | .. | 843 | 890 | .. | 2.2 | 2.9 |
| CE00359 | 1/1 | 124 | 175 | .. | 272 | 326 | .. | 8.8 | 0.081 |
| CE00022 | 1/1 | 120 | 195 | .. | 138 | 217 | .. | 28.3 | 3e-08 |
| CE00031 | 1/1 | 111 | 200 | .. | 1054 | 1144 | .. | 21.6 | 1.3e-06 |
| CE00286 | 1/1 | 7 | 236 | .. | 1 | 263 | [] | -84.2 | 5.8e-06 |
| CE00288 | 1/1 | 6 | 253 | .. | 1 | 269 | [] | -175.5 | 2.9e-05 |
| CE00287 | 1/1 | 4 | 254 | .. | 1 | 260 | [] | -2.0 | 4.3e-08 |
| CE00291 | 1/1 | 8 | 257 | .. | 1 | 285 | [] | -50.8 | 8.8e-06 |
| CE00292 | 1/1 | 6 | 257 | .. | 1 | 288 | [] | -9.2 | 1.2e-08 |
| CE00290 | 1/1 | 7 | 257 | .. | 1 | 282 | [] | -80.7 | 6e-10 |
| PF00069 | 1/1 | 4 | 259 | .. | 1 | 278 | [] | 299.8 | 3.4e-86 |
| CE00016 | 1/1 | 1 | 324 | [. | 1 | 433 | [] | -218.2 | 0.00014 |

FIGURE 2C

```
   1 CTTGGCAGGC CGCCGCTGTG GCCCAAAGAG TAGGAAGCCG TTCCAGTCTC
  51 ACGTCCACCT TTTGGCAATA TTTGAGACCT TGTACAAGAA ACACTCTTCC
 101 TGTATCAGTT TAGCTCATTT GTAAAACTGG GAGACTACTG CCTTGACGGG
 151 TTGTAAAGAA AAGAGAGAAC GTTTGCGAAG CGTCTGGTGC ACCTTAAGCA
 201 AGAGCGGGGA GCGCTACTGT AGACTGCAAA GCAAAGGAAT CCCGACCCAA
 251 GGCAACGGGA CGGTTGCGGG GTGACTCTGC CGGGTCTCCA AACTCCCTGG
 301 CGCCTGACCC TGCCTCGAGG TGGACTGGTC CCCAGGCCAT TCCAGACCCG
 351 CGCCCCGCCC GCGTTTCCTT GCGCGGCTCC GCCCCGGCCG CAGGGAGGCG
 401 CAGCGGCCCC GGGAACCCGG ATCCTTCCGG GACGCTTCGT TGGCCCCGCG
 451 GAGCCGGCGG AGCAGGTACG CTTGCAGGGG CCGCCCTTAG TTCTTGCCCG
 501 GAGCCGCCAC AGGGCTTCGG GAGCTCGGCA GGGTGGGGGA AAGGGATGGA
 551 GTTTCGGCCT GGGGCGGCGG GGGCGGCCCA GAAAAGGCCT AGCGTCCTGG
 601 GCTGTGTGGG TGTAGCGTCC AGGGCGCGTC GGTCTCTATG GCAACGCTCC
 651 ACACGCGGAG GTCGGGTACG GGTAAGCGTC TTGCCACTCA CCCGCGGCCG
 701 CTTCCAGGGG CGGCCCTAGG GGAGAAGGAA TTTTCCTAAT TTGGGGGCTT
 751 CCACCCTTTG GTGCCACTTG GGCGGGAGGG TCGCGGGCCC TCAGTTCCCG
 801 GCGAGTCACC CCCGGCCCCA AGTCCGTATG CGTCTCTCTC AGAACCCGAT
 851 CCTCCGGTGT CTGCAGCCTC TCCTGGCTGC GGAGCTGGTT CCCAGCCCCC
 901 TGCAACCCAG TACCGACTTC CCACCCTGAC GTAAAATTAT TCGAAAACAA
 951 GCCCCCTGCT CACCCCATTA ACAACAACAA CAAAACTGTA TTATGCCCTA
1001 ACTGTAGCAT AAAGAGGAAA TAGAAGGAAA GCAATAAGTA AGAAAGTACA
1051 TATTTCAATC TGAAAATGCT TGGCACTACT ACCCTTGGAA AATGTAGAGA
1101 AGTAGCCAGT AGCCGCGCCT GGGGAGTCGC CTGAACGTGA CGGCAGCAAA
1151 TGCAGATTGT TGGGTCTCCG GGACCAGGAG CAGCGTGGCC AGTGAAGCGC
1201 GTGGTTTTCC CAAATGGTGA ACAATTCTTG GTAAACCTCC AAACCGAAGT
1251 GCAATCAAGC CTTGATTTAC ATGTAGTTGC ATTCCTCGAA AAAAAAAAGA
1301 AGTGTTCATT AAAACTGCAA AAATACTTAG CATTTCGATG TAAAATAGAG
1351 TTTGGTTCTA GCCACAAACG GATTTTTCCA CGCACAGGAA TGTATAGGAA
1401 GACTCTCCAA GATTGTAGGG CCGCGGGGTA ATCCTTTATT GTGCGGGACT
1451 GTCTCTCGAA TCGCAGAATC CTACCATCTC AGGCCCCAAC CACCTGTAAA
1501 CCTCATGCCT CTGAATCTTG GGGAAACAGC TTCCCCACCC CCATATATTT
1551 CCAGAATTCC CCCTAGGGGG CAGTACGTCC CCACTAAGAA AGGCTGAACT
1601 ATAAAAGTGC ACAAGCCTAA GGACATTCCT GCTTTATAAA GGTGCGAAAC
1651 ACCGGATATA GTATCTTTCA TTCTCAGAAC AAACTTGCAA AACAGGTATT
1701 GTTATTCCAT TTTAGAAATT AGGAAAGTGA GGTTTTGCCA GGTTAAGTGA
1751 CTTACCCGAG AATACAGGGC AAAAGTGTAT CAAAGCTGAG CTATGACCCG
1801 TGTCTGACCA AGAAACTCTG TCTCATTTCA GTTATCTGTG GCCACAAAGA
1851 AAGTTATTTG TCTCTGTCTT GGCAAGGCTG GGAGGAAAGT TTTAGCTAAG
1901 TGAGTTCTTT TACACTTTAG TCATCAGTTT TCTGACTTTG TTAGTCTTTA
1951 TGAGACGTGT GTGATAAATT TACATTACTC TAATTCCAGG AAACTCAGCC
2001 CATTGGAGAC CATGGATAAG TACGATGTGA TTAAGGCCAT CGGGCAAGGT
2051 GCCTTCGGGA AAGCATACTT AGCTAAAGGG AAATCAGATA GCAAGCACTG
2101 TGTCATAAAA GAGATCAATT TTGAAAAGGT AAAGTTAAGT TCAAATTTCT
2151 GTTAATTTTC AGTGGGATAT TCAGCTGGCT TTTAATCCAA TATAAAAAGG
2201 AAATTTTTAT TTTTTATAAT TTCGAATTTT AAGCCATAAT TGATTTTTGT
2251 TAATTCAACC TCCTAAGTCC ATTGTCCAAA CAGCAACCAA TGATCTCATT
2301 TTTAAAAAGA GGCTGGACGC ACTGGCTCAC CCCTGTAATC CCAGCACTTT
2351 GGATGGCCAA GGTGGGAGGA TTGTGTGAAG CCAGGAGTTC GAGATAGCCT
2401 GGGCAACATA GCAAGACCCT GTCCCTGCTA AAAAAAAATT TTTTTAATGA
2451 AAATAGAAAA GAAATAAGAT CACATCCCTG TGGCTCCTAT GGCCCTCCTT
2501 AGGGTGCCCT GCAAGGCCCT GTGAGATGCC AGCCTCCTCT GTTGCCCTGA
2551 CTTTTCTCTG TGGTGCACTT CCTCTCTCCT TATTCAGGTC CTCTACGAGG
2601 GGTTTTCTGC AAACATCCTA GCTAGAGTAG ACCCCCAGCC ACAATCACAC
2651 CTTATCACCT TATCACACCA CCTTGGTTCC TGGTTTCTTT TTTGTTTTCT
2701 TTTCTTTTCT TTTTTTAGAC GGAGTCTCGC TCTGTCACCT AGGCTGGAGT
2751 GCAGTGGCAT GATCTTGGCT CACTGCAATC TCCACCTCCG GGATTCAAGC
2801 AATTCTCCCA CTTCAGCCTC CTGAATAGCT GGGACTACAG GTGCATGCCA
2851 CCATGCCTGG ATAATTTTTT GTATTTTTAG TAGAGATGGA GTTTCACCAT
```

FIGURE 3A

2901 GTTGCCCAGG CTGGTCTTGA ACTCCTGAGC TCAAGTGATC TGCCCGCCTT
2951 GGCCTCCCAA AGTGCTGGGA TTACAGGCTT GAGCCACTGC TTCTGGCCTG
3001 GTTTATTTTC TTACTAGCAT GTATAATGCT CTGCAATTAC TTTGCTCTCT
3051 TAATTATTCA TTTGTTTATT GCTTGTCTTC CTCAGTATGC AGAACAGTTC
3101 CTGTCACATA ATAGGTGCTA AACACATTTA TTGAGTGCAC TGAATGAATA
3151 GAGAAAAACT ATATGTAATT GTTGGTCTAA TGATTTTGGA AAATAAATAT
3201 AGTTAATTAA AAATTAATAA TTTTTGCTAA ATCCACCTTG GTCAGTGTTT
3251 ATGTCACCCT CTTTAGTGAT ATGTTCATTT CATAATATAT TGGGACAACA
3301 ATGTCCATTG TTTGCTAGAA TTAATTCTAA GGCAAGTCTT GTTGGTCAGC
3351 TTCTAGAGGA TTTATAAATG AGAGTAGCAT AAAAAGTTCC ATACAAAGTG
3401 TGTGCAAAAT GGACTACCCA AGTTACACCA TATGAATATA CTTAATGCCA
3451 TTGAACTGTA CACTTAAAAA TCGTTAAAAT GATATAAATT TTATCTTACC
3501 ACAAAAAATT GCAAGAAAAC CTACCCAAAC TTAAAGCTCA AGAGTAGATG
3551 ACTGGCTTCC AGGGATAATG ATTTATTTCC CAATATAGGT CTCTTTTTGT
3601 GAATCCATGG CATATTCATA ATAATGTCCT CTTATTCTAG TGGCCCGCAA
3651 TAGCTTCCTC CCATGACATT ATTCTGCTCA CTCTCTTTTG TTTATCTGAC
3701 TGCTCTCCCT CAGGCTTATC TCTGTCTTCG CCCTGTGTAT GTCCTCAACC
3751 ATGTGTCCTT TTCTGATTTT CTTTTTCTGT CCATTGTCAC CTAAACTGCC
3801 CCACTTCAGT GTTTACCAAT AAGTAGATCT CTCTTAAATC TCTGTCTCTA
3851 CCCCTGGCAT CTTTCAGTAC CCTAGTTCTG CATTTCTTCT GCCAGCTAGA
3901 TAACTTCAGG TAATATCTGT GGTTTTGTTT TGAGGTGGAG TCTCGCTCTG
3951 TCGCCCAGGC TGGAGTGCAG TGGTGCCATC TCGGCTCACT GCAAGCTCTG
4001 CCTCCCAGGT TCATGCCATT CTCCTGCCTC AGCCTCCCGA GTAGCTGGGA
4051 CTACAGGCGC CCGCCACCAC GCCTGGCTAA TTTTTTGTAT TTTTAGTAGA
4101 GACGGGGTTT CACTGTGTTA GCTAGGATGG TCTCAATCTC CTGACTTCGT
4151 GATCCACCCG CCTCGGCCTC CCAAAGTGCT GGGATTACAG GCATGAGCCA
4201 CCACACCCAT CCAACATCTA TGTTATTAAT CTATTGCTGT GTAGCATATT
4251 ACCCCAAACT TAGTGGCTTA AAGAATAAAC ATTTATTGTC TCAGAGATCC
4301 TGTGCATCAA GAATTTAGGA TGACGATCAT TGAGACCACC TTGGAGGCTC
4351 GGTATCACAA TTGTACCCAA AAACAAGTAT TAATAGTGAT TCTTCCTTGT
4401 TGTAAGCAGA CCCACTTCAC CTCCTATGTG CTGCGCTGTA TTAATGTCAT
4451 CAGTGTCCTT ATGGTTGCCA GCCTGAAAAC CTTGGGATCG TTTGTGAGCT
4501 TATTCCTTCT CCACATTCAA TTATTTGGCG AATACTGTTG ACTCTTCCTC
4551 TTCCTTGAAT TTGCTTCAGT CCTTTTGTCG AGGCCCTGGG TCACTTGGAT
4601 CCTTCAAGTG GCTCCAGCCC AATTTTGATA ATGCTCCAGC CATGCCCCCA
4651 AACCTTCACT GGGACAGAGG CTGTAAAGAA AGAGTTGCCT AGGTTTGACT
4701 ACATAAAAAT AGAAAACGTT TGTATGTCAA AACAAACACT ATAAATAAAT
4751 TCAAAGAAAT CGAGAAGGTG CCAAAAATAT TTGCAAGTAT TGACTTAATG
4801 GTGTTAGCCT TTTATTAAAT CAATAAAAAG ATAAAATCCA TATATGAAGT
4851 CATCGTACAA AAATTTGAAA CTCAGTAGAA AACTAAGAAA TTAGGAGTTT
4901 ATTCAAAGAA AAACCCCACA GATAAACAGT TAGAAAACAA ATGTCCAACA
4951 GTAGGTAATT TGTTAAGTAA TTTATAAAAA ACTAAGTGGC TATTAGCAAT
5001 CATGTTGTAG GTGAAGCATT GACATGGGAA AATTTCAATG TTTGCAATGT
5051 TTGAGAAAAT AGTAAGTGTA AAATAATATA ATCTTTGGAA AAATATATAT
5101 ATTCTCCATA TATATGTATA CCTACAAATA TGTTCATATA TGTACAAAGA
5151 AAGACACAAA TTGTTATTAT TGAGGTAGAA AGTGGGGTTT GCCTTGTGCA
5201 TTTTTTTTGA GACAGGATTT CATTCTGTTG CCCAGGCAGG AGTGCAGTGA
5251 CATCATCATG GCTCACTGTA ACCTTGAACA AGCCATCCTC CTGCCTCAGC
5301 CTCCTGAGTA GCTAGGACTG CAGGCATGCG CCACCACACC CAGCTAATTT
5351 TGAAATTGTT TTTAGAGACA GGATCTTGCT ATGTTGCCCA GGCTGGCCTC
5401 AAGTGATCCT CCCACTTTGG CCTCCCAAAG TGCTGGGATT ACAGGTGTTA
5451 GCCACTGTGC CTGGTCTGCC TTGTGCTTTT ATATTGTTTC ACTCTTCAGA
5501 GAAGTTTTGA GACCCTCTCT GATTTGCTCC AAAACTACAG CTCCTATCAC
5551 ATACCCTACT TTTTTTCCCC ACTCCAGCCT CTGCATTTGC TTCTGGGGCT
5601 ACTTCTTCCA AGGTCGTTGC CTGCTGATCT CCCAGCATCA AGATCCCACT
5651 TGTTCAAGGC TGAGCTCTAC CATACCTCCA GAATCCTCCC ACTCTAAAGA
5701 ATTTATCCTT CTCTGTAAAC TTGCATAACT TTTATTGGAA CCTCTGTTAT
5751 AGTACTGACT GCTTTCTTTC TGGACATGCT TTGGCTGTTT ATTTTGTGCC

FIGURE 3B

5801 TTCTCCTCCT TATTTAGCTG TAATATGTTC TGTGAGGACC GAGTCCATGT
5851 GTGTTTTGTG CTGGTATTCC ACACAGCACC TAATGCTTGG TGCCAGGAGA
5901 TATTCAATAA CTTCTTATTG GATAGATGAT TCACTGGACA GATGCTTTCA
5951 GGCCCTCTTG CTCTACTGTG AAGCTGGTAT ATACTTAGGA ATTATAAAAC
6001 CATTTTAATT CTATGTAAAG AGAAAATATT TGAGAGGTGA ATCTCTATAA
6051 AAATGTACAT TAACATTACT GCATTTCATA GCATCTCTCC CATTCTTTAG
6101 TATAATCAAA AATTGACTAT ATTTTTCTAA TAGAGCACCA ATTTTTCATC
6151 ACTTTACTCA TGAACTACTC TTGTCACTAT GCCATAAATA AGTAGAATCT
6201 TATATTAGAC CTCATTATTC TTGTTTTCCC ATATCTGTTT ATGTTATCGA
6251 ATTTACCTAT AACATCTGTG TCACAATATT AACATTTATT ACTTCTTTCT
6301 TCCTATCTAC TCTCATGTAG TTTTTCATTA CTTCTTATCT AGAGAAATTT
6351 ATATTTCTTC TCTCTAATGC CTCCCTACTC CCTACACTAG ACCCCAGAAC
6401 TAAATTGCTT GTTTTCTTAC AGGTACCAAA AAGCTAATAT TTCTCTTATC
6451 ATCCTACCAT TATCAAGCAT GTTCTTTTCC TTCTGGGCTC AAATAAAAGT
6501 GTTTTATCTT TCCTCAATTG TGAAAATAAA AATGTTCGTT GTAGAAATTT
6551 TGAAAAGAGC CAAAGGAGAA AATAAGACCA TTTAGAGGAA AATAAAAATA
6601 GCATATAACC TCTTTCTTAA TCACTATGAA CACTTTGCTG AATTTCTCTC
6651 TAGACTATTT TTAATGTATA AGTATATAAG TTATTAGAAT GATTGGTGTC
6701 ATGGTAGATA TACTCTTTTT TTTTTTTGAG ACGGAGTCTC GCTCTGTTGC
6751 CCAGGCTGGA GTGCAGTGGC GTGATCTCTG CTCACTGCAA TCTCTGCCTC
6801 CCAGGTTCAA ACAATTCTCC TGCCTCAGCC TCCTGAGTAG CTGGGACTAC
6851 AGGCGCATGC CACCATGCCT GGCTAATTTT TGTATTTTTA GTAGAAACAG
6901 GCTTTCACTA TGTTGGCCAG GCTGGTCTCG AACTACTGAC TTCGTGATCT
6951 GCCTGCCTTG GCCTCCCAAA GTGCTGGGAT TACAGGTGTG AGCCACTGCG
7001 CCCAGCCCAG GTATACTCTT TTGTAACAGT TTTTTATATT AGCAATATAT
7051 TGTGAATATT TCCTCATCTC ATTCAATATT TTTATATAAT AAAATGTTGT
7101 CATTTAATGA TATTAAATGT GTTCACACTA ATGATAAAGG GACCACCTGC
7151 AGGGTGTCCA TTATATGTCA CACCATCCTG GGTGTTTTAT TATGTATATC
7201 AACTCAATTT AATCTTCACA ACCACTTAAA AGGTAGCTCT CATTACTCTC
7251 ACTGTACAAG TGAAAGAGCT GAGGCTAAAG AGGTTAAGCA GTTAGCTCCA
7301 GGATGCACAG TAATCAGCAG ATCCATCTAA GTCTTTCTCT GCTCTTTCCA
7351 TGATACTACA TTGCCTCCCT TTATTTTTAA TGACTGCATA GCATTAAAGT
7401 GGTAGCAGGT CAAAAATACC ATAATTTAGC TGGGCATGGT GGCAAGTGCC
7451 TGTAGTCCCA GCTATTCTGG AGGATGAGTT GGGAGGATCC CTTGACCCCA
7501 GGAGTTAAAA TCCAGCTTAG ACAACATAGC AGAACTCTGT CTTAAAAAAA
7551 AAAAAAAAGC TAGCAAAACA CCCCTGTAAT TTATTTAACT CTTTTTCTAT
7601 TTTCAGATAA TTACATTGTT TGGTTGGTTT TTTGGCTACG ATTCAATAAC
7651 ATTTAATATG TAAAGTATGA TTCATTTTTA TTAAACAAAA CTATGTATAT
7701 ATGCTTGCCT ATATATGCAT GAAATAAAAA GCTCTAACTA TTAACAACAG
7751 TTATCCCTAG GGAATATAGT ATTAGGTTGG CGCAAAAGTA ATTGCATTTT
7801 TGCCATTAAG AGTAAGGTTA CCACCTATGG GCTTTCGTCT GTGGGCTAGA
7851 TGAGAAAGAA AGAGGGAAGT TTCACTTTTA CCTTATTCAC TTCTATTTGA
7901 CTTAAAACAA GCGTGCATTA TTAGAGTAAC TTAAAAACTA GCAATAAAAC
7951 ACTGTAACAA AGTCTTTTGT ATGAGAACTC TTCTGTACCC TTTTATTATC
8001 TTCTTTGGAT AAATTTCTAG AAGAATTAGT CAAAAATAGG AACATTTCCC
8051 TCATGCCTGT AATCCCAGCA CTTTGGGAGG CTGAGGCAGC TAGATCACTT
8101 GAGGCCAGGA GTTCGAGAGC AGCCTGGGCA ACATGGTGAG ACCCCATCTC
8151 TACTAAAAAT ACAAAAAATT AGCCGGGTAT GATGGTGCTT GCCTGTGGTC
8201 TCAGCTACTC AGGAGGCTGA GGTGGGAGGA TCACTTGAGC TCAGTGGGCA
8251 GAGGCTGCAG TGAACCAAGA TCATGCCACT GCACTCCAGC CTGGGTGATA
8301 GAGCAAGACC TTGTCTTAAA AAAAAAAAAA AAAAGATTTC TTCAGCAGGA
8351 TACAGACCCC CCACAAAAAT GAACATTTTA AAGATTCATA TTATATATTG
8401 TAAAACTGCC TTCCCAGAAA TATTTTATCA ATTTGTGTAG TTTTACCAGA
8451 AATAAATGAG TGTCCATTTT GCTGCTTTCT GGCCAATAGT AGTTATTGAC
8501 ATTCTTTTCA TCTTTGCCAG TTTCATACAT GGAATACTAT ATTACATTTT
8551 GTTTTAGCTT TTATTCCTTT TTTTTTTTTT TTGCAATGGA GTCTTACTCT
8601 GTCACCCAGG CTGGAGTGCA GTGGTGTGAT TTTGGCTTAC TGCAGCCTCC
8651 ATCTCCCAGG TTCAAGGGAT TCTCCTGCCT CAGCCTCCTG AGTAGCTGAG

FIGURE 3C

8701 ACCACAGGTG TGTGCCACCA CGCCTGGCTA ATTTTTTGTG TTTTTAGTAG
8751 AGACAGGGTT TTGCTATGTT GGCCAGGCTG GTCTTGAACT CCTGGCCTCA
8801 AGTGATCTGC CTGCCTTGGC TTCCCAAAGA GCTGGGATTA CAGGCATGAG
8851 CTACCACACC CAGCCAAATT TTGCTTTAGT TTTTATTCCT TTGATTACTG
8901 CATGAGATTG AATATTTTTT CTATCAGCCA TTTTTATTTC TCTTTTTTTT
8951 TCGAGTTGAC TATTCTTGTA CTTTGCTATT TTTCTGTTGG GGTGTTTGCC
9001 TTTTTAAAAA TTATTTGCCA TCAATTTTTA TATTATAAAT ATATTTGTCA
9051 TATATGGTAC AAATATTGTA TCTTATCCTT TTGTTTGTCT TTTAATTTTG
9101 TTTATAATAT TCTTTTAAAT AAATAGTAGT TAGGAATTTT TTAAGTTGCT
9151 AAATGTATCC AGCTGGTAGG AGTAATTTAG CTGTTTTTGT TTTGAAACTC
9201 CTATGTACTG ACTATACAAT TTAAATTGGG GCAGGAAACA CTGAAGCTTA
9251 GAGGGGTTTA AGGAACTTAC TGAAGGATCC TTCAGCTGAG ATGTAGGGAA
9301 GCTAGAATTG AGAATATTAA TTTTTAAGAA GTTCTTAAGT CTAAATGAGA
9351 ATGAGAAATC TGGCCAATGT TGAAGACCTC TAATGGGTGG AGGCCCCGTG
9401 GACATCAGAA AAGCGGGGCA GTCAGGGGCT GGAAGTCAGG GTAGAAATGA
9451 CAAGTCAGCA AAGCATCAAG AGTGAGGAAG AAAAAGTAGA AATGAGGTGT
9501 GGCCACTGGT ACTGGCACCA AACCCCTTGG CAAGTATTGT CTATAGGTGA
9551 AAGTAGAACA AGAAAATACA CCCAAATACT TCTAAAATGA AGTCATGCAA
9601 GACAATTTTT ATTTGAAAAT GAAAAATGTA GTCATCTTAA TACAAAATTT
9651 TACTGACCTG ATTTCTGTGG GATATGACAC ATTTTCTTTT TTTAGATTTC
9701 ATTTGTTTCT TCTCAGCAGT GATTGCTCCT GGAATGTTGC ATTTTTATAA
9751 AGAATTCCTT CGCTACTGAA AGATAGATAT TAAAATATGG CTCCATATGG
9801 CTAGATAATG AACACGGTAC CACCAGTCCA ACTTTTAATA TAGCAAAACT
9851 TCACCAGAAA TATTTATTTT CTTGATGATG GTTGTCAACA AACCATTGAT
9901 GAGATGTAGG GCACTCTGCT AATTCTAGAA ATGTTGTTTC CTGCCATTGA
9951 AAGATCGTTT TCAAAGTGAC ATTAAAAGCC AGTGAAATCC TAGAGAATTT
10001 TAGATGGAAA TGAGCAGAAA GCATGTTCTT GAAACCAAGT TAGCTTTATA
10051 GACTACTCTG TCTCTTAATG TAATTTAGAT GCCCATACAA GAAAAAGAAG
10101 CTTCAAAGAA AGAAGTGATT CTTCTGGAAA AGATGAAACA TCCCAACATT
10151 GTAGCCTTCT TCAATTCATT TCAAGGTTTG ATTTTCTAAT ATTCGTTAAG
10201 TATTTTTATA AAGTATAGGC ATGTTGACAT ATGTAAAAAG ATTTGTTCCT
10251 AAGGACTGTG TATAAATTAA TTTTTGTAAA TGGGTCATTT CCCCATTTAC
10301 TTAAATTGCA GCTTGAGACG TCCTCGTTAT TTCCTCTCTA GTAAGTTTTT
10351 GTAGACGGCT TTCTTATGTT TTCTTGTTTT TCTGCCTCTC CTTAATTCTC
10401 ACTCTCCCAA AAAATTAATG ACTGGCTTAT TAGCTTCTTT GCTGTAGTAA
10451 CAACCCCCAA ATTTAAGTGA CTTACAATAA GACACATCTA TTTCTCACTT
10501 ACATTACATG CTAGCTGTGG TGGGCTGGGG TCTTGAGTCT GGGGCCCAGG
10551 CTGAAGGAGC AGCTCAGATA AGGAACCAGC TGTTCTCATA AGCAAGAGAA
10601 GAGGGGAAAA CACAGAGCCC ACCACACTAT CGCTCTCAAA GCCCTGCTAG
10651 GATGTGTGTG TTTGTGTGTG TGTGCTGGGG GGTACTCTGT TTACATGAGA
10701 TCCTGCATAT CCTCAGGCAA CAGATGGGAC TGTGTAATCC TCTTACAGAG
10751 AGCCAGCAAA CAGCCACGCA CCATAGCCTA GCACACTGCC ACGGAGAGGG
10801 GGAGAACTTT AGGGAAGGAA GTACCTTCCT CTGTACACCT GAATACAATT
10851 CTGCTGACAA CTTTAGGGAA GGAAGTCCCT TCCTCCATAC ATCTGAATAC
10901 AATTCTGCCT CCACGCATCA CTGTAGTCCA AAGGTAAAAA ATAAATAATA
10951 AATGAAGGAG CATTGGTCAG ACAGCATTCA TTCACTGAAC TGATACTTAT
11001 TGAGTGCTTA CTCTATGCCA GGCATTGTTC TAGGTGTCAG GAATATAGCA
11051 GTGAACAAAG CAGATGAAAA TCCCTGTTTT CATGAAATTT ATATTCTAGT
11101 GGGAAGAGAT AGACAATAAA CAAATCTACA GTATGTCAGG TGTGTCTTAA
11151 GTTGTGACAG GGCTGTATGT GCTGACAGTT TTATGAAGGG TCATTCCCCA
11201 GCCCAGCCCC CAGCGCAGGG CTGTTTTAAG ACTGATAATT AGTTCATGGA
11251 GCAGAAGTGT TAACCTCAAT ATCTTCAAGC ATCATCAGTT GGGTAAAAGT
11301 CAGTCAATAA ATAAATACAG CCACTGTGTC TTGAGTATGT AAACTGTGCA
11351 GAGCACTGTG TTCCTTACTG ATTAAAACCG CTACATTCAA GGTACTTCTG
11401 TGTGTATGGC CCTTCTTTGG CTTCTGGGTA TTTAAAAAGA GCTCTTGGGA
11451 CTCTTCTGAG GTCTTCCTGG GAGCAGAACA GTACACATGG TCTGGAATTG
11501 GGTTGCATGG AATAACTTTC AAGGAAAGCC ACTGAATAAA GTGCCCTGCA
11551 TTCCTGTCCA TTGGATACTG ATAATGCTAT AAGATGATCT TTCTCTTCTT

FIGURE 3D

```
11601 TATTTTGTTT GAGATTATTG TGACTCTCTG GCTAACTCCT ACTTATCCTC
11651 AGGCCTTTTC TGAACTCACA ATTCAAATTA CAGCTCCCTT TGGTTCTCTT
11701 CCACAGCAGT TGTACTTACA TATGTCTATT TATATAATTA TGAATTTGTT
11751 TCATATTTGT CGCCCTTTAC ATGGTAAACT TAATGAATTT TGGGGCTCCA
11801 TCTGTTTTGC TCACCACTTG ATCCTTGGCA TGTAGCACAC AATGGCTGCT
11851 CAATACCTAT TTACTGAATG AGCAAATGGA CTGGACCACT TTTAGAGACT
11901 GGAGTATTTC CTTATACCAT GTGAGATTGA TTTTTGAGGA CAGTTTACCA
11951 CTGGAAGCTT TTGCAGAACT AAGGTCATTT TTACAGTATA CATAACCTCT
12001 GCTGTGTTTG TTGATACTGT AAGTTTACAT TTTCTTATGA CTCTTTTTAA
12051 GTAGAGCACC CCTGTGTTTA GGAAAGCTAG AGCTATTGTG ATGCCTTTGA
12101 GTTTGCTTGG CTGATTGCTG GGACTTGAAC TACTGAGCTT ATCTAAAAGC
12151 CTCAGAGGCC TTGTAGCCTC TGTCTTTTAG AGAGTGTAGG TAAAGGCTTG
12201 TTTTCCCTCA AATCGCTTAT CTCTGATCAT AAGAACCATG GCTCTAATGT
12251 TTGTCTATAG AAAATAGAAT GTTTTGGCCG GGCGCAGTGG CTCATGCCTG
12301 TAATCCCAGC ACCCTGGGAG GCCGAGGCGG GCAGATCACC TGAGGTCAGG
12351 AGTTCAAGAC CAGCCTGGCC ATGGTGAAAC CCCGTCTCTA CTAAAAATAC
12401 AAAAACGTTT AGCCGGGCAT GGTGGTGTGC ACCTGTAATC CCAGCTACTT
12451 GGGAGGCTGA GGCAGGAGAA TCGCTTGAAC CTGGGAGGCA GAGGTTGCAG
12501 TGAGCTGAGA TTGCGCCACT GCACTCCAGC CTGGGCAAGA AGAGTGAAAC
12551 TCTGTCTCAA AAAAAAAAAA AGAAAATAGG ATGTTTTTAT TGGTTTGAAG
12601 CAACATAAGA AAAATAATGA GAATGTAGTG ATATTTTCCT AAGACAAAAT
12651 TAATTCCATG TATATTCCAT CAATAAACAT TCACTAAGTG TCTGTTATAT
12701 GCCAGGCATG TTCTAGGTCT TGGAGATATA TCAGCAAACA AAATAGGCAA
12751 AAATTCCCAT GCTGTTGTAT TTGTTTTCTA TTACTACATA ACAAATGAAC
12801 ACAAATTTAG TGGCTTAACA ACAACACCTA TTTATTATCT CTTGATTTCT
12851 GTAGGTCAGA AGCCTGAGGT TGGCTTAGCT GGATTCTCTG CCCGGAGTCT
12901 CAGCTAGTTG AAATCAAGGT GTCAGCTGGG ACTGTTATCT GTGGCTCATG
12951 GTCCTCTTCT AAGCTTATTT AGGTTGTTAT AGATTTCATT TACTTGCAAT
13001 TGGGTTAATT GGATCATGGC TCACTGCAGC CTTGAACTCC TGGCCTCAAG
13051 TGATCCTCTC GCCATGGCCT CCAAAAGTGC TGTGAGTACT GTGCCTGGCC
13101 AGAAAGAGCT CTTTTACATT TATTTAAACA CAGAGTTTTA TTTTATATTA
13151 CTCTAATGCA CACATAAAAA AGAAAATATA AGCAAACAAA GTTGGTTAAG
13201 GTATTCTAAA AATTATTTAG GCAGTGAAAA CATTAAGCCT GCCGGGTCTA
13251 CAGCAAGTGA TTGGAAGATG CCAATGTCTG TAAGAAACAA TCTTGATTTT
13301 TTTTTTTTTT TTTTTTGAGA CAGTCTTACT CTGTTGCCCA GGCTGGAGTG
13351 CAGTGGTGTG ATTACAGCTC ACTGCAGCCT TGACCTTCTG GGCTTAAGGG
13401 ATCCTCCCAC CTCAGTCTCC TGAGTACTGG GACTACAGGC ATGTACCCCC
13451 ACACCTGGCT AATTTTTGAA TATTTTTTCA TTATAGAGCC AGGTTTTCGC
13501 CATGTTGCCC AGGCTGGTCT CAAACACCTA AGTTCAAGCA ATCCACCTGC
13551 CTTAGCCTTG GCCTCCCAAA GTGCTGGGAT TACAGGAGAG AGCTGCTGCG
13601 CCAGGCCCTT GATTTTTTAA AAGTGCATTT TAGAATGAAT TATAATAATT
13651 GTTTAATAAA TGTTGGAATT TGACAAATAA AAAGGTTATT TAGTGCCCCT
13701 CAATTGTTTT GAAGTGTCAG TGATCCATGA GCTTTACAGC AGATGGAAAA
13751 TTTGAGAGCA TAAATGATTT TTCCAGACAC TTCCAATAAA TATAAAATTA
13801 ACAGTGGCTA ATGGGGGAAA ATCCTTATTT TACAGTCAGA TAATGCTAAT
13851 TGACATTAAG TAGTTTCTTT TTTTTTTTTT TTTTTTTTTT TTTGACGGAG
13901 TCTCACTCTG TCACCCAGGC TGGAGTGCAG TGGCACAATC TTGGCTCACT
13951 GCACCTCCAC CTCCCGGGTT CAAGCAATTC TCCTGCCTCA GCCTCCTGAG
14001 TAGCTGGGAT TACAGGCGCC CGCCACCATG CCTGNNNNNN NNNNNNNNNN
14051 NNNNNNNNNN NNNNNNNNNN NNNNNNNNNN NNNNTAATAA TCAGGGATTT
14101 AGAAATAGGA TGAAATGACA AGCTAAAGTC TTTGAGTCTT AGTTCCTCAG
14151 CTGTAAAGTG GGCATGGTAC CATTTCACAG GAATTGATAC GAGGATTAGA
14201 AGAGATTAGG GCTGTGAAGT GCCTGACACA CAGATAGTTC TTGAATCAAA
14251 TGAGGGTAAA TTGTAGCACT CATCTGTCTC ATAAGCCTAA ACTGCACATG
14301 TATCTATATA TTCATGACAA AAATCATTCC AACACCCAGG GGCTGTCCAA
14351 AATACATCTC TATCTCTCTG TATACCTATT CCCTCTCCAC CCCCCAAATC
14401 CTATACAAAT TCCTCTTCCT CGGCCGGGCA CGGTGGCTCA CGCTTGTAAT
14451 CCCAGAACTT TGGGAGGCCA AGGCGGGTGG ATCACGAGGT CAGGAGATCG
```

FIGURE 3E

```
14501 AGACCACAGT GAAACCCTGT CTGTACTAAA AATACAAAAA ATTAGCCGGG
14551 CATGGTGGCG GGCGCCTGTA GTCCCAGCTA CTCGGAGAGG CTGAGGCAGG
14601 AGAATGGCGT GAACCCAGGA GGCGGAGCTT GCAGTGAGCC GAGATTGCGC
14651 CACTGCACTC CAGCCCAGGT GACAGAGCGA GATTCCGTCT CAAAAAAAAA
14701 AAAAAAGGTA TCTCTGTCAT GATGAATTTT TAGTCAGTTT CTTTCACCAA
14751 AAGCCAGTGT AAGGTTGAGT GAGTTGGAGG TTGGTGAAAA GGAAGTGAGA
14801 TGAAATAATG TGTCTCCTCT GTTTCATTAT TCTGATTCTT CCATGGTTTT
14851 GAAATTGCCA TCCCTTCATT GCTGTGGCAG ACCTTTTACT GACTGAGCTT
14901 CAATGACAAG AAACATCAAT TCTCCTAAAA GTAACACATT CCTGAAAATA
14951 ACCGATCTCT AGACATTAAG GCATATGGGG AAGCATCTTC TCAGAACCCT
15001 TCCTAGATCT CCAGTCTTAC TTGCATGCGC TTTCTCCTCA CCCTCCAGCC
15051 TACAGACTTC TTCACAGCAC TTCTCACCCA ATGCTGAGGG ACTCCCCAAC
15101 TAGACTTCGC CTCCTTAACA GTAGAATGGA TGGCTTCTTT GCTTTTTATT
15151 CCTACACAGC ATTCCTTGCT TTTGCATGTC CTCAATAGAA GTTTGTTAAT
15201 AACTGAATGG ATCGTCTCTT AAAGAAGAGA GGAGGAAAAA TTGAAATATG
15251 TGAAAGAAGA TGCATGGTTT GTGAATTAGA AGCAACCAAG GGTAGACACT
15301 GCCAGGTTAC TGATATCCAC AGTAAAGTTG GTTAGGGTAC TTTAAAGAGT
15351 AGGATAGCAA AAGATAGATA TTTGGCAAGA GATTTTGGCA TTTAATGGGT
15401 ACTACAGGGG AAAATGTTAT CAACAATTGC TTATAAGACT GATTTTGGCG
15451 CTTATGTTTT GTGTTCCTTC AGGGTTTTTT TGTTTGTTTG TTTTTAATGA
15501 ATCCACTCAA CAAACATTTA AGCCCCTTTG ATGTGCTAAC TACTGTTTAG
15551 GTACAAAAGA ATGAAGTGTA GACAAACAAG TGAGTAGAAA TCCTTCTTTT
15601 CTAACAAGAT CCCAGCTGTT AGTTGGTTGG CTAATGAAGA AAGCTGGTTA
15651 GAGCAGAAAA TCATCTGTTT TAGTCTATTC CAGCAGCTAT AACAAAATAC
15701 CATAAACTAG GTGGCTTATA AACAGCAGAA ATTTATTTCT GGCAGTTCTG
15751 GAGGCTGGGA AGTGCAAGAT CAAGGTGCAG GCAGATTCAG TGTCTGGTGA
15801 GGGTTCACTT TCTGGTTCAT AGATGGTCCG CCTCATTGTG ACTTCACATG
15851 GTGGAAGGGG AGAGGGTTCT CTCTTGGACA GCAATCCATT AATGTGGGCT
15901 CCACCCTCAT GACCTAGTCA CCTTCCAAAA GCCCTATACC TCCTAATACC
15951 ATCACTGTGG GGGTTAAAAT TTCAACATAT ACATTTGGGG AAGACAAAGA
16001 CATTTGGATC CTAGCAATTA TACAGACATA TTTTAACATA AGAAGACATA
16051 ATCATCCTTT GAGTGGAAAT GGCCAGGAAA AAAAAAAAGA AAAAAAATTT
16101 AAGGAAATGA CAAGCATTTG TTAAAGGATA ATTTCTTTTC TTTAATACGG
16151 AGCAAGTGTT TGTGGATAAT CTGTCCACAA TCCTTTTAGA AGTTTTCTAG
16201 TTATATTTCA TTCATTTCAT TCAACATTTA GGTCAATGGT TATTTATTTA
16251 TTTATTTTTA AACTCACTGA GTCCTCCAAA ATATTCAGCA TAGCTTTTGG
16301 AGGAATAATC ACATCTTTCA TTTTCTATTC ATATTTCATC AGTTTATGTA
16351 ATAAAGACAA GAATAACTCA CTACAGTTCA AGAAAATTCA GAATTATAGT
16401 TGGTAGATTA TGAGTCCACT GACTATAGTT CTGAATTTTC TTTCTTATGT
16451 AAGTTATGTG TCTTATTTAG AATTTCTAGT CTCTTTTCTT TAATGTGGAG
16501 CAAGGATTTG TGGATAGTCT GTACATAATC CTTTTAGAAG TTTTCCAGTT
16551 ATATTTCATT CATCCCATCA ACATTTAGGT CAATAGCTAT TTTTTTTAAA
16601 AACTACTCAC TTTTACTGAG TCCTCCAAAA TATTCAGCAT AGCTTTTGGA
16651 AAATAATCAC CTTTCATTTT CTATTCATAT TTCATCAGTT TATGTTACAA
16701 AGACAAGAAT AAATGGCGTA AACATATTTG GGAAAAAACA AAATGATCTT
16751 GGTAAGATTC AGTTCAATTG GTAAGAGCAG AGGTACTTGG ACATACTAGA
16801 GAGCCTAGTA GTATTTAGTG GTAACGTTGA TGGGGCAATA GCAATGGAGA
16851 GTGTCCTGTA ATCTAGTGAG TGGTTTAGGC AGAGGTCAGT TATAAGAGTT
16901 TCTATTGTAT TCAACAACAT AGATAAATAA GTGCCATATA AATATGGCTT
16951 TATGCCCAAA TTCAAGAAGG GGCTATTAAT TCTTCCTGGG GTGTTATGAA
17001 AGAGTCACAG CTGCTATTTT TACAGCAGAT TTCTAACCTC TCAAAGGAAT
17051 GTATTAATAA AAATAGCCAA CATTTCTTAA ACTCTCATTA TGTACAGGCA
17101 TTATTCTAAG CATCTGACAT GGATTAACTC ATTTAATCTT TCCAACAATC
17151 CAAAGAAGAA ATTTCTATAA TATTTCCATT TTACAGATGA GGTAATGAGG
17201 CACGGAGAAG TTAAAGTGAC TTGCCCAGAG TCACAGAGCT AAGAAATATA
17251 AATGGTATAG TGGAATTAGA ACCCAGTCCA TCTTGATTCC ACAGCCAGAA
17301 CATGGCTGAT AAATATCTGA AATCCTTCCA GCACCAAATG ATTCCTTTTC
17351 TTACAGAGAA TGGCAGGCTG TTTATTGTAA TGGAATATTG TGATGGAGGG
```

FIGURE 3F

17401 GATCTCATGA AAAGGATCAA TAGACAACGG GGTGTGTTAT TTAGTGAAGA
17451 TCAGGTAAAA ACTTCTAATT TGCTTTTTAA TTTTATGTAT GTGTGGTGGG
17501 GGGAGAATTA AATTTATAAT GTCATAAGTA GTAGACTATG TTGATATAAA
17551 GCATGTGTTT TGGTAGACAG ATTGAAACCA TAAAATAGTG GATCAATATT
17601 CTTGGTAGAT TCAGTCCAGA ACAAGTTTGC AATTGAACTT AAACTGAATT
17651 GTTTTTTAGA GAGTGAGATT TTCTTGAGAA AAGATAATCT GTTTGGAAAA
17701 TCTCATGTAG GATGCCTCTG AGATAAGTCT TCATGGTTAA AAAAAAATCT
17751 GAATGTGAGT GTTCCTTAGC CATTTAACAT GTAACATATT TATAGCTTCA
17801 CTGTTTTCTC TTTTACCATT TGGTGCTCTG TTTTAAACTA GATATCCCAC
17851 TTTGCTAGGG AGGATAGAAG CTTGTCTTGG CAATGCCTAT TTAGTTTCAT
17901 TGGTTATTAA GAGGGGGAGA TAAAAGATGA AGAATAATGG CCTCTCCCAC
17951 TTTCTCTTTG CACAAATGTA TTTCTCTTCT ATACTCCAAG CCTCCCTGGA
18001 ACTCTCTTGG GAGTGGTACT CATGAAGGAG ACAGGTTTGT ATGTGTGGAG
18051 AGGAATCTGA ATTAGCTCCT TTATGATTGA TGGTAAGGCC ATTGCCTCAA
18101 GAAGCACACA GGAAAGGCCC ACCATCTTTC CTTTGGCCAT TGTTTCTTTG
18151 TTCTATTTTA GCATGTAAGA GCATCATGCC CATATAATTT CCTCTTAAAG
18201 TTGAATATTT TGAATATATG AAGGATTAAA AAATCAATAT CTCTAACTTC
18251 TGTAAGATTA ATCAAGCATT CTTTGTATGC TCATTTATAT TATATATTAA
18301 ATTCCATATT GATAGAAACT CTTTTTTCTT ATCTAGGTAT TATTTTGCCA
18351 CATTTTATAA AAATGCTTCT CATGACAAAA TTTTGAGTTA CATTTCTTTT
18401 TGTTGGGAAT GAACTAAAAT TACAACTGAA TATTAATGTC TGGAATATAG
18451 CTTTATTCCT ATTATTTTCC TCTTTCTGTA TAATTTGGCA GACAAAGAAC
18501 CAGTGAAATT TTAGAATAGT TTAAATAAAT CTCTGTAGGC ATAGAACACA
18551 TTTTCATAAA GAGGCTCATG GTCAACAAAG ATAAAATCAA ATCATGACTT
18601 AGAAATAAAA CTAAACTTCA AAGGTAAAGT ATTTGTTGGT TTTATATTAG
18651 ATATACTGAT ATTTTATTAC AATTCCTAAC CTCACAGATC CCCCATTTCT
18701 TCCTCTTTCT CTCCCCACCC TTGTCACCCT CCTTCCACTG TAAAGGAAGA
18751 ACCAATGGCT CCCAGGTTAT CAGGAAACAG GGCTGCTTGT GTACTATTCA
18801 CGATGCAGTT AGCACCCCAG GGTTAAGTAG GAAAAAAAGA AAAACATGAA
18851 CGGCATGCCT CTTTCCCTTG CTTCTACTTA TCTTTTTCTG CATGTGGAAT
18901 TTCCCTTGAT TTTACCAGTG ATATTTGGAT TACTTTTCTG TGCCTCCATT
18951 TTTTTAGTTG TAGAATGAAA ATAATAATAT GATAAAGTGT ACCTATTAAC
19001 TTCATTCCTA TAAATACACA TACACTATAT GTGTGTATGT GTGTGTGTGT
19051 GTGTGTATAA TTTCTATCTT TTTGCATGTT ACCATGAAGA CATTTCAGTG
19101 ACTACCAGGC TATTCAGTGG CTTTGTTTTG TGTTCTCTCT ATAGATCCTC
19151 GGTTGGTTTG TACAGATTTC TCTAGGACTA AAACATATTC ATGACAGGAA
19201 GATATTACAC AGGGACATAA AAGCTCAGGT AACAGCTCAG AGAGAAGACT
19251 AAGACAGAAC TGATCTTTTC TTGAAGTACC TCAAACAACA TGACATTTTC
19301 TCCATTTATA GAACATTTTT CTTAGCAAGA ACGGAATGGT GGCAAAGCTT
19351 GGGGACTTTG GTATAGCAAG AGTCCTGAAT AAGTAAGTAC TTTGAAAATA
19401 ATTTTTCTTT CTAGTCAAAA TAGCCCAAAT ATGTATTTTT AGATATCATG
19451 GATTAAGAAG ATATTAAAAT CTTGGTTGTC TAAATAATTT TAGGTAGCTT
19501 TATGTAAATG CATTACATCA GATGGTACTT TGAGATTAAA ATTCTCAAGA
19551 TAAATTGTGG TGTAATAGAA TGATGTTGCT AATATTCTGT AGTGTGATTC
19601 CAGTTTGTCA AATATGGATG TGACTGTAAT ATGCATAAAG CTAGAGAGAA
19651 TTTCGTGAAA TAGGCAGGTT TACACTTCTT AATGAAAAAA GTCAAACTCT
19701 ATAAAATATT TGAAGAGATT TATTCTGAGC CAAATACGAG TGACCAAAGG
19751 TCCATGCCTG TGACATAGCC CTCAGGAGAT CCTAAGAACA TGTACCCAAG
19801 GTGGCCGGTC TACAACCTGG TTTTGTACAT TTTAGGGAGA TGCAAGACAT
19851 CAATTAGATG TACATGGGTT TGGTCCAGAA AAGCAGGACA ACTCAAAGCT
19901 GGGAAGAATG GGAGGGAGCT TCCAGGTCAT AGGTGGATTA AAAACTTTTC
19951 TGATTGGCAA TTGATTGAAA GAGTCTATCT GAAGACCTGG AATTAGTGGA
20001 AGGGAGTGTC TGGGTTAAGA TAAGGGGTTG TGGAAATGAA GGTTTTTATT
20051 ATGCAGATGA AATCTCCAAG TAGCAGGCCT CAGAGAGAAT AGATTGTAAA
20101 TATTTCCTCT TATCGGATTT AAAAAGGTGC CAGACTCTTA GTTAACTTTT
20151 TCCTGGATCA GGAAAAAGCC TTGGAAAAAG AAGGGAATTT TCTTCAGAAT
20201 GTAGATTTTC CCCACAAGAG ATACCTTTGC AGGACTATTT CAAGATATGG
20251 ACAAAGAAAC ATGATTTGGG GTAAAATATT TTGATTCCTT TCAGGCCTGC

FIGURE 3G

20301 TATCTGTCAT GTGATGTTAT ACTAGAGTCA GGCTGGACTT TGGTATCTTA
20351 TTGCTACAAG GAGTCTGCTT TGTCAGTCTT AAGGTCTGTT TTAATGTTAA
20401 TGCTGGTCAA CTGTGCCTGA ATTCCAAAGG GGAGGAGGAG TTAATGAGGC
20451 ATATCAGACC CTGCTTCCCA TCATGGCCTG AACTAGTTTT TCAGGTTAAC
20501 TTTGGAATGT CCTTGGCCAA AGGGAGGGTT TATGAGTTGG TTGGGGGGCT
20551 TAGAATTTTA TTTTTGGTTT ACACACTTTC TAGCAAAATA AATTTGTGCA
20601 CCTGTTTGGA AGACAATTTG GTGGCAATAT GTACCAAGAG ATTTTTAAAT
20651 ATCCTGTTTC TGGGACTTCT TCCAAGGGAA TAATTTGAAA TTTGGAATAA
20701 CGTAAATGCC TAAATAATTG GGAAATGGTT AAATTTAATA AAGCTTGGCA
20751 TGGCCATGGC CATGTACCTG AATATATCAT AAACATTTAT GGTTTTGAAG
20801 ACTTCTTGAT AACTTTGTTA TACTAAGCAA AGAAAATGGA ATTCTGAATT
20851 TTAAATACAT TGTGATCACG GTTATATGAA AAATATGTGT GGAAAGAAGA
20901 CAGGAAGGAA ATATATCAGA ATTTTAACAA TAGTTGTTTT AGGTGCTAAG
20951 ATTCTGGGTA ACTTTTTTCT CCCTTATTCA TTTTTGTATT TTCCAAGTTT
21001 TAAATCATGA GGTTGCAATT TGATAATCTC TACATCTGAG AGATTTTTAT
21051 AACATGACAA TTTCATCTCT TTGTGGAGTC TTTAAGCCAT AAAAAATATA
21101 TTTTAATGTG TAAATTTTTG GGAGGTGAAT TGTAAGTTTA AAAATCAGCT
21151 GATTTAGTTA CTTTATCAAC ATACAGTGTT TTGCTTTCTT CTAACACATG
21201 TATGCATCAA ATCTTGTGTT ATCCATTTTC ACATTTTTTC TTGCATGTCC
21251 ATGTCTTAAG ACTTTTCTTA CTCCAATAAA AAATCATGCT GATTTATTAT
21301 TTAATATAAT TTACTAGTTC CATGGAACTT GCTCGAACTT GTATTGGAAC
21351 ACCTTACTAC CTGTCCCCAG AGATCTGTCA GAATAAACCC TACAACAATA
21401 AAACGTAAGT TGCTGACTCT TAGTTTGAAA GTGTCAGTAA AATCTGATGG
21451 ATGACACTGA ATGAAGATTC CAGAAACTAA AATTCAAATC TCTTCTTTCT
21501 TTCTTATGGT ACTTTTGTAA TTTCATTTGC TTCATGTGTG AAATTGTTCT
21551 GGACCAAACT GAGGGTTGGG TTGCTATTTC TCGCGGTCCA ATACGAGATG
21601 CAGATGAACT GGGGAGGAAG AGAGTTTTTA TTTCTGTAAC CAGTACAGGG
21651 AGAAGGCCTG GAAATTATCA CCAGACCGAC TCAAAATTAC AAAGTTTTTC
21701 AGAGCTTATA CACCTTCTAA GCTATATGTC TATGTGTAAG TGTGCATTCA
21751 TTTAAAGACA TACTGATTAA CTCCTTTTAA TCTATAACTA AGGTCTGAGT
21801 CCTGAAGACT TTCTTCTGGA GCCTCAGTAA GCTTACTTAA TCTAAATGGG
21851 TCTAGGTCCT GGGGTGATTA CCCTTATTTT GTCTCCTGCT AAATCATGGA
21901 GGTTTAGGGA GTTCCTGCAG ACCTCCAATA AACTTGTTTG TGGAGGCCTG
21951 GGGAGTTTCT TCAGACCACC AATAAAACTT GTTTAATCTT AAAAGGCTCC
22001 TTGTTAAGAA TTCCTTCATT ATTTTGTCAT GGTTTAAGGC CCAGGAAAGG
22051 CCTAGGCAAA ACTCTTGGTG GGCTTTTGTT ACATTACAGC CTTTGTATAA
22101 GGGCACTGGC TTTTTTTTTT TTATTTTTTG AGATAGAGTC TTGCTCTTGT
22151 CACCCAGGCT AGAGTGCAAT GGCACGATCT CGGCTCACTG CAACCTCCAC
22201 CTCCCAGGTT CAAGCGATTC TCCTGCCTCA GCCTCCTGAG TATCTGGGAT
22251 TACAGGTGGC TGCCACCATG CCCAGCTAAA GTTTTGTGTT TTTAGTAGAG
22301 ATGGAGTTTC ACCATGTTGT CCAGGCTGGT CTCAAACTCC TGACCTCACG
22351 ATCTGCCTGC CTCAGCCTCC CAAAGTGTTG AGATTACAGG TGTGAGCCAC
22401 TGTGCCTGGC TGGGCACTGG CTTTTTAAGC TTTTAATATT TAACTTCACC
22451 ACTCAGTTAG TATAGAAACA GTTGTGATGG AGGCCTGCAT TGGTAAGACC
22501 TGGCCTGCCA CAAAATGGGG ATCCCAGTGA CTATCTCTGA GCAGTGTTAC
22551 CTGAAGGTTT CAAACTTGTT TAGAAGAAAG CCATTTCTCT TCATTTAAAG
22601 ATACAAGTGG TATAAAAAAT AACATCGAAA ATTGCAGTCA CTGTGATGTC
22651 CATTTTTGTA TTATATGTTC ATATCTTTGA AGCACTGTTT AGTCTATTGC
22701 AAGAAAGATT GAAGAGGATG AAGTAGAAGA CAATGTGGTC TGGTGACCGC
22751 TCACTGGATT AGGAGCTAGG AATCCTAGTC TTGGCTCAGT TGCTAACTTG
22801 ACCAAGTCAG TTGACCTCTG TGGGCTTCAG TTCCCTAACT CATAATAATG
22851 AGAGTATTGA CTAGGTAATC TTCAAGGTGT CTTCCAGCTT TAAAACCCAG
22901 TTAGTTTTTA TGTATGTGAT ATCAGAGTCT GGTTCTCAGC AATAATTTTT
22951 TTTTTTTTTG AGATGGAGTC TGGCTCTGTC ATCCAGGCTG GAGTGCAGTG
23001 GTGTGATCTC GGCTCACTGC AATCTCTGCC TCCCAGGTTC AAGCAATTCT
23051 CGTGCCTCAG TCTCCCAAGT ACCTGGGACT GCAAGCACGC CCCACCATGC
23101 CCAGCTAATA TTTTGTATTT TTAGTAGAGA TGGGGTTTCA CCATGTTGGT
23151 CGGGCTGGTC TTGAATTCTT GACCTCAGGT GATCTGCCCG CCTCAGCCTC

FIGURE 3H

23201 TCAAAGTGCT GGGATTGCAG GTGTGAGCCA CCGCACCTGG CCCTCAGCAG
23251 TAATGCTAAT GTATACTGCA AGAAAAGGTG AAGAGGAGCT TTTGCTTCCT
23301 ATAAGGAGAA GGAAAAAAAT TTCATTTTTC AAAGCTGGCT GCCATTGAAC
23351 AAGTTGGCGA TAAGGAAGAT TGAGTTCCCT TTGGAAGTTA ATTGTCCTTT
23401 TGTTTAGGAA AAAATGCCCA AGAGATACTT GGCTATTGGA CTTTGAAGGA
23451 GATAAATGGA AGGCAAAGCT CAGACAATAG AGATTTACAA AAAGAATAGT
23501 AAGAATTTCT CTGCATAATA AAATAACAGG GATTTTTTTT TTTTTTGAGA
23551 CATCCCCTGG CACCAAGGAG TTTGGCCTCA AGTTAGTTGT GCAGGAATTC
23601 AGGTAGGGTG TGTTGGACGG AAAGTAGGCT GTTCAGAGCA GGGCATGCCA
23651 CAGACAGCCT TGGGTCAGCT GCATTGTTTT GTTTGCTTGT ACTGCTTTTC
23701 AAGAATTTGA ATCAACATTT AAATGCTGCT GGATATGGTG GCTCATGCCT
23751 ATAATCCCAG CACTTTGGGA GGCTGAGGGG GATGATTGCT TGAGTCCAGG
23801 GGTTCAAGAC CAACCTGGAC AACATTGTGA GACCCTGTCA CTACATCCAA
23851 AAAAAAATTA AATATTGAAA GACTTTAAAA TATGCATAGT TTGTACCTCT
23901 GAAAATTGGA AGATCTTAGC AATAATCAGG TGGGTAGCCG CTGGCTCCAT
23951 TAGAGGACTG GTTCACCACA GTCCTCAATA TGCAGAGTGG TCTCAGGCCT
24001 GCAACTGGCC CCACCCAACC CCCAGGTGGC TGCAGTACTG CCTGAGCCCT
24051 GGGGGCATAT GAATTCTCTG CCCTGGCTGC AGAGGGTCCT CTGGGAACAG
24101 AAGAGAAGTT TGGGTCTGTG GAAGCCCTAG TAAAGACAAA AGTCTGTGTG
24151 GTGTGAAATG GTCAGTGAGT TTCTAGAAGG TCTAGAAAGT TCATGTTTGT
24201 TTCCTGGGTC AGGTGCAGGC GGCTCACACC TGTAATCCCA GCACTTTGGG
24251 AGGCCAAGAA GGGAGTATTG CTTGAGCTCA AGAGTTTGAG ACCAGCCTGA
24301 GCAACATGGT GAAACCTTGT TAATGAAAAA AAAAATTATT AAAAAAAATC
24351 CCACAAATTT GTTTCCCACC AATCTTACCG TCTATTGTAC TTACTACCAT
24401 CTTTTGTACT CAAACTTTTA GTATGAGTCT ATCTCTCTCT CCTTCTCTCT
24451 GACACACACA CACACACACA CACACACACA CACACACTCA TGCACAAAGC
24501 ATTGCTGCTA GAGGAGCCAT TTACCTCACT CCTCACTTTA ATGATTCCTT
24551 CTTGCTTTGA CTCCTTGACT TCTGATTAGA CATTTTTTGA TCTTTTAGAT
24601 TTAATTGTGC TTTTTGTTCT ATAAAATAAC TCCTCAAACC AATCACATAT
24651 AAATATTTAT GAAGTACTAA ATCTGTAAGG AGCAAAGCTC ATGATATATA
24701 TTTTAAGTAT ATTTTTAAAT GTTTATTGAG AATCAGATAC TATGTTTATC
24751 ACATAATATA ACTTTGGTTC TGTCAAAAGC CTTGAGTAGG ATATATCTTT
24801 CAAAATCAAC CAAATATTAC CTTTTGAGTC AAAACAAATC CATGTTTGAG
24851 TTCTGCCTGC CTCCTCCAAA TTGCTCAACA TTTCATCATA CATACATTGT
24901 TTTTGAGCAG GAAGCTGAAC TAAATATTAA GCCACCAGGT TGTAGCAAAG
24951 TTTGTGTGCC TTTCTTTGAC TAGAAATCTG ACAAACTACA AATGGTTTTC
25001 ATTTTACCTC TTATCTTCTA ATAAGAATTG ATGATATATC TGAAAGCATT
25051 TGTAAAAGCT GATCAACTTA CATAAAATTG TAAAGCGACA CAAATTTAAG
25101 GCACTGTAAG GATAAAAGCT TTTATTAAGA ATTATGGATA TTTTCTTGGC
25151 ATGTAAACTC TTATCTTCTT TAGGGATATT TGGTCTCTTG GCTGTGTCTT
25201 ATATGAGCTC TGCACACTTA AACATCCTGT AAGTATGCTC ATTGTCAGAC
25251 TAATCTTGAA TTATTGGAAT TGTAGAAAAG AAATTAACTT CTGGGAGAAA
25301 AAGGTTAATG TTTGGTTTTA TTAGATTGTT AAAAATTATA TGGATAAGCT
25351 ACTTAAAATA ATGATAGATG ACATGGAAAG CTGTCCAAGC AATATTATAA
25401 AGTAAAAAGT CCAAGTTGGA GAATAGTATG TGTAGCATAT TTCCATTAAA
25451 AATAAATTGT GTGGGCTTGG CGTGGTGGCT CATGCCTGTA ATCCCAGCAC
25501 TTTGGGAGGC TGAGGCGGGT GGATCACTTG AGGTCAGGAG TTGGAGACCA
25551 ACCTGGCCAA CATGATGGTG ACACCCCGTC TCTACTAAAA ATACAAAAAT
25601 TAGCCAGGCA TGGTGGCATG TGCCTGCAGT CCCAGCTAGT TGGGAGGCTG
25651 AGGCACGAGA ATTGCTAGAA CCCAGGAGGC AGAGGCTGCA GTCAGCTGAG
25701 ATTGCGCCAC TGCACTCCAG CCTGGGTGAC AGCGAGACTC CATCTAAAAA
25751 AAATAATTAA TTAATTAATT ACTGTATGAA TAGATACGTT CAGCAAAAGA
25801 AAAATGTACA TGGGCAAAGT TCATAGGAAA CCAGGCACAA GCTTTTAAGA
25851 GTCTTTTCCC AGAGGTCACA TGGGATGTGC CAAATCCTCC AGCATTGTTA
25901 CCCACGTCAC CTGTGAAATG TGATCTATAA GAAAGCTCAT CGGATATACC
25951 CAGTGCCCAG GATTTTTACT GGGGACTGGT CACATAGGCA CCCTCTACCT
26001 GGCATATGCC AAACTTCCAG ACTCCTGGAA AGAAAGCCCG TGTTCAGCAT
26051 AAACCATTTT GTTCACATAA ATAGCTGAGG CAAAGATAGC CACTCTTGAC

FIGURE 3I

26101 ATTCAGGGAA TGGTGGGAAT TCTTCTGAAA TCTTAGTTCC CAGACACCAG
26151 CCACGGGCCA ACATTGTAAG CAGGCCTTTC TGAGGAGAGC TTGCTACATC
26201 AACTCTTTTC TCCACAGCTG TCATCATTGT TATTAATTAT TGTCAAGGGT
26251 TGCACAGCCA GTGTCTGACC AAAATGTGTA CTCCATTGTT TTTTTGAGAT
26301 GGAGTCCCGC TCTGTTGCCC AGACTGGAGT GCGGTGGCAC GATCTCAGCT
26351 CACTGCAACC TCTGACTCCT GGGTACAAGC AATTCTCTTG CCTCAGCCTC
26401 CCGAGGAGCT GGGATTACAG GCACCCACCA CCACACCCGG CTAATTTTTT
26451 TGTATTTTTA GTAGAGTCAG GGTTTTGCCA TGTTGGCCAG GTTGGTCTTG
26501 AACTCCTGAC CTTGGGTGAT CTGCCCACCT TGGCCTCCCA GAGTGCTGGG
26551 ATTACAGGCG TGAGCCACCA TGCCCGGCCA ATGTGTACCT TTATTGCTAC
26601 ACCATGGAGT TGAATATTAT TATGTATAAA TAACTATTGG TTTCATACAA
26651 TAGAAGATTT CTGGTCTATG AAGCATTTTA GAGGAAATTA AACGATGTTT
26701 ATGTTAATTT TAAAAAGCAA GAGATAAAAT TTCATATCAA TATGACCTCA
26751 ACTTTGTAAA ATAAACATCA TTTTTAAAAG AGATCAGAAG GAGCTATACC
26801 TCTGAGTGGT AAAATTATAC ATATTTTCCC CTGTCTTTAT AACTTCCTAT
26851 ACCTTCCAGT TTTTTTATTA TGAGTAAACA TTATTTTGAT AATAAGACAG
26901 AATTAAAACA AAATAAAAAC TTGTTTTAAA TAACATGGCA TCTTGTTGAA
26951 TAACTGCAGT ATCTGCTCAT GAAAGATTAG TTGATGAAAA CAATTTAAGG
27001 TGGACCACAG TGCTTCTTTT TTATTTTTTG ATTGAGACAG GGTCTCACTC
27051 TGTCACCCAG GCTGGAGTGC AGTGACGCAA TCACGGCTTA CTGCAGCTTT
27101 GACCGCCTGG GCTTAGACAA TCCTCTTGCC TCAGCCTCCC AAGTAGCTGG
27151 GACCACAGGC TCATGCCACC AAGCCCAGCA AATGTTTAAA AACCATGATT
27201 TGGAGAGATG AGGTCTAACT ATGTTTCCCA GGCTGGTCTT GAACTCCTGG
27251 GCTCAAGTGA TCCTCCTGCC TTGGCCTCCC AAATTGCTGG GATTACAGGT
27301 GACCCTAGTG CTTCTAACTA CAATTTAAAA ACATTGTTTT GCTTCTTGGT
27351 ATATTTGTTA CTTTAACACT TTTATTATTT GTTACTTTAG TAACTTTTCT
27401 CTGATTTAGT GTCATTTCTC CTTGTCCTTT CAGTTTGAGG GTAACAACTT
27451 ACAGCAGCTG GTTCTGAAGA TTTGTCAAGC ACATTTTGCC CCAATATCTC
27501 CGGGGTTTTC TCGTGAGCTC CATTCCTTGA TATCTCAGCT CTTTCAAGTA
27551 TCTCCTCGAG ACCGACCATC CATAAATTCC ATTTTGAAAA GGCCCTTTTT
27601 AGAGAATCTT ATTCCCAAAT ATTTGACTCC TGAGGTAAGT TTTGAGGTGA
27651 CTGTTTGGAT TTTGGCAGAG ATTTTGGGTT GCAGGTCCTT GACACGTGTG
27701 TTCGGTTTTA GGTCATTCAG GAAGAATTCA GTCACATGCT TATATGCAGA
27751 GCAGGAGCGC CAGCTTCTCG ACATGCTGGG AAGGTGGTCC AGAGTAAGTG
27801 TGACTTTGGC ATGCAATCAA AAGTATTTAT TACACATGTC TCACACAGAG
27851 AGTAATGCAA GGAAATTTCA CCAAACATAT TGAAAGTGGA CATTTTAAAA
27901 AATACAAGCA GTATAAGCAG GAGAAAAATC ATCTTGTCAA ATGGCAACTA
27951 GTGAGTGTGC CTGAAAGTTG TATATCTAGC TCATGCATGA CCTGCAGGGT
28001 TCCTTCTCGT TAGTCAGGAA ACCTCCATGA AGCAGAGGAC ATGCTAATAG
28051 AGATGCTTGA AGAGGTTGAG CCCAAACTTA ACTTTTGTGT AGTGAAGGGA
28101 CAGAGTGGGA GAAGGTTGCA GATAGACATG GATGATGAGA TGAAACTTAT
28151 TTTTCTAAAA GAGGATAGAC TGGCAATTAA GAATTCTGTT GCAAAGGACC
28201 ATTGGAGCTG AAGTTAGGAT CTTGGGGCCT AATTGATAAC AGTAAGAACT
28251 GTTACTTTGT GGTTCCCAAA GAAGGCAGGA GATATTTTAT GGTAGTAATA
28301 AATACAGAAA ACTTTTTTTT TTTTCCGAGA CGGAGTCTCG CTCTGTCGCC
28351 CAGGCTGGAG TGCAATGGCG CGATCTCTGC TCACTGCAAA CTCCACCTCC
28401 CGGGTTCATG CCATTCTCCT GCCTCAGCCT CCCGAGTAGC TGGGACTACA
28451 GCCGCCCATC ACCACTCCCG GCTAATTTTT TGTATTTTTT TAGTAGAGAC
28501 GAGGTTTCAC TGTGTTAGCT AGGATGGTCT CGATCTCCGG ACCTCGTGAT
28551 CCGCCCGCCT CTGCCTCCCA AAGTGCTGGG ATTACAGGCG TGAGCCACCG
28601 CGCCAGGCCG GAGAAAACTA TTTTAGTCCT GGTGTCAAGA ATCAGCTAAG
28651 CTGTGTGTCA GAGGGAGGGG TACGTTAAGA AAGAGAAAAT TACTAATTCA
28701 TTTGATGCTG TGAAAGTCAA AGCCCCAGAA TTTAGCTGTA ACTGAATGCC
28751 TGGACTTACA ATATCAGGAG GAGCAGAAAG CCTCTCAAAG GAATCCATGA
28801 CAGGGAAATG TTATCCATTG AGACAGAGAT TCTAAAATCA AGGAAAGTTA
28851 AAGAGAAAGT GAATGAGCCT CTTTGCCATT TAATTTGACT AACATTGTTG
28901 TATACCAGTC TAGATTGAGA ATGTTTAGAA AATAGACAAG TACAGAGTAT
28951 GGGACTGTGT ATTGTCCATA TTTCTAATCT AGGTAAGATA GGAGAACAAG

FIGURE 3J

29001 AACAATTTTT TTTTTATTGA GATGGGGTCT CACTGTGTTG CCCAGGCTGG
29051 TCTCGAACTC CTGAGCTCAA ACAATCCTCC TACCTTGGCC TCCCAAATTG
29101 CTGGGATTAC AGGTGCGAGC CACCTTACTC AGCCCAAGAA CAAATTTTGA
29151 TGGAGATAAA GACAAGCATT AGAAGATCTA CTCATACCTC AGTCCTGGCA
29201 CTTTGGGAGG CCAAGGAGGG CAGGTCACCG GAGGCCAGGA GTTTGATGCC
29251 AGTCTGGCCA ACATGGCCAA ACCATGTCTT TACTAAAAAT ACAAAAATTA
29301 GCTGGACCTG GTGGCCCATG CCTGTAATCC CAGCTCCTTG GGTGGCTGAG
29351 GCACAAGAAT CGCATGAACT CGGGAGGTGA AGGTTGCAGT GAGCTCAGAC
29401 CCTGCCACTG CACCGTAGCC CGGGTGACAG AGTGAGACTG TCTCAACAAA
29451 AAAAAAAGAG AGAAGATCTA CTCATAAATT CCAAACAATG TGGCATGAAT
29501 GGAGTGGCCT GATAACCCAA GCTCTAATGA CCAAATTTAA TAACTTTTAT
29551 TATTACCCCA TACATATTGT TTCTGTAAAT GTTAATATTA ATTTCTATTT
29601 TTCTGAAAAA AAGTGATGTT ATATATTACT AGAAATATGC AAAGGGACTC
29651 TGAAAAAATG GTTTTTTTCA TTTAAAGAAA TTGCATATTA ATTTTTCATC
29701 AGTACTCTCA CTGTGTGTAA AATATCTCTG GCTAAAAAGT AAACTTACTG
29751 TGTTATGAAA TGTAGCTTAT GTTTATACTC TTACAAGTAT CAGTATTAAT
29801 GGTGTACAAT TTTTAAAAAA TTGAAGCTGT TTTATTTTGG TTAATTAAGA
29851 GTGTAAAATA CAAAAAGTGA GATTCCAGGG AAAGTGCCCA CCAAGATCAA
29901 GGATATCTGT GCCAATTAAA AGGAATGCTA TATTGCATAG AAATGAATGG
29951 AGACCACCAG CTGGAGCCCA GAAGGCCAGA TCTGTAAGTC ATTCTAAACC
30001 CTCCTTTGTG TTTTTTAGCT ATGGTATATG CTTTTTGTTT GTTTGTTTGT
30051 TTGTTTTGAG ACGGAGTCTC GCTCTGTCGC CAGGCTGGAG TGCAGTGGCG
30101 CGATCTCGGC TCACCGCAAA CTCCACCTCC CGGGTTCAAG CAATTCTTCT
30151 GCCCCAGCCT CCTGAGTAGC TGGGACTACA GACGTGTGCC ACTATGCCCA
30201 GCTAATTTTT GTATTTTTGG TAGAGATGGG GTTTCACCAT ATTGGCCAGA
30251 ATGGTCTCCA TCTCTTGACC TCGTGATCCA CCTGCCTGGG CCTCCCAAAG
30301 TGCTGGGATT ACAGGTGTGA GCCATGGCGC CCGGCCCCGG CTAATTTTTA
30351 TACTTTTAGT AGAGACAGGG TTTCACCATG TTGGTCAGAC TGGTCTCGAA
30401 CTCCTGACCT TGCGATCAGC CTGCCTCGGC CTCCCAAAGT GCTGGTATTA
30451 CAAGCATAAG CCACTGCACC CAGCTGTTAT ATTCTTTTTC TTTAATTTTT
30501 TAATTAAAAA AAAAATTTTT GTGGGTACAT AGTAAGTGTA TATATTTATG
30551 GGGTATATGA GATGTTTTGA TACAGGCAAG CAATGTGAAA TAAGCACATC
30601 ATGGAGAATA GGGTGTTTGT CCCCTCAAGT ATTTATCCTT TGAGTTACAA
30651 ACAACCCAGT TATACTCTGT AACTTATTTC AAAATGTACA ATTAAGTTAC
30701 TATTGACCAT AGGCAGTCTA TTGTGCTATC AAATAGTAGG TCTTATTCAT
30751 TCTTTTGTTT TTTTAACCCA TTAAGCTATG GTATATTCTG ACAGACCTAT
30801 CTGCACATGT TCATGAGGTA CAAGCTTATT GTTTGGAGTC CACAAATTTT
30851 GTACTTAAAA TGAAGTATTC TGTACTGAGC ATTATAATGG TATTTTGTTG
30901 GACAACTTCT AGTTTTTATA TTTTATGAAA CAATGCTGTA TGCTCTTATA
30951 AGTATACTTT AGGCTTAATT TTCTTTTTAT AACTGAAATT CTTCTAATTT
31001 CTAATAAATA AGATTTTTCT GTATAGGAAA AGTGAGTAAC ATAGCAACAG
31051 AAAACACTCT GCATTTAATA TTCTTAATTC TAACATATTA TGTATAGGAT
31101 TGAGAAGTTT TTATGATATA ATAATTGATA TTTCCCTAGT GATTCTTTGT
31151 GTTTAATTAT TTGAATTCAC TTCAGCAGAG TGTTGAATCT TTTAGGTCAT
31201 ACTAGTGAAA TGCTTCTGGT ATGTAAATGA TAAAATGGCT ACTGTCTTTT
31251 AATTAAAGAA TTGTATTTTT AAAGAAGGCT CATGGTTAAA TTAAGAACCA
31301 TTTGGAAGTG TATTTACTAA GTGTTTACTT GATATATAGA CATTTTAGAA
31351 AATGTGTTGG TATATAAACA TTTTTTTAAA AACCGATTGT TTAAGTTATT
31401 GCCCTTCATT TGATAAAGGG CTTTATTTAT TTATTTATTT ATTTATTTAT
31451 TTATTTATTT ATTTATTTGA AAGAGGGTCC TGCTGTGTCA CCCAGGCTAG
31501 AGGGCAGTGG CATGTCTCAG CTCACTGCAG CCTGGATGTA TTAGTCTGTT
31551 CTCATACTAC TATAAAGAAC TGCTTGAGAC TGGGTAGTTG ATAAAGACAA
31601 GAGGTTTAAT TGGCTTACAG TTCTGCAGGC TGTACAGGAT GCATTGCTGG
31651 GGAGGCCGCA GGAAACTTAT AATCATGGCA GAAGGGGAAG CAGGCTCATC
31701 TTAAATGGCC AGAGCAGGAG AAAGAGAGCA AAGGGGGAGG TGCTACACAC
31751 TTGTAAACAA CCAGATCTCT GGAGAACTTA CTATCACAAG AACAGTAAGA
31801 GGGAAATCTG TCCCCATAAT CTAATCACCT TCCACCAGGC CCCTCCTCCA
31851 ACATCAGGGA TTACAATTCA ACATGAAATT TGGGCAGGGA CACAAATCCA

FIGURE 3K

| | | | | | |
|---|---|---|---|---|---|
| 31901 | AACCATATCA | TTCCACCTTT | GGCCCCTCCC | AATTCCCATA | TCCTTCTCAC |
| 31951 | ATTGCAAAAT | ACAATTATCC | CTTCTCAACA | GTCCCCCAAG | GCTTAACTCA |
| 32001 | TTTCAGCATT | AACTCAAAAG | TCCACAATTC | AAGGTCTCTC | TGAGACAAGT |
| 32051 | CAAGTCCCTT | CCACCTGTGA | GGCTGTAAAA | TAAAAAACAA | GTTAGTTACT |
| 32101 | TCCAAAATAC | AATGAGGGTA | CAGGCATTGG | GTAAATACAC | CCATTTCAAA |
| 32151 | AGGGAGAAAT | CAGCCAAAAC | AAAGGGTTTA | TAGACCCCAT | GCAAATTCAA |
| 32201 | AACCTAGCAG | GGCAGTCATT | AAATCTTAAA | GCTCCAAATT | CCTTTGACCC |
| 32251 | CATGTCTCAC | ATCCAGGGCA | TACTGGTGTG | AGGAGTGGGC | TCTCAAGGCC |
| 32301 | TTGGGCAGCT | CTGCTCCTGA | GGCTTTGCAG | GCTACAGCCC | CTGCGGCTGC |
| 32351 | TCTCACAGGC | TGCTGTTGAG | TGTCTGCGGC | TTTTCCAGGT | GCGTGGTGCA |
| 32401 | AGCTGTCGTT | CAATCTACCG | TTTTTGGAGT | CAGGAGAATG | GTGGCCCTCT |
| 32451 | TCTCACAGCT | CCACTAAGCA | GTGCCCCAGT | GGGGACTCTG | TGTGGAGGCT |
| 32501 | CCAATGCCAC | ATTTCCCCTC | TGCACTGCCC | TAGTAGAGGG | TCCCCCTGAA |
| 32551 | ACAGGCTTCT | GCCTGGACGA | CTAGGCTTTT | CCATACATCT | TCTGAGATCT |
| 32601 | TGGTGGAGGC | TCCCACGCCT | CAACTCTTGC | ACTCTGTGCA | TCTGCAGACT |
| 32651 | TAACACCATG | TGGAAGCCAC | CAAGATTTAC | GGCTTGCACC | CTCTGAAGCA |
| 32701 | ATGGCCTGAG | CTGTACCTTG | GGCCGTTTTA | ACCATGGCTG | GAGCTGGAGC |
| 32751 | AGCCACAATA | CAGGACACCA | TGTCCTGAGG | CTGCACAGAG | CAGTGGGGCC |
| 32801 | CTGGGCTTGG | TCCTCAAAGC | CATTCTTCCC | TCCTAGGCCT | CTGGGCCTGT |
| 32851 | GATGAGAGGG | GCTGCCTCAA | AGGTCTCTGA | AATGCCTTCA | AGGCATTTCC |
| 32901 | CCCATTATCT | TGGCTAACAA | CATTTGACTC | CTCTTTATTT | TTGAAAATTT |
| 32951 | CTGCAGCTGG | TTTGAATTGC | TCCCCAGAAA | ATGGGTTTTT | CTTTCTAGGC |
| 33001 | TGCAAACTTT | CCTAACTTTT | ACACTCTGCT | TCTCTTTTAA | GTATAAGCTC |
| 33051 | TGGTTTTACA | TCATTTATTT | GCTCACAAAT | ATGACCATAG | GGTGCTAGAG |
| 33101 | CAGCCAGGCC | ACATCTTGAA | TACTTTGTTG | CTTAGAAATT | TTTTCTGTCA |
| 33151 | GACGCCTTAA | ATCATCACTC | TCAAAGTTCA | AAGTTCCACA | GATCCCCTAG |
| 33201 | GGTAGTGGCA | CAATGCCTCC | AACCTCTTTG | CTAATTCATA | ACAAAAGTGT |
| 33251 | CCTTTGCTGC | ATTTCTCAAT | AAGTTCCTCA | TCTCCATCTG | AGACCTCCTT |
| 33301 | AGCCTGGACT | TTATTGACCA | TATCACTATC | AGCATTTTGG | TCACTATGAT |
| 33351 | TTTAAGAAGT | CTCTAGGGCA | TTCCAAACTT | TCCATCATCT | TCCTATCTTC |
| 33401 | TTCTGAGCCC | TCCACGCTCT | TCCAACCTCC | GCCCATTACC | CAGTTCCAAA |
| 33451 | GTCACTTTCA | CATTTTCAGG | TATCTTTATA | CAATACCCCA | CTCCTGGTAT |
| 33501 | CAATGTACTG | TGTTAGTCCA | TTCTCATACT | GCTATAAAGA | ACACCTGAGA |
| 33551 | CTGGGTAATT | TATAAAGAAA | ATACATTTAA | TTGGCTCACA | GTTCTGCAGG |
| 33601 | CTGTACAGGA | AGTATGGCTG | GGGAGGCCTC | AGGAAATTTA | TAATCATAGC |
| 33651 | AGAAGGGGAG | GCAGGCTCAT | CTTACATGCA | GGAGGAAAAG | AGTGAAGGGG |
| 33701 | TAGCCGCTAC | AAACTTTTGA | ACAACCAGAT | CTCATGAAAA | CTCACTCACT |
| 33751 | ATCACAAGAA | CAGCAAGGGG | GGAATCTGCC | CCAACGATCC | ATTTACCAGG |
| 33801 | CCTCGTCTCC | CAACATTGGG | GATTACAGTG | CAACATGAGA | TTGGGCAGAG |
| 33851 | ACACAAATCC | AAAGCATATC | ACTCGACCTC | CCAGGCTGAG | ACACAAATCC |
| 33901 | AAAGCATATC | ACTCGACCTC | CCAGGCTCAA | GTGATCCTAC | CGTCTCAGCC |
| 33951 | TCCTGAATAG | CTATACTACC | GGTATGCACC | ATGATGCCCA | GCTAGTTTTT |
| 34001 | ACTTTTTGTA | GAGTCAGGGT | CTCACTGTGT | TGCCCAGGCT | GTTCTTGAAT |
| 34051 | TCCTGGGCTC | TAGTGATATG | CCCGCCTCAG | CCTCCCAAAG | TGCTGGGATT |
| 34101 | ATAGGCGTGA | GCCACTGTGC | CCAGCCTAAG | GGCTTAATTT | TATTAAAGAA |
| 34151 | ATAAGAAAAG | TATGTTGTGA | TTCAGAGGAC | TCTTTATCAG | ACCTGTAGAA |
| 34201 | GGGAAAACAC | ATCTAAAAGA | TTTGAGGATG | AATTAAATTA | CGAACTGTTG |
| 34251 | AACACGCTGA | CATTTTTCCA | GTTCCTTGAA | AAGGTAAAAT | TGATTTCCAC |
| 34301 | AGGAACTACC | TCTGATATTC | CTATTACTGT | TGGGATGTTA | GAGAACATTT |
| 34351 | TAAAGAAAAT | GTTTATTGCC | TTTCAATACT | TTTCTATATT | TTTTACCACT |
| 34401 | TTTCAACAAG | TCATTAGTAG | CATTTTCTTC | TAGGTTGTAT | ATAGGTGAAA |
| 34451 | TTGTAAAACA | AAGAAAACTA | CTTCTTGTTT | TAAAAGATTT | TAAAAATAGG |
| 34501 | CAGGTGCAGT | GGCTCACGCC | TATAATCCAA | CACTTTGGGA | GGCTGAGGCA |
| 34551 | GGAGGATCAT | TTCAGCCCAG | GAGTTCGAGA | CCAGCCTGGT | CAACACATTG |
| 34601 | AGACCCCACC | TCTACAAAAA | GTAAAATTAA | AAAAAAAATT | TTTTGTTTTT |
| 34651 | TACTGGACAC | AGTAGCATGT | GCCTGTAGTC | CCAGTTACTT | GGGAGGATGA |
| 34701 | GGCAGGAGAT | CCCTGGATCC | CAGGAGTTTG | AAGCTGCGAT | GAGCTATGAT |
| 34751 | CACACCACAG | TCCTGCAGGC | TGGGTGACAG | AGTGAGATCC | TGTCTCAGAA |

FIGURE 3L

34801 TTTAAAAAGA AAAGAAAATA TTTTAAAAAT AAACATATAA TTTGTATTTA
34851 GATTAATGAA CTAAATTTTA TACATTTACT TAAATATTTA AATAGAACTA
34901 TATGAAAGTG CCATTTTTCT AGATTAATTA TGGTCAATTC TGGGCAATTT
34951 CTTTTTTTGA GACGGAGTCT CACTCTGTCA CCCAGGCTGG AGTGCAGTGG
35001 TACGATCTTG GCTCACTGCA AGCTCCGCCT CCCGGGTTTG TGCCATTCTC
35051 CCGAGTAGCT GGGACTATAG GCACCCGCCA TCACGCCCAG CTAATTTTGT
35101 TTTTGTGTTT TTAGTAGAGA CGGGGTTTCA CCTTGTTAGC CATGGTGGTC
35151 TCGATCTCCT GACCTCGTGA TCCGCCTGCC TCAGCCTCCC AAAGTTCTGG
35201 GATTACAGGC ATGAGCCACT GCGCCCAGCC AATTATGTGC AATTTCATAT
35251 GGTCCAATCT AACATATATG TGAACCATAT AGCAGTAAAA ACAACAAAGA
35301 ATATAACATG TTACCTCTTT ACATGAGGAC ATTTTGGTTT TAATTGTTCT
35351 TGTTATTCAT ATTCCCAACT ATTAGTTCCT AGGTCTTTCC AGTAGTTTTA
35401 TCTTTTTTTC TCTTTTTATT ATTAACTGTA AACTGTAAAC TAGACAGAGT
35451 TGCCACGCTT TAGGTTAAAT TGACCCCACT TTGCTCTTTA GCAAGAAGGT
35501 CTTGACTGGC TTTTATATCT TAATTTGATC TGTTTCTTGT CTTCTAGCTC
35551 AGTGGCTTCT ACTCAGTTGG AAGATAAACT GTCATTTCTG GTTCTCCTAT
35601 TCTCATTCTG TTCTGGTTGG GAAGGGTGGT GAGGGCTGGG ATGGTGATAT
35651 GCCCATCATG GCTGTTATAT GACCTTTTTT AATATTTTCT CTGGAAGAAT
35701 GATTCTGATT CAGCATCTTC TTTCCTTTAA GTCATGATGC CATTTTGCAT
35751 TTAGTCAATT TATCAGAAAC TAAAAATGTT GCAAATCCCC ATATGTGTGA
35801 GTTTCACTAT GCTTTTTATT TCCCTGTAAA GTATGGTAAG GTATAAATGA
35851 GTTTATGAAA AATAGAAAAC AATAATTCTG AGTTTAGTTT TGGATCTTGG
35901 GTTGCCTGGG CATACTCACT AGCTAAGTAT TTTTCACATA CTAGCCATGA
35951 AGTATGCATG ATTCATATCC ATACCTTAGC AAAATTGTAA ACCACTATAC
36001 TATCTAGTAC TTAGGTCTTT TTGTACTCTA GGATTTGGGG ACTCTTAAGA
36051 TTATTCTGGA AAAAAAAGTA TAGAAGAAAA ACAGCAAAAA TACACCTTCA
36101 GTGCCTTATC TTAGCTATGG TCACTGTTAT ATTGTCAAGT ATTATAAATT
36151 TGTATTATGG TTTTTTTTTT TGAGATGGAG TCTCGCTCAC ATTGTGCAGG
36201 TTGGAGTGCA GTGGCATGAT CTCAGCTCAC TGCAACCTCC ACCTCCTGGG
36251 TTCAAGTGAT TCTCCTTCCT CAGCCTCCCA AGTAGCTGGG ATTACAGGCG
36301 TGCGCCACCA TGCCTGGATA ATTTTTGTAT TTTTAGTACA GACGAGGTTT
36351 TGCCATGTTG GCCAGGCTGG TCTTGAACTC CTGACCTCAG GTGATCCACC
36401 CGCCTCAGCC TCCCAAAGTG CTAGGGTTAC AGGTGTGAGC CACTGCACCC
36451 AGCCTGTATT ATGGTTTTTA AAAACATCCC CTCTTGTTTT CTTCAGATAA
36501 AAATGATAGA AAGACCCAAA ATTGCTGCTG TCTGTGGACA TTATGATTAT
36551 TATTATGCTC AACTTGATAT GCTGAGGAGG AGAGCCCACA AACCAAGTTA
36601 TCACCCTATT CCTCAAGAAA ATACTGGAGT TGAGGATTAC GGTCAGGAAA
36651 CGAGGCATGG TCCATCCCCA AGTCAATGGT AATATTGTGG TCTAGCTTAA
36701 GCTTTGGTTA ATCTAAAAAT ATCTTTATAT ATTAACATTT ATTATTCTGA
36751 AATCCAAATT CTCCTAACAC AAATAATCCA AGAAGAACTT TCCAAATCTT
36801 CATTTTAAAC ACATAGTTCC CTTGACCTTT TTCTTTTGTT TGCTTTTGTA
36851 GACAGTCTCA CTCTGATGCC TAGGCTAGAG TGCGGTGGCG CAATCTCAGC
36901 TCACTGCAAC CTCTGCCTTC TGAGTTCAAG CGATTCTCGT GCCTCGGCCT
36951 CTCCAGTAGC TGGGACTACA GGCGTGCACC ACCATGCCCA ACTGATTTTT
37001 ATATTTTTAG TAAAGACAGG GTTTCACCAT GTTGGCCAAC CTGATCTTGA
37051 ACTCCTGACC TCAGGTGATC TGCCCGCCTC AGCCTCCCAA AGTGCTGGGA
37101 TTACAGGCAT GAGCCACCAT GCCTGGCCAT GTTAGTCCCT TCTTTCTATG
37151 TCAGCCCTAT ACCTGCTTGT TAGTTGGTTC TTCAAATTCT CAGGTACCCT
37201 CTCACCAGGC AGCCACTGAC CTCATGTGAT CCACCTGCCT TGGCCTCCTA
37251 AAGTGCTGGG ACTACAGGCA AGAGCCACTA TTCCCAGCCT TTCTTTCTTT
37301 TTTTTTTGTT AGAAAGATTT TGTTTTTATT TCCATCAGAA TGTCATATAT
37351 GTTACACAAA TCAAATCTGT TGACATCTCA AGCTTATAAC AATTACGTGT
37401 TCTTATAAAT TACGTGGGAA TTACATGTAC TGTGAGAAGT GTTGTAATTA
37451 TGATGTAATG TATATTATAA TTTAGCCTAC AGAAGTAACA AAGTCTTGTA
37501 ATTAAATAAA GCAATAAATG TGTTGATAGA TTATTACAAT TGATAAGTAA
37551 TTGATAAATT ATCTTCTTTT TCCTGTAACC CTTCTTCATC TCAAGTCTGA
37601 TCTAGCTTAT TTTCTTATTC ATAGAGCTGC TTAACTGTAG GCACAGACCC
37651 ATACCCTTGC TCTTTTAATA TTCTTTCTTC CTCCTACTAA ATTCCACTAT

FIGURE 3M

37701 ATGGCAGGTG AAAAAATAGT TGTGTATATT TCATTTCTCA AAGAGGTTAC
37751 TAATATGAAT CAATAATTGA ATCATTAAAA TCAAATGATC ATTTGAGACA
37801 TTTTGAGAAA TAAGATATAT TTCATTCGGC ATTTATGTTC TAGGGATTTT
37851 CAAAATATGG ACATGTTAGA AAGAAAATAG TATTCTTAAA TTGGTCTTAT
37901 GGTAGATTTT CAAAAAATTT ACTCCATAAT AGATTTCTGC AGATCTACAA
37951 TATTTTCAAA TTTTTTTCAC ACTGATGTTG ACATTCCTGT GTTCAGAATA
38001 ATTGACACCT AACAGAGGCC TGAAGACTTA AGTCTAAGAG TTCTATTTTA
38051 AAAATGTTTT GTCATCAATT TTTTTTGTTC AGGGTTAAGA ATTTGTTACT
38101 TTGGCGACTC TGATTGTTTA TTGTTGAAAT TTTGGATGAA TTATGAAAAA
38151 CACAAGATAC TATGGGATGG CAATCTCATT AATAGTGAAA ATGAGATAAG
38201 CAAGAATGAT AAGAGAATAA TTTCTTCAGA AACATATAAC GGGAAAAGCA
38251 TATGTTTTAT CTTTAAAGAT ATTGGGCACT GTTGTGGTTT TTATCGATCT
38301 TCATAACACA TTTTTAATTA TCTCCACAAT TATCAAAAGT TATGTCTTCT
38351 GTCCGTTCAA ATTGTAATAT CCATATTGGA CTCAATTAGT GAGGGACATA
38401 GATTTTACAG AAGAACTGGA GCAGCCACAA AACTCCCTTT CTCTTTTCTC
38451 AACCACTGGG AAAATATATC TTCCACTCTT TGTCTAGATT TGAGAGCTGT
38501 CAAGCTATCA ATTATTTTGA CCACATGTGA TTTTATATCT CCCAAGCTCT
38551 CACATGAAAC AGTAGGAAGG GTCCTTCTCT TTCCTGGATG CCCCTTTGAT
38601 GCCTGGTAAC CCCTCCTCTT TGTATACTCC CTCATCCCCA GCTTTCTGTC
38651 TGCTGGAGGT CCAATTACAG GCCATGGGAT GGAGGAAAAG GATTTTTTTT
38701 TTTTTTGAGA CAGAGTCTCG CTCTGTCGCC CAGGCTGGAG TGCAGTGACG
38751 CGATCTTGGC TCACTGCAAG CTCCGCCCCC TGGGTTCACA CCATTCTCCT
38801 GCCTCAGTCT CCAGAGTAGC TGGGACTACA GGCGCCTGCC ACGACACCTG
38851 GTTAATTTTT TTGTATTTTT AGAAGAGACA GGGTTTCACT GTGTCAGCCA
38901 GGAGGGTCTC AATCTCCTGA CCTTGTGATC CACCCGCCTC GGCCTCCCAA
38951 AGTGCTGGCA TTACAGGCAT GAGCCACCAT GCCCGGCCGA GGAAGAGGAA
39001 TTTGTATAGG ATTTGGGGGG TGGAGAGGGA ATAGGTAGAC AGAGAGATAG
39051 AGAATGTCTT TTGGACAGCC CCTGGGTGTT GGAATCATTT TTCTCATGAA
39101 GATATTGATA CATGTGCCAG TTAGGCTTAT GAGACAGATG AGTGCTACAA
39151 TTTACCCTCA TTTGATTCAA GAACTATCTG TGTGTCAGGC ACTTCACAGC
39201 CCTAATCTCT TCTAATCCTC GTATCAATTC CTGTGAAATG GTACCATGCC
39251 CACTTTACAG CTGAGGAACT AAGACTCAAA GACTTTAGCT TGTCATTTCA
39301 TCCTATTTCT AAATCCCTGA TTATTAACTT GCCTCTTTGT AAATTGGGGA
39351 TGCTTATCAT GATGTTCCTT CCTAAAGGAG TTATTTCTGA AATTACAGTT
39401 CTGTCTTTGG AGCCTTAGAA GTTACTCGTA TTCCAAAAAA CTTATGGTCT
39451 GAAATGCGGT TTTTATTTAG CAACCAATAA TTACAGAAAT GTTTTACAGG
39501 AAATTCTGCC AAAAAAAAGA TACATAAAAT GTGAGTATAA ACTTGAAAAT
39551 TGTTTGACTG GAATTGACTA AAATTGTGCT GGAAAAATAC CTTAAACATT
39601 TGGAGAGACA GCTAAACCAT TATTTCTTTC CTCATTAAGC ATTTATGTGC
39651 GGAGATAAAG GGATGGATGG AGGGACACAT TCTGCTCTCA GGGAGCTCAG
39701 TATGTGGTGC AGGAAACAGA TATGCAGCCA TTCTTTTTTT TCTTTTCTTT
39751 TCTTTTTTTC TTTTTTTTTT GAGATGGAGT CTCACTCTGT CACTCAGGCT
39801 GGAGTGCAGT GGTGCGATTT TGGCTTACTG CAACCTCTGC CTCCCTGCTC
39851 AGCCTCCCCA GTAGCTGGGA TTACAGGTGC CCACCACCAC GCCCCACTAA
39901 TTTTTTTTAG CAGAGACGGG GTTTCACCAT GTTGGCCAGG CTGATCTCGA
39951 ACTCCTGACC TCGTGATCCA CCCACCTCGG CCTCCCAAAG TGCTGGGGTT
40001 ACAGGTGTGA GCCACCACAT CTAGCCACTA TTGTTAAATC AGGAGCGACA
40051 ACCTGTACAT TAGACACCTA CACAAAGCGT GAGAACTTCT GGGTGTGGGT
40101 CTGTTTTCCT CCCCACAACA TATTATAGAG AATGGAAGGA CTGAATCTTG
40151 TCCTGAAGAA AAATCACTGG ATAAGAATAT TTTTCTGTTT AATCCTCTCC
40201 TGTATCCCCA CTTGTTACTC TTCATCCTTT TTTCCTTTTG ATTCCAAAAT
40251 TTTCTTTTCC AATGTAAAGA TTCTGTAACT GTGAACTACT TCTTGAACTT
40301 GGAACTTCAA GCCACTGGTG AATTGTGAAT CTCATTACTA AACTGAAAAT
40351 TACTCGTCAA ATTGGTGCCT AAGATTCGTT CAAGTTTCTA CTTAAGCTGA
40401 ACATTCTTAT TTTCTAAGGC CTGCTGAGTA CCTTCAGAGA AAATTTGAAG
40451 CTCAACAATA TAAGTTGAAA GTGGAGAAGC AATTGGTAAG TAAAATACCA
40501 AATATGGGAA GCAATTAGGA ATTTCCTAAT AGTTTTTCTG TTCACAGATT
40551 TTCAAGTCAA AGTTCATTCC ACCAGAAGGT CAAGAATACT CTCTACTAGT

FIGURE 3N

| | | | | | |
|---|---|---|---|---|---|
| 40601 | CCCCAGTTTT | TTTTGTTTTT | GTTTTTGTTG | TTGTTGTTGT | TGTTGTTTTC |
| 40651 | TGAGACAGAG | TCTCGCTCTG | TCACCAGGCT | GGAGTGCAGT | GGTGTGATCT |
| 40701 | TGGCTCACTG | CAACCTCTGC | CTCCCAGGTT | CAAGCAATTC | TCCTTCCCCA |
| 40751 | GCCTCCTGAG | TAGCTGGGAT | TACAGGCGCC | CACCACCACG | CCCAGCTAAC |
| 40801 | TTCTGTATTT | TTAGTAGAGA | CAGGGTTTCA | CCATGTTGTC | CAGGCTGGTC |
| 40851 | TCGAACTCCT | GATCTCGGGT | GATCCACCCA | CCTAGGCCTC | CCAAAGTGCT |
| 40901 | GGGGTTACAG | ACGTGAGCCA | CTGCACCTGG | CCCGAGTCCC | CAGTTTTTAA |
| 40951 | TAGCTAAATA | AAATAATGGG | AACAGGCTTG | AATCACCCCC | TTAGCAGTCC |
| 41001 | GGTTTCTTCC | TTGGCTCTAT | CTCTTCTGTG | GGACCTTGGA | CAGTTCATTC |
| 41051 | AGCCTATCTG | AGCCTTAATT | TCCTTTTCTA | TAAATGACAA | TTTTTAGAGT |
| 41101 | AGATGAGCTT | CAAATTTCCT | TGCAGTGCTG | TAGTGCTTTG | GTTCTATTTT |
| 41151 | GTTAAAGATT | CTGCTGCACA | TTAAAAAAAG | TGACAAGGGG | CCAGGTGCGG |
| 41201 | TGGCTCATGC | CTGTAATCCC | AGCACTTTGG | GAGGCCAAGG | TGGGCGGATC |
| 41251 | ATAAGATCAG | GAGTTCAAGA | TGAGCCTGAC | CAACATGGTG | AAAGCCCGTC |
| 41301 | TCTACTAAAA | ATACAAAAAT | TAGCCAGGCA | TGATGGTGCA | CACCTGTAAT |
| 41351 | CCCAGCTACT | TGGGAGGCTG | AGGCAGGAGA | ATTACTTGAA | CCCAGGAGGA |
| 41401 | GGAGGTTGCA | GTGAGCCGAG | ATCGCCCTAC | TGCACTCTAG | CCTGGGCGAC |
| 41451 | AGAACGAGAC | TCTGTCTCAA | AAAAAACAAA | AAAAACAAAA | ACCAACAACA |
| 41501 | AAAAAGTGAT | TAGGCCAGAT | ATTATGGCTC | ATGCCTGTAA | TCCCAGCACT |
| 41551 | TTGGGAGGCT | GAGGTGGGTG | GATTGCTTGA | GCCCAGGAGT | TCGAGACTAG |
| 41601 | CCTAGGCAAC | ATAATGAGAC | CTTATCTCTA | CCAAAAAAAA | CAAAAATTAC |
| 41651 | CCAGGTGTTG | TGGTGTGTGC | CTGTAGTCCC | AGCTACTGAG | GGGGCTGAGG |
| 41701 | CCGGAGGATT | GCTTAAGCTT | GGGAGGCAAA | GGTTACAGTG | AGCTAAGATT |
| 41751 | GCGCCACTGT | ACTCCAGCCT | GGGTGACAGA | GTGAGACTCT | GTCTTAAAAA |
| 41801 | AAAAAAAAAA | AAGAAAGGCT | GGGCTTGATG | GCTCATGCCT | GTAATCCCAG |
| 41851 | CACTTTGGGA | GGCCAAGGCG | GGCAGATCAC | GAGGTCAGGA | GATTGAGACC |
| 41901 | ATCCTGGCTA | ACACAGTGAA | ACCCTGTCTC | TACTGAAAAT | ACAAAAAATT |
| 41951 | AGCCGGGTGT | GGTGGCGGGT | GCCTGTAGTC | CCAGCTACTC | GGAAGGCTGA |
| 42001 | GACAGGACAA | TTGCTTGAGC | CTAGGAGTTG | GAGGCTGCAG | TGAGCCAAGA |
| 42051 | TCATGCCGCT | GTACTCCAGC | CTGGGTGACA | GAGTGAGACG | CTCTCAAACA |
| 42101 | GAAAAAAATA | TATATTTTTT | AATGCTTTAT | AATTAAGAAA | ATTCTACTAC |
| 42151 | TTACCACAAA | AAAAACTCCC | AAATACTGAG | TTTGCTTAGT | GATATAATTC |
| 42201 | TTATTTATAG | GAAAAAGTCA | ATGTCAAATC | AGAAGATGTT | TCCGAAATCA |
| 42251 | AAGTATGCAT | TATAAATTAT | TTCATTCAAT | AAATAGGGTC | TTCGTCCATC |
| 42301 | TTCTGCCGAG | CCAAATTACA | ACCAGAGACA | AGAGCTAAGA | AGTAATGGAG |
| 42351 | AAGAGCCTAG | ATTCCAGGAG | CTGCCATTTA | GGAAAAACGA | AATGAAGGAA |
| 42401 | CAGGTTAAAA | ACTGTTTAAT | TCCAGGGCTA | CCCTTGTATT | TCTTTGTATT |
| 42451 | ACTGTCTTTT | GTACTGTAAT | AGGGAGTTAC | TTCTATTTCC | TACAGTGCCC |
| 42501 | CTGAATATGT | CAACACCATG | CTGAGTGTTA | TAGGGGATAC | AGAGTTAGGT |
| 42551 | ATTTCACTTT | CTCAGATAAT | GCGATATGGC | TAAGTTCATA | AAGCTTTTCA |
| 42601 | CCTTGAGATT | CATAGAGTAA | CTGTCCATCA | GTAACAGGTT | TGGGATTTGT |
| 42651 | ATTAGTTTCC | TGGGCTGCTG | TAACAGAGTT | CAACAAACTA | GGTGGCTTAA |
| 42701 | CACAATAGAA | ATGTATTGTC | TCACAATTCT | GGAAGAGTGG | AAATAGAAAA |
| 42751 | TCAAGGTGTC | AGCAGGACCA | AGTGCCCTCT | GAAACCTGTA | GGGGAATCCT |
| 42801 | TCCTTGCCTC | TTCCTAGCTT | CTGGTGCGTC | ACTGGCAATC | TTTGGCATTT |
| 42851 | CTTTACTTGC | AGTCGCATCA | CTCCATTCTC | TGCCTTCATC | ACATGCTGTT |
| 42901 | CTTCCTGTGT | GTCCCTGTCT | TCACATGGCC | ATCTTCTTGC | AAGGACATCA |
| 42951 | GTCATATTGA | ACTAAGGGCC | CACTGGTATG | ATCTCATCTT | AAGTAGTCTC |
| 43001 | ATCTGCAGCG | ACCCTGTTTT | CAAATGGGGT | CACATTCTAA | GGCACTGGGG |
| 43051 | GTTAGGACTT | CAACATATCT | CTTTTTGGGG | AGGAACAAAC | TTCAGTGCAT |
| 43101 | AAGAGGGTTA | TATATAAAAG | TGGGATTTAT | AAAGTAAGTG | TACATCATGA |
| 43151 | ACACATTTGG | GTTATATATA | AAATTGAGCT | CTGTAGCTAA | AGCCACTGTC |
| 43201 | TCACAGGGAG | TGAAGTACTG | CAGCCAAAAC | ATAAGGCAGA | TTATCATCTT |
| 43251 | TAGGAGCAAC | ATATTTTTCT | AACCTTATTT | TATATTACAC | ACTTTTGAAA |
| 43301 | TTGTAGGCTG | CAGAAAGATT | ATTTTTGTTA | TGGTGTTCAT | AAACATTTAA |
| 43351 | AGTTTCTGGA | TTGGGTTTGC | TTTCCAGGAA | TATTGGAAGC | AGTTAGAGGA |
| 43401 | AATACGCCAA | CAGTACCACA | ATGACATGAA | AGAAATTAGA | AAGAAGATGG |
| 43451 | GGAGAGAACC | AGAGGTAAAT | TCATTCTTCT | AGGGGAAACA | TTGTTCTATC |

FIGURE 3O

43501 GATTTAGAGC TAACTAAATT GAGCTGGTAT TAAAAGTAAT GATTTCCTTA
43551 TAGAAAAGAT AAAGTTTTAT CATAGAGATA ATCATGTAGA CTTCTTTTTT
43601 AATAGGAAAG CTGTCAGACC TCATTGGAGC TTCAGTTTAT TATGGTTTAT
43651 GAGAGACTAC ACAAGATAAT AAGGATATCT GAGATTCTCA GGAATGGCTA
43701 TTATTAAAAG TACTTATTGA TTGTTTCCTT CATGAATCAC TCAATACATA
43751 TTTATTGAGT GGCAACTTTA GACAAGAGCT GGATTAGATG CAGAAAGTCC
43801 AAAATGAGTG TAAGTTCATG CCCAGAAGGT GGGAAAAAAA CAAACCCAAC
43851 ACACTAGCAT TTTTTCAACT CTCTGCAGGG TAAGGTTCTA AAGGCTATTT
43901 AAGGCAAAAT CTGAGTGCAG TTGAACTGAT TCTTAAAAAT CTCTTAAAGG
43951 CGCCACATTG GAAATTCATC CTTCCATCTC CCAAGAAGGT CTCTAGAGTT
44001 GGCACAGATC ACTGCTTCTT CAGAAGAGCT TCACATGAAA TAGCCAGCCT
44051 GTGTTTGGAA ACCATGTTGT AAGAAAGACA CATGGCTATT GAAACACTAG
44101 GAACACACTC AGTGCCCTGG AATGCTCTCC TAGGAGAAGC TTGCAGGCAC
44151 TGAGACAGCT GTCTCCCATC CCACATGCAC TTGGCCACAC ACTCATTGAG
44201 TAGAGCTACC ATGCTGCTGA AATTGATCTC TCTCTCTCTT TCTCCCACCG
44251 CAGTGCATAC AGATAAATTC ATATAAGTCA AATGAATGTA TGGTGCAATT
44301 CAGTTGTGTT TGCCAGGCCA TGAACTAGAG CTTTCACATA CTGTATTAGT
44351 CTGCTCTCAT ACTGCTAATA AAGACATACC CAAGACTGGG TAATTTATAA
44401 AGAAAAAGAG GTGTAATAGA CGCACAGTTT CACATGGCTG GGGAGGCCTC
44451 ACAATCATGG CAGAAGGCAA AGGAGGAGCA AAGTCATGCC TTACATGAAG
44501 GCAGGCAAGA GAGCTTGTGT AGGGGAACTC CTATTTACAA AACCATCAGA
44551 TCTTGTGAGA CTTACTCACT ACCATTAAAA TAGTATGGGA GAAACCACCC
44601 CGATGATTCA GTTATCTCCA CCTGGCCCCA CCCTTGACAA ATGAGGATTA
44651 TTACAATTCA AGGTGAGATT TGGGTGGGGA TACAGAGCCA AACCATATCA
44701 CGTTCATACT TTCTTTTATT TACCCCTGTA CAGAGAAGTT AAGTAGCTCA
44751 TCCAAAGTCA CGTAGCTATT ACAAGGCAGA CGAAATATTT AAATATCTGA
44801 CTCTAGGCTG GGCACGGTAG CTCATGCCTG TAATCCCAGC AATTTGAAAG
44851 GCTGAGGTGG GAGGATTGCT TGAGCCTAGG AGTTTGAGAC CAGCCTGGGC
44901 AACATAGGGA AACCCTAGCT CTAAACACAC ACACACACAC ACACACACAC
44951 ACACACACAC ACACACACAC ACACACACAC TCTCTCTCTC TCTCTCTCTC
45001 TCTCTCACTC TCTCTCTCTC TCTCTCTCTC TTTAAATTAG CCGGACATGG
45051 TGGTTTGCAC CTGTAGTCCT AGCTACTTGG GAGGCTAAAG CAGAAGGATT
45101 GCTTGAGCTA GGAGCTAAAG GCTGCAGTGA GCCATGATTG TGCCACTGTA
45151 CCCCAGCCTG GGATACAGAG CAAGACTCGG TCTCAAAAAA ATAAAGTAAA
45201 ATAAAATGAA AATCTGACTC TAAAACCCCT ACTCATGTTC ATGCCTGTAA
45251 TCCTAGCATT TTGGGAGGCC AAGGCAGAAG GATCGCTTGA GCCCAGGAGT
45301 TTGAGACCGG CCTGGGCAAC ATAATGAGAC TCCATATGTA CAAAAAATTT
45351 AAAAAATTAG TGGGTCATGG TGGCAAATGC TTGTAGTCCC AGCTACTCAG
45401 GAGGCTGAGT TGGGAGGCTG AGGTTGAAGC TGCTGTGAAC TGTGATTTTT
45451 CCACTGCACT CCAGCCTGGG CAACAGAGGG AGGCCCTGTC CCAAAAAATA
45501 AAAAAATACA ATTATAACCA CTATTCTTTC TGGCATATGC AGTTCTACTT
45551 ATAAATGGTT GGAATGACGA GACACATGTA TAAAACAATC ATAGAGTAAG
45601 CCCTGTAGGT GCACAGGAGC CAAGATGAGC AGAATGAGCA GGTAGCGGGT
45651 ATTTATGGAA GAAGTGGGTG GGGCCTAAAG AGTGGAATTT GGAGAGGCAG
45701 AGTTAAAGGA GGAGAGTGGG CATTCTGAAA GAACCATGCA AAGGTTGGGA
45751 CAGAGGACTG TGTGTGCTGG GAGGGGCAGC CTGGAGGTTG TTCTCTCTGG
45801 AGCAGAGGCC TGGCTCATGG GCAGCCTGGA GCCATCATCA GCCTTATGTC
45851 TAAGGCTGAT CTGGGATGGG CAGCCTGAGC CCTGCAAAAA TGGATAGCAG
45901 ACATTGGTCA GGCGCGGTAG CTCACGCCTG TAATCCCCAG CACTTTGGGA
45951 GGCTGAGGTG GGCGGATCAC GAGGTCGGGA GATCGAGATC ATCCTGGCTA
46001 ACACAGTGAA ACCCTGTCTC TACTAAAAAG CCAAAAAATT AGCCAGGCGT
46051 GGTGGTGCGT GCCTATAGTC CCAGCTACTT GGGAGGCTAA GGCAGGAGAA
46101 TGGCATGAAC TCAGGAGGCA GAGCTTGCAG TGAGCCAAGA TCGCACCACT
46151 GCACTCCAGC CTGGGTGACA GAGTGAGACT CCATCTCAAA AAAAAAAAAA
46201 TGGTGGATAT CAGACATTTC TACAGAGGCT ATGGAGGAAG GATTTGGGAA
46251 ATACTGAAGC TGTGGCGGGG AAAAGGAGCT ATAAAAAGGG TTCTGTCCAG
46301 CCATTTCATC ATTGATCGCG CATCAGCCAA GTAGCCTTCA GAGCTCACTC
46351 AGAACCAATC TTGTTGACTG TGTATAATTT GTGTTAAAGG AGAACTCAAA

FIGURE 3P

46401 AATAAGTCAT AAAACCTATT TGGTGAAGAA GAGTAACCTG CCTGTCCATC
46451 AAGATGCATC TGAGGGAGAA GCACCTGTGC AGGTAATGAT GGCTATGATC
46501 AGATGTGTGT GCTTGCAGTG TGTGTGCTCT ACCCCAAGTG GCTCTTACCC
46551 TTCTCTGTGC AGCAGAACCA CGTAGGGAAC TTTTTTTTTT TTTCTATGAG
46601 ACGGAGTCTC ACTCTGTCGC CAGGTTGGAG TGCAGTCGTG CGATCTTGGC
46651 TCACTGCAGT GTCTGCCTCC TGGGTTCAAG TGATTTCCTG CTTCAGGCTC
46701 CCGAGTAGCT GGGACTACAG GCATGCGCCA CCATGCCCAG CTAATTTTTG
46751 TATTTTTAGT AGAGACAGGA TTTCACCATG TTGGCCAGGA TGGTCTTTAT
46801 CTCTTGACCT CGTGATCCAC CAGCCTCGGC CTCCTAAAAT GCTGGGATTA
46851 TAGGCATGAG CCACCGCCTT TTTACCAGAA CTTTTAAAAA CTCAGATGCC
46901 TCTCTCTGCC CCAGATGGTC TGGGATGAGG CCCAGGCATT CTGTCTGCAG
46951 AAGCTTGCTG GGTGATTTAG TAAGCAGCCA AGTTTGAGAA CTGCTGCTAT
47001 TTAGTATAAG AACGTTCCAC TCTCTGGAGG GTCTAAGTCA GTGTATCAGA
47051 CACATTGGTC AGGAAATCTG AGTCAAGTTC TCTTCCATTT CAACCTTATG
47101 TTTTTGGTGG AGGTAAGAGC CTGGGCAGAG TTGAAATAAC AAATAAATCT
47151 CAAGAGAGTT TTTTTCCCTT CTGAGAAAAG ATAATGCAAT TATAATACAA
47201 GATGAATCTG TTGATTTCAA CCAATTCTGA GAATTATTAA ACCTGTGAAA
47251 TGACCTGATA AACAATGCTT TTATGGTTAC ATAAAATAAT TACATAAAAT
47301 GTTTTACTTT CCAAGGAGTT ATATTTATTT TGCGAATAAG AAGCCCAAGT
47351 GTGCTTTTAT TTTTGCTTAG TAAGAAGATT CTCAATGATT TGGCCCATAC
47401 TAAGAATTAT TATTATCTTT TTTTTTTAGA TGGAATTTCG CTCTTGTTGC
47451 CCAGGCTGGA GTGCAATGGC ACGATCTTGG CTCACCGCAA CCTCCGCCTC
47501 CCAGGTTCAA GCGATTCTCC TGCCTCAGCC TCCTGAGTAG CTGGAATTAT
47551 AGGCGCCTGC CACCGCGCCC AGCTAATTTT TGTATTTTAG TAGAGACAGG
47601 GTCTCACCAT GTTGGCCAGG CTGGTCTTGA ACTCCTGACC TCGGGTGATC
47651 CACCTGCCTC AGCCTCCCAA AGTGCTGGGA TTATAGGCAT GAGCCACCCC
47701 GCCTGAGCGA ATTATTATTA TCTTTATAAT TAGAGTAATT CTCTGTGTTT
47751 TAAATTATAT TTATTATTAG AGCTTGGTCC AGAGTCAACT AGAAATGGAA
47801 AATCCTCAAG GTATTATAAA CTTGTCATTT AAAGGTGCCA GTAGGATCAC
47851 AGTCACATTC CATAAAAACA CGGCTCAGAT GTTACAGACA TGTTTTTCTC
47901 TCACATTTTT TAACCTGGTT AGAGTAAATC CAGTGCCTTA AAGTTTTTAA
47951 TAAGTCAGGT AATTAAAAAT AAACCACTGG AAGCCTCAAA AAGTTTGTAT
48001 CAGGAATTGG GTGAATAAAA TCTTGTATAT TTTATGCAAG AGGAGTAACT
48051 TTGAAAGAAA ACACACCAAA ATGCCAATGG TGGTAATTGG TGGTATCTGG
48101 ATTGGTGTGA GTAGGAATGA TTATTGTCTC TCTACTTTTT AGATTTTTTA
48151 TAAGAAGGTT ACAGAACTTT TACTACAAAT ATGTATAATA AAGTATCCGT
48201 TCCTTAGTTC TGTCAGCACT CTAATCAATA TCTTCAAACA AAAAAGCCAT
48251 CTGAAAGACA GAAATGGTGG CACGAGACTA TAGTTCCAGC TATTTAGGAG
48301 GCCGAGGATC CCTTGAGCTC AGGAGTTTGA GACCAGCCTT GGTAATATAG
48351 TGAGACCCCA TCTCTAAAAA AAAAGAAAAG GCATCTGATA TTTCCTGAAG
48401 GCTCCTCCAG AGCAATCCAG CAGCAGATAC CTTTGCAAAC TTTTGTAAAG
48451 GAAATAATTA TCACTTAATT TGTCTAATTT TTGGATTTAG GTTTTAATTA
48501 TCTTTTTTGA AGGGAATATG CAGCTATATA ATAAGACACT TTAAAAAAGT
48551 CTCTACTTGT AGAGTTATCT TTCCAAAATA CTGATTTGAA CATTATTTCT
48601 CTACACGACA ATCAATGGCG ACTGCCATTT CTCTTAGCAT GGCATGCTAG
48651 ACTTTTGTGA GTTGTTCCTA ACAGAATGTT CCAGCCTCAT TGCTCACATT
48701 TCCCCCAAAC ATACCCAAAG CTCTAAATGT CTCAGATTAC CTTTTTTTTT
48751 TTTAAATGAC ATATTTTTTA TTTCTTTAAG TGATTTTTTT CACTGTGGTA
48801 AAATACATAT AACATCGCCT TTACCACCCT AACCATTTTT TTTTTTTTTT
48851 TTAATTGATC ATTCTTGGGT GTTTCTCGCA GAGGGGTATT TGGCAGGGTC
48901 ATAGGACAAC AGTGGAGGGA AGGTCAGCAG ACAAACAAGT GAACAAAGGT
48951 CTCTGGTTTT CCTAGGCAGA GGACCCTGCG GCCTTCCGCA GTGTTTGTGT
49001 CCCTGGGTAC TTGAGATTAG GGAGTGGTGA TGACTCTTAA CGAGCATGCT
49051 GCCTTCAAGC ATCTGTTTAA CAAAGCACAT CTTGCACCGC CCTTAATCCA
49101 TTTAACCCTG AGTGGACACA GCACATGTTT CAGAGGGCAC AGGGTTGGGG
49151 GTAAGGTCAC AGATCAANNN NNNNNNNNNN NNNNNNNNNN NNNNNNNNNN
49201 NNNNNNNNNN NNNNNNNNNN NNNNNNNNNN NNNNNNNNNN NNNNNNNNNN
49251 NNNNNNNNNN NNNNNNNNNN NNNNNNNNNN NNNNNNNNNN NNNNNNNNNN

FIGURE 3Q

49301 NNNNNNNNNN NNNNNNNNNN NNNNNNNNNN NNNNNNNNNN NNNNNNNNNN
49351 NNNNNNNNNN NNNNNNNNNN NNNNNNNNNN NNNNNNNNNN NNNNNNNNNN
49401 NNNNNNNNNN NNNNNNNNNN NNNNNNNNNN NNNNNNNNNN NNNNNNNNNN
49451 NNNNNNNNNN NNNNNNNNNN NNNNNNNNNN NNNNNNNNNN NNNNNNNNNN
49501 NNNNNNNNNN NNNNNNNNNN NNNNNNNNNN NNNNNNNNNN NNNNNNNNNN
49551 NNNNNNNNNN NNNNNNNNNN NNNNNNNNNN NNNNNNNNNN NNNNNNNNNN
49601 NNNNNNNNNN NNNNNNNNNN NNNNNNNNNN NNNNNNNNNN NNNNNNNNNN
49651 NNNNNNNNNN NNNNNNNNNN NNNNNNNNNN NNNNNNNNNN NNNNNNNNNN
49701 NNNNNNNNNN NNNNNNNNNN NNNNNNNNNN NNNNNNNNNN NNNNNNNNNN
49751 NNNNNNNNNN NNNNNNNNNN NNNNNNNNNN NNNNNNNNNN NNNNNNNNNN
49801 NNNNNNNNNN NNNNNNNNNN NNNNNNNNNN NNNNNNNNNN NNNNNNNNNN
49851 NNNNNNNNNN NNNNNNNNNN NNNNNNNNNN NNNNNNNNNN NNNNNNNNNN
49901 NNNNNNNNNN NNNNNNNNNN NNNNNNNNNN NNNNNNNNNN NNNNNNNNNN
49951 NNNNNNNNNN NNNNNNNNNN NNNNNNNNNN NNNNNNNNNN NNNNNNNNNN
50001 NNNNNNNNNN NNNNNNNNNN NNNNNNNNNN NNNNNNNNNN NNNNNNNNNN
50051 NNNNNNNNNN NNNNNNNNNN NNNNNNNNNN NNNNNNNNNN NNNNNNNNNN
50101 NNNNNNNNNN NNNNNNNNNN NNNNNNNNNN NNNNNNNNNN NNNNNNNNNN
50151 NNNNNNNNNN NNNNNNNNNN NNNNNNNNNN NNNNNNNNNN NNNNNNNNNN
50201 NNNNNNNNNN NNNNNNNNNN NNNNNNNNNN NNNNNNNNNN NNNNNNNNNN
50251 NNNNNNNNNN NNNNNNNNNN NNNNNNNNNN NNNNNNNNNN NNNNNNNNNN
50301 NNNNNNNNNN NNNNNNNNNN NNNNNNNNNN NNNNNNNNNN NNNNNNNNNN
50351 NNNNNNNNNN NNNNNNNNNN NNNNNNNNNN NNNNNNNNNN NNNNNNNNNN
50401 NNNNNNNNNN NNNNNNNNNN NNNNNNNNNN NNNNNNNNNN NNNNNNNNNN
50451 NNNNNNNNNN NNNNNNNNNN NNNNNNNNNN NNNNNNNNNN NNNNNNNNNN
50501 NTACGAAAAC CAGTCAGGCG TGGCGGTGCG CCCCTGCAAT CGCAGGCACT
50551 CGGCAGGCTG AGGCAGGAGA ATCAGGCAGG GAAGTTGCAG TGAGCCGAGA
50601 TGGCAGCAGT ACAGTCCAGC TTCGGCTCGG CATCAGAGGG AGACCGTGGA
50651 AAGAGGGGAG AGGGAGAGGG AGAGGGAGAG GGAGAGGGAT CAGATTACTT
50701 TTTAAAGCCC TACTTATTTA AAAAGACATC TTCCTTTTAA CCTCCAGGCT
50751 TTTGTAAAAT GCTTATTTCT CTACTGAAAT ATCCCTTCCC TCTCTTCTCT
50801 TCTTGCAGAA CACATCTATC AGACCTCCTG GTGAAGTTTC TAGCACAGCT
50851 TTTTTCTCTT TCTCCCTTAG AATTAATAAC TGCCTCATCT GTATTTCCAC
50901 AGCATTTCCA AGTACTTCAT ACACCAGCCT GTGTCAGTTT GAAGCATTAT
50951 TAGCTATTTG CCCTGCAAAC TTGGGAAGGG TTTTTCTGCC TTGCAGTAGT
51001 ATGAAGTCTG AAATCAGGAC TATGACTTAT CTATCTTACT TATATTTGTG
51051 AAGTTGGTTG TCTGATTTGC TTGGATAGTC TGGTCATCTC AATTGTACAA
51101 TAAGTGCTCC ATTACTTTAC TTTCCTTAAA ATACAACGAT CTCAGATTCC
51151 AACCCCAATC TACTCCAGTG GGTGGGACAT TCAACCTTAG TGTGCTGTCA
51201 AGCTCTCCAG GGTCATGTCA TCTGAAAGGC CCTCTTGGCC CTGTGAAGAC
51251 TGATTAACTG TGTAGCCATG GAGTCTGGGA TCTTGAGGCA GGAACTCTAG
51301 GCTGGTGTGC AGTCTCTTGC TCACTACTCC AATGTACTGC CACAGATTAG
51351 GACTTGAGTC CGCCATCTCT TTAAAAAAAA AAACAGTTTT ATTGAGATAT
51401 AATTGATCAT AATAAACCAC ACATATTTAA TGTATATACT TTATAAAATT
51451 TGGCAGGCAC ACCCATGAAA CCCATCACCA CAATCAATAT AGTGAACATA
51501 TCCATCACCT GCAAAAGTTT GTTGCGCCCT TTTGTAAACT CCTCTCTCTT
51551 ATTCTCCCTA CCTCTCCTCC CATCTCATCC CCATGCAATC ACGGATCTGC
51601 TTTCTGTCGC TGTAGGTTGG TTTGAATTTT CTAGATTTGT TTGGATTACA
51651 TAAATGGAGT CGTGCTGTAT GTGCTCTTTT TTCTGGCTAC TTTCATTCAC
51701 ATAATAATGT TGAGATTTAT CTATGTTGCA CATATTAATA GTTCATTATT
51751 ATTCTTTATT GCTGAGTATA TTCTATTGTA TGAATGTATC AAAATTTATT
51801 GATCCATTCA CTGTAGATGG ATATTTGGGT TGTCTCCAGC TTTTGGCTAT
51851 TATAAATAAA GCTGCTAGGA ACATTCATAT ACAAATCTTT TTTTTTTTTT
51901 TTGAGACAAG TTTCGCCCTT GTTGCCCAGG CTGGAGTGCA ATGGCACAAT
51951 CTCAGTTCAC CACAACCTCT GCCTGCTGGA TTCAAGTGAT TCTTCTGCCT
52001 CAGCCTCCCA AGTAGCTGGG ATTACAGGCA TGCGCCACCA CGCCTGACTA
52051 ATTTTGTATT TTTAATAGAG ACAGGGTTTC ACCATGTTGG TCAGGCTGGT
52101 CTCGAACTCC CGACCTGAGG TGATCCACCC ACCTCAGCCT CCCAAAGTGC
52151 TGGGATTACA GGTGTGAGCC ACTGTGCCTG GCTATCATGT ACAAATCTTT

FIGURE 3R

52201 ATGTGGTCAT GTGCTTCTTT TCTTTCTTTT GGGTAAATAC ATTGGACTGG
52251 GATGGATGGA TCATATAGTA GGTGTATATT TAACTTTCAG AGAACTACCA
52301 AATGGTGTTC CAGAATGGTC GCACTGTGTT ACACTCCCCT TGACATTGTA
52351 TGAGTGTTTC AGTTCTCTCT GTGCAGCTCT CTCCTCTTTG GGTCTTTGTC
52401 TTTCAGACTC TAGCACCTTA ATACCCCCCA AGCCTTGTCT TATCAACTCA
52451 GGGAGTTGGC CACACTCATC TTCGGTTTCC ATCCCTGCAC CTCTTCAGTT
52501 CCCCATCCCC GCACCATGGC TTGCAAACTC TCTCAAGACA GGAGGCTGGG
52551 GCAGTTGCAG GGCTTGTCTC ATTGGTTTTC TGTTTCTTAG GGATTACTGT
52601 CTTTCATTGC TGGATGTCTA ATGTATTAAA AACCATTTAT CTATTATATG
52651 TTTGATTTGG CTCTTTGGTT GTTTCAGGTG CGGAATTAAA TCTGGTTTCT
52701 GATACTCTGT CTTGGCTGAA AGCATACGTT TTCAGTGCCC ACTGCTGGAG
52751 AGGGGTGGAG GGCACTCAAG AGTTCCATTT GGACATTGAG TTAGAGAAGT
52801 TGTGAGAGTT TACATACCTG CTCTGGAGCC TTTACCCCAC TGTTCCCTCT
52851 GCATGGAAAA TGCTCTCCCC AGACTGGCAT ATGCCAAGGT CCAATATCAT
52901 TCCAGGGCTT AAATTGATTG CCAGATAAGC TTTGCCTGTA TTACTCTCAC
52951 TCCCTACTCA TTTTCTGTCC TGTTATCCTA TTTTGTTCCC TTGATAGCAC
53001 TTAACACTTT CTGAAATTAT GTCATTCGTT AACTCATTTA TTACCTATCC
53051 TACTCCAGTA AAATGTAATT TTCGTGTCAG CAGGGACCTT TCTGGTCATG
53101 TCCACTGTGC TAACCCATTT TGAGGGTTTC TGGCCCCTGG GGAGTGCTCA
53151 GTGTGAATTT GTGGAGTGAA TATTAAGATG AAGATAATGC TAAGTAGGCA
53201 GTTGGATATG TGAGTCTGGA GCTCAGAGGA GAGGAAAAGT GAAGCCTGAA
53251 GATACACATT TAAGAGTCTC TGCTTAACAG TGGCATTTAA ATCCATAGGA
53301 ATGAATGAAA CCCCTTGTAT TAGGGAATAG AAGAGCAGAT GGCCCAAGAT
53351 AGGATGCTAA GAAACCTCCG AATATGGAGT TCACATCTCA GTTGTGCCTT
53401 TGAAATTCTT GTCATCCACT TTTAGTTTTC TTCTCTTCCT ACTTGAAATT
53451 GCCTACCAAT TTTCAGAGCC CTCTCCTTCC TTTATACCGT CATGAGTTGC
53501 GCACTTTGCT TATTTTCCTG ATTAAGATCA TAAGCCTCTT AAGGGAAAGA
53551 TCCTGTAGTC AAAATTACAT TCTTGAATTG AATTGGGTTG GACTGGAGTG
53601 GACTGGAGTG ATAAGTATTG TCACATTATA GAATTCCACC CACTGAAGTG
53651 CAAGTGTTAA ATGTATTAAT ATTTCAAGTT AATGGATACT CTGCCCAAGT
53701 TTTTAGTTAA TTATTATTAA CTTTCCATTA TAAAAGCTTG TTTTTGTTAT
53751 TAAATCAATC ATCAGATTTA ACGCAGAAAT CAACTCATGT AAACATACAG
53801 TGAGAGAATT GTATTTTTCT CTAAATTTTC AGGACATTGA AAAAGACTTG
53851 AAACAAATGA GGCTTCAGAA CACAAAGGAA AGTAAAAATC CAGAACAGAA
53901 ATATAAAGCT AAGGTAAGAA ATACTTTTGT CTTTGGGTTC CATATTAAAT
53951 AGCTGGCTGG GGAGCCACCT TGTGATCTCG GTTGCCTGCA TGATTTTCCC
54001 CCTAGTATTT TATAGAATTG CTCTATTTTG TGATATGAGA CCAATGGTTT
54051 TAAGAATCTA TAATGTCAAA CAAAATTGAC CTAGGGAGTT GTAATTTTAA
54101 GGCTTTTACT GAATTGCTAA ACTTTTTTTT TTTTTTTGCT TTCTCCTAGA
54151 AGGGGGTAAA ATTTGAAATT AATTTAGACA AATGTATTTC TGATGAAAAC
54201 ATCCTCCAAG AGGAAGAGGT ATGCCATTAA GTCTAAATTT CCATTAGTAG
54251 GTATCAGAAA ATGCATATAT CTTAATAGCA TGTTTCATGA AATTATTTCA
54301 CAGGCTGTAG GGATAATTTT TTTCAACTTT TATTTTAGAT TCAGGTGGTA
54351 CATGTGCAGG TTTGTTACCT GGATATGTTG TGTGATGTTG AGGTTTGGGA
54401 TATGAATGAT CCCGTCACCC AGGTATTGAG CATAATACCC AGTAGTTAGT
54451 TTTTCAAGCC TTGCTTCCCT CCTTTCTTAC CCCCACTGTA GTAGCTCCCA
54501 GTATCTATTG TTGCTATCTT TATGTCCATG AGTACCCAAT GTTTAGCTCC
54551 CACTTATAAG TGAGAACATG CAGAATTTGG TTTTCTATCC CTATGTAATT
54601 GGTTTTCTAT CCCTATGTAA TTTGCTTAGG ATAGTAGCCT CCAGCTGCAT
54651 CCATGTTGCA TGGACATGAT TTCATTCTTT TTTATGGCTG CATAGTATCC
54701 CATGGTGTAT ATGTACCACA TTTTCTTTAT CCAGACCACC ACTGATGGGC
54751 ACCTAGGTTG ATTCCATGAC TTTGCTATTG TGAATAGTGC TGGGATGAAC
54801 ATGTGAGTAT ATGTGTCTTT TTGGTAGAAT GGTTTGTTTT CTTTTGGATA
54851 TATACCCAGT AATGGGATTG CTGGGTTGAA CAGTAGTTCT AAGTTCTTTG
54901 AGAAATATCC AAACTGCTTT CTACAGTGGT TGAACTAATT TACATTACAT
54951 TTCCGCCAAC ACTACATAAG CATTCCCTTT TCTCTGCAGC CTCGCCAATA
55001 TTTGTTTTTT GACTTTTTAG TAATAGCCAT TCTGACTCGT GTGAGATGGT
55051 GTCTCATTGT GGTTTTGATT TGTAGTTCTC TGATAATTAG TGATGATGAG

FIGURE 3S

55101 TATTCTTTTA TATATTTGTT GGCTGCTTGT ATGTCTTCTT TTGAGAAGTG
55151 TCTCTTTCTA TCTTTTGTCC ACTTTAAAAT TTGGGTTGTT TTTTCTTGTT
55201 CAGTTAAGTT CCTTATAGAG TCTGGATATT AGACCTTTGT TGGATGCATA
55251 GTTTGCAAAT ATTTTCTTCT ATTCTGTAGG TTGTCTATTT ACTCTGTTGA
55301 TAGTTTCTTT TGCTGTGCAG AAGCTCCTTA GTTTAATTAG GTTCCACTTG
55351 TCAATTTTGT TTTTGTTGCA ATTGCTTTTG AGGACTTAAT CACAAATTCT
55401 TTCCCAAGGC CCATGTTCAT AATGGTGTTT CCTAGGTTTT CTTTTAGGAT
55451 TCTTATAGTT TAAGGTCTTA CTTTTAAATT GTTAAGTCAT CTTTAGCTGA
55501 TTTTTGTATA CAGTGAAAGG TAGGGGTCCA GTTTCATTCT TCTGCATGTA
55551 GCTAACCAGC TATCCCAGCA CCACTTATTG GATAGGAAGT CCTTTCCCCA
55601 TTGCTTATTT TTGTCGATTT TGTCAAAGAT TATATGGCTG TAGATGAGTG
55651 GCTTTATTTC TGGGTTCTCT ATTCTGTTCC TTGGTTTATG TGTTTGTTTT
55701 TGAACCAGTA CCATACAGTT TTGATTACTG TAGTCTTATG GTATAGTTTG
55751 AAGTTGGGTA ATGTGACGAC TCTGGCGTTG TTCTTTTTGC TTAGAATTAC
55801 TTTGGCTATT TGGGCTCTTT TTTGTTTACA TATGAATTTT AGAATAGTTT
55851 TTTTTTTCTC CAATCCTGTG AAAAGTTACA TTGGTAGTTT GACAGGAATA
55901 GTGTTGAATC TATAGATTAC TTTGGGCAGT ATGGCCATTT TAATGATATT
55951 GATTATTCCA ATCCATGCAT GTGGCATGTT TTTCCATTTG TTTATGTCAT
56001 GTATGATTTC TTTCTGTGTT GTGTAGCTCT TCTTGTAGAG ATCTTTCACC
56051 TCCTTGGTTA GATGTACTCC TAGGTATTTT ATTTTATTTT TTGGTGGCTA
56101 TTGTAAATGG GATTACGTTC TTGATTTGGC TCTCTGCTTG AATGTTATTG
56151 GTGTATAGGA ATCCTATTGA TTATTGTACT TCGATATTGT ATCCTGAAAC
56201 TTTGCTGAAG TTGTTCATCA GTTCCAGGAA CCTTTGGGTC GAGTCTTTGG
56251 GTTTTCAACC TATAGTATCA TAAGCGTGAA GAGATGGTTT GACTTCTTCT
56301 TTTCTTATTT GGATGCCTAG AATTTTAGAA AATATTTCTA GAAAAATGTT
56351 TGGTGCTCAA GGCCAGGGAA CGGTGGCTCA CAGCTGTAAT CCCAGCACTT
56401 TGGGAGGCTG AGACGGGCAG ATCATGAGAT CAGGAGATTG AGACCATCCT
56451 GGCTAACATG GTGAAACCCC ATCTCTACTA AAAATACAAA AAATTAGCTG
56501 GGTGTGGTGT CACCCACCTG TAGTCTCAGC TACTTAGGAG GCTGAGGCAG
56551 GAGAATCACT TGAACCCAGG AGGCAGAGGT TGCAGTGAGC TGAGATCGCT
56601 GTACTGCACT CGAGCCTGGG CAACAGAGTG AGACACTGTC TCAAAAAAAA
56651 AAAAAGGGAA AGAAAAATGT TTGGTGTTCA AATGAGTCCT CCAAATACTT
56701 TTTATTCTCC CATTTTATTT TATTGGTGTT ATTTCTTTAG ATAAATTATT
56751 ACATTTTAAT TTACTTTTCT TTAAATAAAA GAGCTATTTT ACTCATAATA
56801 TTAATTTTTA TCATAGCCAA ATTAAAATAG AAGACCTGAT ACATTGTCAA
56851 CAACTAATAT ACTGACCTAA AAAATTGAAC AGGTACCCTG AAACCAGGCA
56901 CATTTATTTT AGGTCTTAAT TAGTTATTGA TAACTTTAAG TAAATCTCAT
56951 TTATGCATTT GGGCTCTCCT TGCCACAGCA AGGAGTAAAT ACAGTAAATC
57001 CAATACAGTA AATCCAAATT TCATTTTATT AGTTGATTTC AAAATCTTTT
57051 TTTATCCTGG TTTTATCAGA CCTATAACAA ATGTCAAAAT TAATTGGTTT
57101 ATTTTTCCAT TTTACCTTTT CTGAATTCAC CTTTTAAGTC AATATAAGTA
57151 TGAATAATTA TACCTGATGC TCAGTTTTTA TTTAATGTTC TTTATTAGCT
57201 TAAAACATTT TCATGTTAGC ATTTCTTATT TTTATGAGCA TTTGCTACAT
57251 AAAGACTTCA TTAGAGTGGT GATAGTTAGC ATTCACCTCT GTTCAACCAT
57301 AAATTCCTAA ATGCCCCAGA GGTGAGACAT CAGAGTGGAG CAGATCTGGG
57351 GACCTGCTTC TGAGTGGGAA CTTGAGAAGT GGTACTCTCA CAGAGCTTCT
57401 GTGAAGTGAG GTGCTGACGT TGCCCTGCTG AAATGAAAGA ATGGAGTCCA
57451 AAAAGTTTTA ACTGCCACTC TTTCTTATTC TTTGCTTTGA TCTGCGTGAA
57501 ACAGAAGTGT TCATTTTGGT ATTGACTACA AAATACTAGG AGCAGATTTA
57551 GGGAGCTGGT TAAGAATGTT GTACACTTAA AACAGGGCAT GAATGAGAAA
57601 AGCTTGAGAG CACTGTAGAA TGGAGCTGAA GTGGAATACT ATTGAAGTCA
57651 GAAAGTCTAG ATAAAATTAA GTTGCCTTAT GACCAGTGCT TGACACTGTT
57701 AACATGGAGA AGAAATGAAA ACATTTCTGT TTTTATCTAA CATAGCTCTA
57751 GTTTTAAAAC TCTATGGATT TATTTGTTTA GTAAACATTT GTTGAATATT
57801 TACTATATAC CTTGCTAATT AATTTTACTA GGAACACGAA AATATGGTTT
57851 TTCTTTCTTT CAAAATATGG CTAATTTATC ATGAAACACT GTGGAATTGA
57901 TTTAGGCAAT GGATATACCA AATGAAACTT TGACCTTTGA GGATGGCATG
57951 AAGTTTAAGG AATATGAATG TGTAAAGGAG CATGGAGATT ATACAGACAA

FIGURE 3T

58001 AGCATTTGAA AAACTTCACT GCCCAGAAGC AGGTATGTGT TTCTTGAAAG
58051 TTGTAAATGA GAAGGAACTG TTTTATTAGC AACCCATTTT GAACTCTGTC
58101 CCCATGCATC TGCCTCGGCT CCACTGTTAC TTGACCCCTT TCTGCCCTCT
58151 CTAAGCAAGG CAGAAACACA CTTATTATTC TCCTGCCACC CATGCAGTGG
58201 CCACACTCCC TGAGATCCAG CCCTCCTCTC CTGCTCCATA CCCACTCCCT
58251 CTTGCAGCTT TGGCTTCTCC CAGGAGCTCC AGACTTACCA GTCTTTCTCA
58301 TTGTCTTCTG GGAAGCTCCA TGGACAAGTG TTGCCAGTAT CTGAAACTCA
58351 GCTGTGTAAA GTCAAGCTCT TCTGTGCTCT TCCCAGTGAC CCTTTATTTT
58401 GGTTAGTGTC ACAGATGCAA CTGGCTGGGG CCAGTGTTGT GGGCAGTAAA
58451 AGAATTTATC AACACAATTG TAAGTAAAGA AAGGCAGATT TATTAAAGTA
58501 CAGAGATACG TTGCAAGAGT GCAATGGGCA GCACAGCAGA GAAGAGGCTG
58551 TCTGCTAAGA GGCAGGGGCT AGAGGGAAGT TTTATAGGGT CATATTGGAG
58601 GAGCTACATG CTGATAAGGT GTGCAGATAA GGTTTTGCTG CTTGGGCTAC
58651 ATGTGGAAGG AATGAGGTAT TTGGGAACAG GATGTGACAG CAGCTTGTCT
58701 GTGATGAGTC ATCTCTCAGA ACAGTTGTTC CCCCATCCCC ACCCCCAACC
58751 TGGGACCCCT CCCTTTTTGT TGTTTACTTA TCTTATGAGA ACTTCACAGT
58801 CAGTGCTGTC ACCAGGGTGC ACCCTTAGCA TAGTGTCTAT TCTGAGATGT
58851 CTCTGGAGTC TTCCTCTTCC TTCATTCTCT CTGTTACTGG TTTAGGGCTC
58901 TGTCATCTCT CAGTAGTGTG GTGTAGGCTT CAGAGACAGA TGGGAATTGA
58951 ATCTCAGCTG TTGCTGCCAC CTTCTGGTTA TGTGACCTTT CTTTCACAAG
59001 TTATTCCAAC ACTGAATCTC AGTTTCACCT TAGGAACAGG GGATAATAGT
59051 AGTAGGAATA ACCACACAGG GTAATTGTGA GGACCAAAGT GAGTTTTGAT
59101 GTATAAACGA CCTGGCACAT ACTAGGTGCC TAAATTAAGT GCTGTCTTTT
59151 CATTTTCCCT TTTCCTTCCC CTTGCTGTAT TGCCTTATTT GCTTATGTGA
59201 CCTTCTTTCT CTAGTATTTC CCCTTCATTC TCTAAATGGT TACTGTATTA
59251 GTCCATTTTC TTGCTGCTGA TAAAGACATA CCTGAGACTG AGCAATTTAC
59301 AAAAGAAAGA GGTTTAATTG GACTTACAGT TCCACATGGC TGGGGAAGCC
59351 TCACAATCAT GGTGGAAGGC AAGGAAAAGC AAGTCACATT TTACATGGAT
59401 GGCAGCAGGC AAAGAGAAAG AACTTGTGCA GAGGAACTCC TCTTTTTAAA
59451 ACCATCTTAT CTCGTGAGAC TCATTCACCA TCACGAGAAC AGCATGGGAA
59501 AGATCCGCCC CCATGATTCA ACCACCTCCC TCTGGGTCAC CCCACAACAC
59551 ACAGGAATTC AAGATGAGAT TTGGGTGGGA CACAGCCAAA CGATATCAGT
59601 TACTAAAGTT ATCTTGGCAT ATTATTACTC TGCTCAGATT TTTTTTTTGG
59651 ATAATACCTG CAGAATAAGG TCCATTCCAC ATATTATCAC ATTTAACACT
59701 ACATGGCCTA ATTCTGCTGT GACCCACTTT TCTCATCCCA GCATGGCCTC
59751 TTTCCTTCCA TGGAAAATGG GATCCATACA GCCTGCTGGA ATGCCCATTT
59801 TCTCCTACAG CTGGAATGCC CATTTTCTCC TACAGCATTT ACAGAACTGA
59851 CTTGGCTCAG TTTCCTCTTC CTGGAATACT CTCTGCCTCA TTTCCTTCTG
59901 GAAAAATCTC CATTCAGCAG GCATCTTATT GAGGATCTCC TTTGTGCCAA
59951 AGACTGCTCA CTGGTAGGGA GCTCAAAGAT GAATGAAATC TGGGCCCTGT
60001 TCTCAATATC ACAGAAGTGT TATGAGCAAA AAAGTCACAA AACATGTTTT
60051 CTGAGCCTGA AATGTTAATC ACTGTTTGAA GTGCGAGCTG GGTGGAGAGT
60101 CAGGGAGGTC CGCACTCCTC CAGGGCTTCA CATGCCATCA TTTTTGTGAT
60151 TGAGAAGGAT CATGCTGGCT GCAGAGCAAA GGATGGCATG GAGGGCAAGA
60201 CTGAAGGCAG GAGAAGAGTC CAAGTGCATG AGCCAGAGTG GTGCAGGGAG
60251 AATAGATACT GAGTGTGGGA ACTGAGGAAG AGAAGGGGCT CAAGGATATT
60301 CCCAGTTTTC TAATTCAAAT GCATGAAGCT TTCATCAACC AAAAATACAT
60351 CACATGGAGG GTAATGGGGT CGGGAGAGAC AAGGTAGTGA TCTAAATTTG
60401 GAACATGTTG AGATTTAGGT CTATAGAGCA TCAGTTGCAG ATTCTATATA
60451 AGACTGAAGG CCTGGGGCAT ATCAGGGATA AAGATATAGC TTGGTGGCCC
60501 TTAGCATATC CGTGGTTTTT AACTTTGGTG ATGGTCAAAA TACCTATGCA
60551 GAAGGACTGG AGTGAGAAGG AAATGGAGCT TAGGACATAA CCCTACCACT
60601 ATATAAACAA ACTTTGGAGA ATCAGGAGAG AGTAAAGCCA AAGGAGGAGA
60651 GACAGGTCAT GGAGGAGGCA CAGGAATTGG CAGCATCAAC TGGAAGAGAA
60701 AGGCCAGATG AGGTGAGTGG GATTTGGCCC TTCAGGAGCC GTTAATGGCC
60751 TCAGGGAAAG CAGTCAACTG TGTAAGGGGT AAATTCAATG GTTATCTTTG
60801 CATCAGTTTG CTGGGAAAAG CAGAGGGGGT TGGCTGTTTT TTAGATGAAA
60851 GAAAAAAAAA CCTTCATCAG TAGTATACTG AAAATTGTCT CTCATTTTAA

FIGURE 3U

60901 TCTGTATTCC TGTAATTATT ATTTAGGCTG AAGGATTTTT CCGTATGTTT
60951 GTTGACCATT CATATTTCTC CTTTTTTTTT CTTTTTTCTT TTTTTGTTTT
61001 TTTTTTGAGA GGGAGTCTCC CTCTGTCGCC CAGGCTGGAG TGCAGTGGCA
61051 CAATCTTGGC TCACTGTAAC CTCCGCCTCC TGGGTTCAAG CGATTCTCCT
61101 GCCTCAGCCT CCCTGAGTAG CTGGCATAGG TGCGCGCCAC CACGCCTAGC
61151 TGATTTTTAA AATATTTTTA GTAGAGATGA GGTTTCACCA TGTTTGCCAG
61201 GCTGGTATTT GAACTCTTGA TCTCAGGTGA TCTGCCCACC TTGGCCTCCC
61251 AAAGTGCTGG GATTACAGGC ATGAGCCACC ACGCCTGGCC AACCCTTCAT
61301 ATTTCTGTTA TGAATTATGT ACTCATGCCC TTCATCCTTT TTTCTACTGA
61351 AAATGGCATG TTTGTTTTTT TCTTTATAAG ACTGATTTAA ATCAAACCTT
61401 TGCCTGTAAT ATGTATTGCA AATGTTTTCC TCAGTTGGTT GTCAGATCTC
61451 ATTTATAGTA ATAACAGCAA ATATATATGA GTGTGTGTGT GTGTGTGTGT
61501 GTGTGTGTGT GTGTATTTGT GTATTCATCC ACTTAGGAAT AAATTTTATG
61551 AGAATTGTGC GGCATATAGA AAGAAAACTG TAAAACCTTA CTGAGGTATT
61601 TACAGACCAC TTGAATAAAT GGAGAGAAAT AACGGTGCTA TATATTGGAA
61651 ATATTTTTTC CAAATAAATA TTGCAGTATC GTTGTCTGAG GTATTACCCA
61701 GAACTCTTTG TCTCACGACC AAAAGAATAA GGAGGGTGGA CAGTAAGGGT
61751 GAGTTTGGAC CGAAAATTTA ATAAACAAAA GAGGAAAGCT CTTCACTGTG
61801 GAGAGGGGAC CCAAGAGGGT TGCCATTTCA CAGCTGAGTA CAAAGGCTTT
61851 TATGAGGAAC CTGATAGGGC TGGGGGTTTC ATTTGCATAA GGCATGAATT
61901 TCTGGCAGCT CCACCCTGTT CTCCTAGTAT GCTGACTGGC TAGGGGTTGT
61951 TTTTGGAAAA GGCACCACTC AGAAAATGAC ATGATGGTTG ACCAGGCATG
62001 GTAGTTCATG CCTGTAATCC CAGCACTTTG GGAGGCTGAG GTGGGCAGAT
62051 CTCTCAAGGC CAGGAGTTCG AGACTAGCCT GGCCAATATG GCTAAAGCCC
62101 ATCTCTACTA AAAATACAAA AATTAGCCAG GTGTGGTGGT GCACACCTGT
62151 AATCTCAGCT ACTTGGGAGG CTGAGCCACA AGAATCACTT GGACCTGGGA
62201 GGTGAAGGTT GCAGTGAGAC GAGATTGTGC CACCACACTC CAGTCACACT
62251 CCAGCTGGGT GACAGAGCAA GCAAGACTCC ATCTCAAAAA AAAAAAAAAA
62301 AAAAATGACG TGGTGTAAAG ACCAGTTGGA GCCTTGGCCC ACAACCAGCT
62351 GAGTGTTGGA GTGATGGTTC ACAGAGGCTT GGCTCACAGT CCAAAGTATG
62401 CCCCAAAAAG GAAAGGAATG TGCTCACTGG GGCCCACCAT GTACATGCCC
62451 ACAAAAGGAG AAGGAACTAT TTGCTAGAGG CCCACTGATT GCACAAAGAA
62501 CAAAGGCATT TCTGTGTTGG ACTTTGCTCC CTTATCTGTG CAGCTGTGGG
62551 CATGTTTTAG GCAAGCTTCC TGTGCTAGTT CCCTTATCTG TGTCTGCAGC
62601 TTGATTTTTC AGACTGTTCT TTTGTTTGAA AGAATTCTGA GGACCTGCCC
62651 TAACTGCCTG CCTAACTGAT TCTTTCTTTC TCCTCCCTCA ATATGTGGAT
62701 TTATGGCTAT TTCAATCAAA ACCACAGTAG GATTTTTTTT TTAATGGTAT
62751 AGGGAGATCT TGGCAGGTTG GAGAATCCTG GAGCTTCTTA AGTGGCCAAA
62801 AATTTTGAAA AAGAAGAACA GTGAAGTGGT ACTTACATTT CCAAATGTCA
62851 AAATATATTA CAGAAATTAT AGTCATTCAC ACAATATGAT AGTAGCACCC
62901 AAATAGTTAA AACAGTGAGA AGAGAAAGTT AGAAACAGAT CCTAGTATGT
62951 ATCATAATTC AGCACAAATG AAAAGTAACA TCACAAGTCA GCGTGAAAAG
63001 AAAGGATTAT TCAGATAAAT GCTGCTGGGC CAATTGGTTA ACAGTTTGGG
63051 GAAGATTGTG AAATCAGACC CTATATAATA TGATACAACA AAATAAATTT
63101 TTTAAAAAAG AGTTATATGT AAAAAGTTAT ACATTAGAAA ATGAAATAAA
63151 AGAACATAGG TCATTTTTTT TTTTTTTTGA GACAGCGTCT CACTCTGTCA
63201 CCAAGGCTGG AGTGCAAAGG CGTGATCTCG GCTCACTGCA AACTCCGCCT
63251 TCTGGGTTCA AGCGATTCTC CTGCCTCAGC CTCCCGAGTA GCTGGGACTA
63301 CAGGCACCCG CTACCACGCC CAGCTAATTT TTATATTTTT GATAGAGACG
63351 GGGTTTCACC ATGTTGGCCA GGATGGTTTC GATCTCTTGA CCTTGTGATC
63401 CGCCCGCCTC GGCCTCCCAA AGTGCTGAGA TTACAGGCGT GAGCCACTGC
63451 ACCCGGCCGA GTTAATTTTT TTTGAACAGG GAAGAGCTAT CTGTTCAAAA
63501 TACATAGAAA AAAAAACCAC AGAATAAATT AGTAATAATT CAACTTTAAC
63551 AACAAAAAGC TGTAATAAAG CAAATCATAC TAACCCCT (SEQ ID NO:3)

FIGURE 3V

FEATURES:

| | |
|---|---|
| Start: | 2012 |
| Exon: | 2012-2128 |
| Intron: | 2129-10078 |
| Exon: | 10079-10175 |
| Intron: | 10176-17356 |
| Exon: | 17357-17454 |
| Intron: | 17455-19144 |
| Exon: | 19145-19228 |
| Intron: | 19229-19311 |
| Exon: | 19312-19382 |
| Intron: | 19383-21317 |
| Exon: | 21318-21404 |
| Intron: | 21405-25173 |
| Exon: | 25174-25228 |
| Intron: | 25229-27433 |
| Exon: | 27434-27634 |
| Intron: | 27635-27711 |
| Exon: | 27712-27793 |
| Intron: | 27794-29849 |
| Exon: | 29850-29983 |
| Intron: | 29984-36496 |
| Exon: | 36497-36678 |
| Intron: | 36679-40418 |
| Exon: | 40419-40485 |
| Intron: | 40486-42286 |
| Exon: | 42287-42403 |
| Intron: | 42404-43377 |
| Exon: | 43378-43464 |
| Intron: | 43465-53832 |
| Exon: | 53833-53913 |
| Intron: | 53914-54149 |
| Exon: | 54150-54218 |
| Intron: | 54219-57905 |
| Exon: | 57906-58032 |
| Intron: | 58033-59835 |
| Exon: | 59836-59963 |
| Intron: | 59964-60551 |
| Exon: | 60552-60587 |
| Stop: | 60588 |

Chromosome map:
Chromosome 13

FIGURE 3W

Allelic Variants (SNPs):

| DNA Position | Major | Minor | Domain | Protein Position | Major | Minor |
|---|---|---|---|---|---|---|
| 1848 | A | G | Beyond ORF(5') | | | |
| 1993 | A | C | Beyond ORF(5') | | | |
| 3796 | C | T | Intron | | | |
| 4854 | C | G | Intron | | | |
| 7649 | A | G | Intron | | | |
| 8491 | G | A | Intron | | | |
| 8928 | T | C | Intron | | | |
| 18844 | A | T | Intron | | | |
| 19055 | G | A | Intron | | | |
| 19607 | G | C | Intron | | | |
| 19935 | G | A | Intron | | | |
| 20595 | T | G | Intron | | | |
| 22513 | C | G A | Intron | | | |
| 25121 | T | C | Intron | | | |
| 25883 | A | G | Intron | | | |
| 26375 | A | T | Intron | | | |
| 26693 | C | T | Intron | | | |
| 30477 | T | G | Intron | | | |
| 30858 | A | C | Intron | | | |
| 31028 | A | G | Intron | | | |
| 37308 | - | T G | Intron | | | |
| 44213 | G | A | Intron | | | |
| 54046 | G | A | Intron | | | |
| 56598 | A | G | Intron | | | |
| 56759 | A | T | Intron | | | |
| 58510 | A | G | Intron | | | |
| 60356 | G | A | Intron | | | |
| 61643 | C | T | Beyond ORF(3') | | | |
| 62221 | G | A | Beyond ORF(3') | | | |
| 62306 | A | - T | Beyond ORF(3') | | | |
| 63224 | G | T | Beyond ORF(3') | | | |
| 63350 | G | A | Beyond ORF(3') | | | |
| 63517 | C | A | Beyond ORF(3') | | | |

Context:

DNA Position

1848
TTTCCAGAATTCCCCCTAGGGGGCAGTACGTCCCCACTAAGAAAGGCTGAACTATAAAAG
TGCACAAGCCTAAGGACATTCCTGCTTTATAAAGGTGCGAAACACCGGATATAGTATCTT
TCATTCTCAGAACAAACTTGCAAAACAGGTATTGTTATTCCATTTTAGAAATTAGGAAAG
TGAGGTTTTGCCAGGTTAAGTGACTTACCCGAGAATACAGGGCAAAAGTGTATCAAAGCT
GAGCTATGACCCGTGTCTGACCAAGAAACTCTGTCTCATTTCAGTTATCTGTGGCCACAA
[A,G]
GAAAGTTATTTGTCTCTGTCTTGGCAAGGCTGGGAGGAAAGTTTTAGCTAAGTGAGTTCT
TTTACACTTTAGTCATCAGTTTTCTGACTTTGTTAGTCTTTATGAGACGTGTGTGATAAA
TTTACATTACTCTAATTCCAGGAAACTCAGCCCATTGGAGACCATGGATAAGTACGATGT
GATTAAGGCCATCGGGCAAGGTGCCTTCGGGAAAGCATACTTAGCTAAAGGGAAATCAGA
TAGCAAGCACTGTGTCATAAAAGAGATCAATTTTGAAAAGGTAAAGTTAAGTTCAAATTT

1993
CAGGTATTGTTATTCCATTTTAGAAATTAGGAAAGTGAGGTTTTGCCAGGTTAAGTGACT
TACCCGAGAATACAGGGCAAAAGTGTATCAAAGCTGAGCTATGACCCGTGTCTGACCAAG
AAACTCTGTCTCATTTCAGTTATCTGTGGCCACAAAGAAAGTTATTTGTCTCTGTCTTGG
CAAGGCTGGGAGGAAAGTTTTAGCTAAGTGAGTTCTTTTACACTTTAGTCATCAGTTTTC
TGACTTTGTTAGTCTTTATGAGACGTGTGTGATAAATTTACATTACTCTAATTCCAGGAA
[A,C]

FIGURE 3X

CTCAGCCCATTGGAGACCATGGATAAGTACGATGTGATTAAGGCCATCGGGCAAGGTGCC
TTCGGGAAAGCATACTTAGCTAAAGGGAAATCAGATAGCAAGCACTGTGTCATAAAAGAG
ATCAATTTTGAAAAGGTAAAGTTAAGTTCAAATTTCTGTTAATTTTCAGTGGGATATTCA
GCTGGCTTTTAATCCAATATAAAAAGGAAATTTTTATTTTTTATAATTTCGAATTTTAAG
CCATAATTGATTTTTGTTAATTCAACCTCCTAAGTCCATTGTCCAAACAGCAACCAATGA

3796 TTACCACAAAAAATTGCAAGAAAACCTACCCAAACTTAAAGCTCAAGAGTAGATGACTGG
CTTCCAGGGATAATGATTTATTTCCCAATATAGGTCTCTTTTTGTGAATCCATGGCATAT
TCATAATAATGTCCTCTTATTCTAGTGGCCCGCAATAGCTTCCTCCCATGACATTATTCT
GCTCACTCTCTTTTGTTTATCTGACTGCTCTCCCTCAGGCTTATCTCTGTCTTCGCCCTG
TGTATGTCCTCAACCATGTGTCCTTTTCTGATTTTCTTTTTCTGTCCATTGTCACCTAAA
[C,T]
TGCCCCACTTCAGTGTTTACCAATAAGTAGATCTCTCTTAAATCTCTGTCTCTACCCCTG
GCATCTTTCAGTACCCTAGTTCTGCATTTCTTCTGCCAGCTAGATAACTTCAGGTAATAT
CTGTGGTTTTGTTTTGAGGTGGAGTCTCGCTCTGTCGCCCAGGCTGGAGTGCAGTGGTGC
CATCTCGGCTCACTGCAAGCTCTGCCTCCCAGGTTCATGCCATTCTCCTGCCTCAGCCTC
CCGAGTAGCTGGGACTACAGGCGCCCGCCACCACGCCTGGCTAATTTTTTGTATTTTTAG

4854 CTTGAATTTGCTTCAGTCCTTTTGTCGAGGCCCTGGGTCACTTGGATCCTTCAAGTGGCT
CCAGCCCAATTTTGATAATGCTCCAGCCATGCCCCCAAACCTTCACTGGGACAGAGGCTG
TAAAGAAAGAGTTGCCTAGGTTTGACTACATAAAAATAGAAAACGTTTGTATGTCAAAAC
AAACACTATAAATAAATTCAAAGAAATCGAGAAGGTGCCAAAAATATTTGCAAGTATTGA
CTTAATGGTGTTAGCCTTTTATTAAATCAATAAAAAGATAAAATCCATATATGAAGTCAT
[C,G]
GTACAAAAATTTGAAACTCAGTAGAAAACTAAGAAATTAGGAGTTTATTCAAAGAAAAAC
CCCACAGATAAACAGTTAGAAAACAAATGTCCAACAGTAGGTAATTTGTTAAGTAATTTA
TAAAAAACTAAGTGGCTATTAGCAATCATGTTGTAGGTGAAGCATTGACATGGGAAAATT
TCAATGTTTGCAATGTTTGAGAAAATAGTAAGTGTAAAATAATATAATCTTTGGAAAAAT
ATATATATTCTCCATATATATGTATACCTACAAATATGTTCATATATGTACAAAGAAAGA

7649 CATGATACTACATTGCCTCCCTTTATTTTTAATGACTGCATAGCATTAAAGTGGTAGCAG
GTCAAAAATACCATAATTTAGCTGGGCATGGTGGCAAGTGCCTGTAGTCCCAGCTATTCT
GGAGGATGAGTTGGGAGGATCCCTTGACCCCAGGAGTTAAAATCCAGCTTAGACAACATA
GCAGAACTCTGTCTTAAAAAAAAAAAAAAAGCTAGCAAAACACCCCTGTAATTTATTTAA
CTCTTTTTCTATTTTCAGATAATTACATTGTTTGGTTGGTTTTTTGGCTACGATTCAATA
[A,G]
CATTTAATATGTAAAGTATGATTCATTTTTATTAAACAAAACTATGTATATATGCTTGCC
TATATATGCATGAAATAAAAAGCTCTAACTATTAACAACAGTTATCCCTAGGGAATATAG
TATTAGGTTGGCGCAAAAGTAATTGCATTTTTGCCATTAAGAGTAAGGTTACCACCTATG
GGCTTTCGTCTGTGGGCTAGATGAGAAAGAAAGAGGGAAGTTTCACTTTTACCTTATTCA
CTTCTATTTGACTTAAAACAAGCGTGCATTATTAGAGTAACTTAAAAACTAGCAATAAAA

8491 GCCTGTGGTCTCAGCTACTCAGGAGGCTGAGGTGGGAGGATCACTTGAGCTCAGTGGGCA
GAGGCTGCAGTGAACCAAGATCATGCCACTGCACTCCAGCCTGGGTGATAGAGCAAGACC
TTGTCTTAAAAAAAAAAAAAAAAAGATTTCTTCAGCAGGATACAGACCCCCCACAAAAAT
GAACATTTTAAAGATTCATATTATATATTGTAAAACTGCCTTCCCAGAAATATTTTATCA
ATTTGTGTAGTTTTACCAGAAATAAATGAGTGTCCATTTTGCTGCTTTCTGGCCAATAGT
[G,A]
GTTATTGACATTCTTTTCATCTTTGCCAGTTTCATACATGGAATACTATATTACATTTTG
TTTTAGCTTTTATTCCTTTTTTTTTTTTTTTTTGCAATGGAGTCTTACTCTGTCACCCAGGC
TGGAGTGCAGTGGTGTGATTTTGGCTTACTGCAGCCTCCATCTCCCAGGTTCAAGGGATT
CTCCTGCCTCAGCCTCCTGAGTAGCTGAGACCACAGGTGTGTGCCACCACGCCTGGCTAA
TTTTTTGTGTTTTTAGTAGAGACAGGGTTTTGCTATGTTGGCCAGGCTGGTCTTGAACTC

8928 GATTTTGGCTTACTGCAGCCTCCATCTCCCAGGTTCAAGGGATTCTCCTGCCTCAGCCTC
CTGAGTAGCTGAGACCACAGGTGTGTGCCACCACGCCTGGCTAATTTTTTGTGTTTTTAG
TAGAGACAGGGTTTTGCTATGTTGGCCAGGCTGGTCTTGAACTCCTGGCCTCAAGTGATC
TGCCTGCCTTGGCTTCCCAAAGAGCTGGGATTACAGGCATGAGCTACCACACCCAGCCAA
ATTTTGCTTTAGTTTTTATTCCTTTGATTACTGCATGAGATTGAATATTTTTTCTATCAG
[T,C]
CATTTTTATTTCTCTTTTTTTTTCGAGTTGACTATTCTTGTACTTTGCTATTTTTCTGTT
GGGGTGTTTGCCTTTTTAAAAATTATTTGCCATCAATTTTTATATTATAAATATATTTGT
CATATATGGTACAAATATTGTATCTTATCCTTTTGTTTGTCTTTTAATTTTGTTTATAAT
ATTCTTTTAAATAAATAGTAGTTAGGAATTTTTTAAGTTGCTAAATGTATCCAGCTGGTA
GGAGTAATTTAGCTGTTTTTGTTTTGAAACTCCTATGTACTGACTATACAATTTAAATTG

18844 GAACACATTTTCATAAAGAGGCTCATGGTCAACAAAGATAAAATCAAATCATGACTTAGA
AATAAAACTAAACTTCAAAGGTAAAGTATTTGTTGGTTTTATATTAGATATACTGATATT
TTATTACAATTCCTAACCTCACAGATCCCCCATTTCTTCCTCTTTCTCTCCCCACCCTTG
TCACCCTCCTTCCACTGTAAAGGAAGAACCAATGGCTCCCAGGTTATCAGGAAACAGGGC

FIGURE 3Y

TGCTTGTGTACTATTCACGATGCAGTTAGCACCCCAGGGTTAAGTAGGAAAAAAAGAAAA
[A,T]
CATGAACGGCATGCCTCTTTCCCTTGCTTCTACTTATCTTTTTCTGCATGTGGAATTTCC
CTTGATTTTACCAGTGATATTTGGATTACTTTTCTGTGCCTCCATTTTTTTAGTTGTAGA
ATGAAAATAATAATATGATAAAGTGTACCTATTAACTTCATTCCTATAAATACACATACA
CTATATGTGTGTATGTGTGTGTGTGTGTGTGTATAATTTCTATCTTTTTGCATGTTACCA
TGAAGACATTTCAGTGACTACCAGGCTATTCAGTGGCTTTGTTTTGTGTTCTCTCTATAG

19055 ATGGCTCCCAGGTTATCAGGAAACAGGGCTGCTTGTGTACTATTCACGATGCAGTTAGCA
CCCCAGGGTTAAGTAGGAAAAAAAGAAAACATGAACGGCATGCCTCTTTCCCTTGCTTC
TACTTATCTTTTTCTGCATGTGGAATTTCCCTTGATTTTACCAGTGATATTTGGATTACT
TTTCTGTGCCTCCATTTTTTTAGTTGTAGAATGAAAATAATAATATGATAAAGTGTACCT
ATTAACTTCATTCCTATAAATACACATACACTATATGTGTGTATGTGTGTGTGTGTGTGT
[G,A]
TATAATTTCTATCTTTTTGCATGTTACCATGAAGACATTTCAGTGACTACCAGGCTATTC
AGTGGCTTTGTTTTGTGTTCTCTCTATAGATCCTCGGTTGGTTTGTACAGATTTCTCTAG
GACTAAAACATATTCATGACAGGAAGATATTACACAGGGACATAAAAGCTCAGGTAACAG
CTCAGAGAGAAGACTAAGACAGAACTGATCTTTTCTTGAAGTACCTCAAACAACATGACA
TTTTCTCCATTTATAGAACATTTTTCTTAGCAAGAACGGAATGGTGGCAAAGCTTGGGGA

19607 TATAGAACATTTTTCTTAGCAAGAACGGAATGGTGGCAAAGCTTGGGGACTTTGGTATAG
CAAGAGTCCTGAATAAGTAAGTACTTTGAAAATAATTTTTCTTTCTAGTCAAAATAGCCC
AAATATGTATTTTTAGATATCATGGATTAAGAAGATATTAAAATCTTGGTTGTCTAAATA
ATTTTAGGTAGCTTTATGTAAATGCATTACATCAGATGGTACTTTGAGATTAAAATTCTC
AAGATAAATTGTGGTGTAATAGAATGATGTTGCTAATATTCTGTAGTGTGATTCCAGTTT
[G,C]
TCAAATATGGATGTGACTGTAATATGCATAAAGCTAGAGAGAATTTCGTGAAATAGGCAG
GTTTACACTTCTTAATGAAAAAAGTCAAACTCTATAAAATATTTGAAGAGATTTATTCTG
AGCCAAATACGAGTGACCAAAGGTCCATGCCTGTGACATAGCCCTCAGGAGATCCTAAGA
ACATGTACCCAAGGTGGCCGGTCTACAACCTGGTTTTGTACATTTTAGGGAGATGCAAGA
CATCAATTAGATGTACATGGGTTTGGTCCAGAAAAGCAGGACAACTCAAAGCTGGGAAGA

19935 ATAAAGCTAGAGAGAATTTCGTGAAATAGGCAGGTTTACACTTCTTAATGAAAAAAGTCA
AACTCTATAAAATATTTGAAGAGATTTATTCTGAGCCAAATACGAGTGACCAAAGGTCCA
TGCCTGTGACATAGCCCTCAGGAGATCCTAAGAACATGTACCCAAGGTGGCCGGTCTACA
ACCTGGTTTTGTACATTTTAGGGAGATGCAAGACATCAATTAGATGTACATGGGTTTGGT
CCAGAAAAGCAGGACAACTCAAAGCTGGGAAGAATGGGAGGGAGCTTCCAGGTCATAGGT
[G,A]
GATTAAAAACTTTTCTGATTGGCAATTGATTGAAAGAGTCTATCTGAAGACCTGGAATTA
GTGGAAGGGAGTGTCTGGGTTAAGATAAGGGGTTGTGGAAATGAAGGTTTTTATTATGCA
GATGAAATCTCCAAGTAGCAGGCCTCAGAGAGAATAGATTGTAAATATTTCCTCTTATCG
GATTTAAAAAGGTGCCAGACTCTTAGTTAACTTTTTCCTGGATCAGGAAAAAGCCTTGGA
AAAAGAAGGGAATTTTCTTCAGAATGTAGATTTTCCCCACAAGAGATACCTTTGCAGGAC

20595 GCCTGCTATCTGTCATGTGATGTTATACTAGAGTCAGGCTGGACTTTGGTATCTTATTGC
TACAAGGAGTCTGCTTTGTCAGTCTTAAGGTCTGTTTTAATGTTAATGCTGGTCAACTGT
GCCTGAATTCCAAAGGGGAGGAGGAGTTAATGAGGCATATCAGACCCTGCTTCCCATCAT
GGCCTGAACTAGTTTTTCAGGTTAACTTTGGAATGTCCTTGGCCAAAGGGAGGGTTTATG
AGTTGGTTGGGGGGCTTAGAATTTTATTTTTGGTTTACACACTTTCTAGCAAAATAAATT
[T,G]
GTGCACCTGTTTGGAAGACAATTTGGTGGCAATATGTACCAAGAGATTTTTTAAATATCCT
GTTTCTGGGACTTCTTCCAAGGGAATAATTTGAAATTTGGAATAACGTAAATGCCTAAAT
AATTGGGAAATGGTTAAATTTAATAAAGCTTGGCATGGCCATGGCCATGTACCTGAATAT
ATCATAAACATTTATGGTTTTGAAGACTTCTTGATAACTTTGTTATACTAAGCAAAGAAA
ATGGAATTCTGAATTTTAAATACATTGTGATCACGGTTATATGAAAAATATGTGTGGAAA

22513 AGCGATTCTCCTGCCTCAGCCTCCTGAGTATCTGGGATTACAGGTGGCTGCCACCATGCC
CAGCTAAAGTTTTGTGTTTTTAGTAGAGATGGAGTTTCACCATGTTGTCCAGGCTGGTCT
CAAACTCCTGACCTCACGATCTGCCTGCCTCAGCCTCCCAAAGTGTTGAGATTACAGGTG
TGAGCCACTGTGCCTGGCTGGGCACTGGCTTTTTAAGCTTTTAATATTTAACTTCACCAC
TCAGTTAGTATAGAAACAGTTGTGATGGAGGCCTGCATTGGTAAGACCTGGCCTGCCACA
[C,G,A]
AATGGGGATCCCAGTGACTATCTCTGAGCAGTGTTACCTGAAGGTTTCAAACTTGTTTAG
AAGAAAGCCATTTCTCTTCATTTAAAGATACAAGTGGTATAAAAAATAACATCGAAAATT
GCAGTCACTGTGATGTCCATTTTTGTATTATATGTTCATATCTTTGAAGCACTGTTTAGT
CTATTGCAAGAAAGATTGAAGAGGATGAAGTAGAAGACAATGTGGTCTGGTGACCGCTCA
CTGGATTAGGAGCTAGGAATCCTAGTCTTGGCTCAGTTGCTAACTTGACCAAGTCAGTTG

25121 CTTTTGAGTCAAAACAAATCCATGTTTGAGTTCTGCCTGCCTCCTCCAAATTGCTCAACA
TTTCATCATACATACATTGTTTTTGAGCAGGAAGCTGAACTAAATATTAAGCCACCAGGT

FIGURE 3Z

TGTAGCAAAGTTTGTGTGCCTTTCTTTGACTAGAAATCTGACAAACTACAAATGGTTTTC
ATTTTACCTCTTATCTTCTAATAAGAATTGATGATATATCTGAAAGCATTTGTAAAAGCT
GATCAACTTACATAAAATTGTAAAGCGACACAAATTTAAGGCACTGTAAGGATAAAAGCT
[T,C]
TTATTAAGAATTATGGATATTTTCTTGGCATGTAAACTCTTATCTTCTTTAGGGATATTT
GGTCTCTTGGCTGTGTCTTATATGAGCTCTGCACACTTAAACATCCTGTAAGTATGCTCA
TTGTCAGACTAATCTTGAATTATTGGAATTGTAGAAAAGAAATTAACTTCTGGGAGAAAA
AGGTTAATGTTTGGTTTTATTAGATTGTTAAAAATTATATGGATAAGCTACTTAAAATAA
TGATAGATGACATGGAAAGCTGTCCAAGCAATATTATAAAGTAAAAAGTCCAAGTTGGAG

25883 TACTAAAAATACAAAAATTAGCCAGGCATGGTGGCATGTGCCTGCAGTCCCAGCTAGTTG
GGAGGCTGAGGCACGAGAATTGCTAGAACCCAGGAGGCAGAGGCTGCAGTCAGCTGAGAT
TGCGCCACTGCACTCCAGCCTGGGTGACAGCGAGACTCCATCTAAAAAAAATAATTAATT
AATTAATTACTGTATGAATAGATACGTTCAGCAAAAGAAAAATGTACATGGGCAAAGTTC
ATAGGAAACCAGGCACAAGCTTTTAAGAGTCTTTTCCCAGAGGTCACATGGGATGTGCCA
[A,G]
ATCCTCCAGCATTGTTACCCACGTCACCTGTGAAATGTGATCTATAAGAAAGCTCATCGG
ATATACCCAGTGCCCAGGATTTTTACTGGGGACTGGTCACATAGGCACCCTCTACCTGGC
ATATGCCAAACTTCCAGACTCCTGGAAAGAAAGCCCGTGTTCAGCATAAACCATTTTGTT
CACATAAATAGCTGAGGCAAAGATAGCCACTCTTGACATTCAGGGAATGGTGGGAATTCT
TCTGAAATCTTAGTTCCCAGACACCAGCCACGGGCCAACATTGTAAGCAGGCCTTTCTGA

26375 CTGAGGCAAAGATAGCCACTCTTGACATTCAGGGAATGGTGGGAATTCTTCTGAAATCTT
AGTTCCCAGACACCAGCCACGGGCCAACATTGTAAGCAGGCCTTTCTGAGGAGAGCTTGC
TACATCAACTCTTTTCTCCACAGCTGTCATCATTGTTATTAATTATTGTCAAGGGTTGCA
CAGCCAGTGTCTGACCAAAATGTGTACTCCATTGTTTTTTTGAGATGGAGTCCCGCTCTG
TTGCCCAGACTGGAGTGCGGTGGCACGATCTCAGCTCACTGCAACCTCTGACTCCTGGGT
[A,T]
CAAGCAATTCTCTTGCCTCAGCCTCCCGAGGAGCTGGGATTACAGGCACCCACCACCACA
CCCGGCTAATTTTTTTGTATTTTTAGTAGAGTCAGGGTTTTGCCATGTTGGCCAGGTTGG
TCTTGAACTCCTGACCTTGGGTGATCTGCCCACCTTGGCCTCCCAGAGTGCTGGGATTAC
AGGCGTGAGCCACCATGCCCGGCCAATGTGTACCTTTATTGCTACACCATGGAGTTGAAT
ATTATTATGTATAAATAACTATTGGTTTCATACAATAGAAGATTTCTGGTCTATGAAGCA

26693 TCAGCCTCCCGAGGAGCTGGGATTACAGGCACCCACCACCACACCCGGCTAATTTTTTTG
TATTTTTAGTAGAGTCAGGGTTTTGCCATGTTGGCCAGGTTGGTCTTGAACTCCTGACCT
TGGGTGATCTGCCCACCTTGGCCTCCCAGAGTGCTGGGATTACAGGCGTGAGCCACCATG
CCCGGCCAATGTGTACCTTTATTGCTACACCATGGAGTTGAATATTATTATGTATAAATA
ACTATTGGTTTCATACAATAGAAGATTTCTGGTCTATGAAGCATTTTAGAGGAAATTAAA
[C,T]
GATGTTTATGTTAATTTTAAAAAGCAAGAGATAAAATTTCATATCAATATGACCTCAACT
TTGTAAAATAAACATCATTTTTAAAAGAGATCAGAAGGAGCTATACCTCTGAGTGGTAAA
ATTATACATATTTTCCCCTGTCTTTATAACTTCCTATACCTTCCAGTTTTTTTATTATGA
GTAAACATTATTTTGATAATAAGACAGAATTAAAACAAAATAAAAACTTGTTTTAAATAA
CATGGCATCTTGTTGAATAACTGCAGTATCTGCTCATGAAAGATTAGTTGATGAAAACAA

30477 TACAGACGTGTGCCACTATGCCCAGCTAATTTTTGTATTTTTGGTAGAGATGGGGTTTCA
CCATATTGGCCAGAATGGTCTCCATCTCTTGACCTCGTGATCCACCTGCCTGGGCCTCCC
AAAGTGCTGGGATTACAGGTGTGAGCCATGGCGCCCGGCCCCGGCTAATTTTTATACTTT
TAGTAGAGACAGGGTTTCACCATGTTGGTCAGACTGGTCTCGAACTCCTGACCTTGCGAT
CAGCCTGCCTCGGCCTCCCAAAGTGCTGGTATTACAAGCATAAGCCACTGCACCCAGCTG
[T,G]
TATATTCTTTTTCTTTAATTTTTTAATTAAAAAAAAAATTTTTGTGGGTACATAGTAAGT
GTATATATTTATGGGGTATATGAGATGTTTTGATACAGGCAAGCAATGTGAAATAAGCAC
ATCATGGAGAATAGGGTGTTTGTCCCCTCAAGTATTTATCCTTTGAGTTACAAACAACCC
AGTTATACTCTGTAACTTATTTCAAAATGTACAATTAAGTTACTATTGACCATAGGCAGT
CTATTGTGCTATCAAATAGTAGGTCTTATTCATTCTTTTGTTTTTTTAACCCATTAAGCT

30858 TGAGATGTTTTGATACAGGCAAGCAATGTGAAATAAGCACATCATGGAGAATAGGGTGTT
TGTCCCCTCAAGTATTTATCCTTTGAGTTACAAACAACCCAGTTATACTCTGTAACTTAT
TTCAAAATGTACAATTAAGTTACTATTGACCATAGGCAGTCTATTGTGCTATCAAATAGT
AGGTCTTATTCATTCTTTTGTTTTTTTAACCCATTAAGCTATGGTATATTCTGACAGACC
TATCTGCACATGTTCATGAGGTACAAGCTTATTGTTTGGAGTCCACAAATTTTGTACTTA
[A,C]
AATGAAGTATTCTGTACTGAGCATTATAATGGTATTTTGTTGGACAACTTCTAGTTTTTA
TATTTTATGAAACAATGCTGTATGCTCTTATAAGTATACTTTAGGCTTAATTTTCTTTTT
ATAACTGAAATTCTTCTAATTTCTAATAAATAAGATTTTTCTGTATAGGAAAAGTGAGTA
ACATAGCAACAGAAAACACTCTGCATTTAATATTCTTAATTCTAACATATTATGTATAGG
ATTGAGAAGTTTTTATGATATAATAATTGATATTTCCCTAGTGATTCTTTGTGTTTAATT

31028 ATCAAATAGTAGGTCTTATTCATTCTTTTGTTTTTTTAACCCATTAAGCTATGGTATATT

FIGURE 3AA

CTGACAGACCTATCTGCACATGTTCATGAGGTACAAGCTTATTGTTTGGAGTCCACAAAT
TTTGTACTTAAAATGAAGTATTCTGTACTGAGCATTATAATGGTATTTTGTTGGACAACT
TCTAGTTTTTATATTTTATGAAACAATGCTGTATGCTCTTATAAGTATACTTTAGGCTTA
ATTTTCTTTTTATAACTGAAATTCTTCTAATTTCTAATAAATAAGATTTTTCTGTATAGG
[A,G]
AAAGTGAGTAACATAGCAACAGAAAACACTCTGCATTTAATATTCTTAATTCTAACATAT
TATGTATAGGATTGAGAAGTTTTTATGATATAATAATTGATATTTCCCTAGTGATTCTTT
GTGTTTAATTATTTGAATTCACTTCAGCAGAGTGTTGAATCTTTTAGGTCATACTAGTGA
AATGCTTCTGGTATGTAAATGATAAAATGGCTACTGTCTTTTAATTAAAGAATTGTATTT
TTAAAGAAGGCTCATGGTTAAATTAAGAACCATTTGGAAGTGTATTTACTAAGTGTTTAC

37308 TAGTAAAGACAGGGTTTCACCATGTTGGCCAACCTGATCTTGAACTCCTGACCTCAGGTG
ATCTGCCCGCCTCAGCCTCCCAAAGTGCTGGGATTACAGGCATGAGCCACCATGCCTGGC
TCCATCTCCCAAGAAGGTCTCTAGAGTTGGCACAGATCACTGCTTCTTCAGAAGAGCTTC
CATGTTAGTCCCTTCTTTCTATGTCAGCCCTATACCTGCTTGTTAGTTGGTTCTTCAAAT
TCTCAGGTACCCTCTCACCAGGCAGCCACTGACCTCATGTGATCCACCTGCCTTGGCCTC
CTAAAGTGCTGGGACTACAGGCAAGAGCCACTATTCCCAGCCTTTCTTTCTTTTTTTTTT
[-,T,G]
TTAGAAAGATTTTGTTTTTATTTCCATCAGAATGTCATATATGTTACACAAATCAAATCT
GTTGACATCTCAAGCTTATAACAATTACGTGTTCTTATAAATTACGTGGGAATTACATGT
ACTGTGAGAAGTGTTGTAATTATGATGTAATGTATATTATAATTTAGCCTACAGAAGTAA
CAAAGTCTTGTAATTAAATAAAGCAATAAATGTGTTGATAGATTATTACAATTGATAAGT
AATTGATAAATTATCTTCTTTTTCCTGTAACCCTTCTTCATCTCAAGTCTGATCTAGCTT

44213 GAGTGCAGTTGAACTGATTCTTAAAAATCTCTTAAAGGCGCCACATTGGAAATTCATCCT
ACATGAAATAGCCAGCCTGTGTTTGGAAACCATGTTGTAAGAAAGACACATGGCTATTGA
AACACTAGGAACACACTCAGTGCCCTGGAATGCTCTCCTAGGAGAAGCTTGCAGGCACTG
AGACAGCTGTCTCCCATCCCACATGCACTTGGCCACACACTCATTGAGTAGAGCTACCAT
[G,A]
CTGCTGAAATTGATCTCTCTCTCTCTTTCTCCCACCGCAGTGCATACAGATAAATTCATA
TAAGTCAAATGAATGTATGGTGCAATTCAGTTGTGTTTGCCAGGCCATGAACTAGAGCTT
TCACATACTGTATTAGTCTGCTCTCATACTGCTAATAAAGACATACCCAAGACTGGGTAA
TTTATAAAGAAAAAGAGGTGTAATAGACGCACAGTTTCACATGGCTGGGGAGGCCTCACA
ATCATGGCAGAAGGCAAAGGAGGAGCAAAGTCATGCCTTACATGAAGGCAGGCAAGAGAG

54046 GTTATTAAATCAATCATCAGATTTAACGCAGAAATCAACTCATGTAAACATACAGTGAGA
GAATTGTATTTTTCTCTAAATTTTCAGGACATTGAAAAAGACTTGAAACAAATGAGGCTT
CAGAACACAAAGGAAAGTAAAAATCCAGAACAGAAATATAAAGCTAAGGTAAGAAATACT
TTTGTCTTTGGGTTCCATATTAAATAGCTGGCTGGGGAGCCACCTTGTGATCTCGGTTGC
CTGCATGATTTTCCCCCTAGTATTTTATAGAATTGCTCTATTTTGTGATATGAGACCAAT
[G,A]
GTTTTAAGAATCTATAATGTCAAACAAAATTGACCTAGGGAGTTGTAATTTTAAGGCTTT
TACTGAATTGCTAAACTTTTTTTTTTTTTTTGCTTTCTCCTAGAAGGGGGTAAAATTTGA
AATTAATTTAGACAAATGTATTTCTGATGAAAACATCCTCCAAGAGGAAGAGGTATGCCA
TTAAGTCTAAATTTCCATTAGTAGGTATCAGAAAATGCATATATCTTAATAGCATGTTTC
ATGAAATTATTTCACAGGCTGTAGGGATAATTTTTTTCAACTTTTATTTTAGATTCAGGT

56598 TCTTTTCTTATTTGGATGCCTAGAATTTTAGAAAATATTTCTAGAAAAATGTTTGGTGCT
CAAGGCCAGGGAACGGTGGCTCACAGCTGTAATCCCAGCACTTTGGGAGGCTGAGACGGG
CAGATCATGAGATCAGGAGATTGAGACCATCCTGGCTAACATGGTGAAACCCCATCTCTA
CTAAAAATACAAAAAATTAGCTGGGTGTGGTGTCACCCACCTGTAGTCTCAGCTACTTAG
GAGGCTGAGGCAGGAGAATCACTTGAACCCAGGAGGCAGAGGTTGCAGTGAGCTGAGATC
[A,G]
CTGTACTGCACTCGAGCCTGGGCAACAGAGTGAGACACTGTCTCAAAAAAAAAAAAAAGGG
AAAGAAAAATGTTTGGTGTTCAAATGAGTCCTCCAAATACTTTTTATTCTCCCATTTTTAT
TTTATTGGTGTTATTTCTTTAGATAAATTATTACATTTTAATTTACTTTTCTTTAAATAA
AAGAGCTATTTTTACTCATAATATTAATTTTTATCATAGCCAAATTAAAATAGAAGACCTG
ATACATTGTCAACAACTAATATACTGACCTAAAAAATTGAACAGGTACCCTGAAACCAGG

56759 TGGTGAAACCCCATCTCTACTAAAAATACAAAAAATTAGCTGGGTGTGGTGTCACCCACC
TGTAGTCTCAGCTACTTAGGAGGCTGAGGCAGGAGAATCACTTGAACCCAGGAGGCAGAG
GTTGCAGTGAGCTGAGATCGCTGTACTGCACTCGAGCCTGGGCAACAGAGTGAGACACTG
TCTCAAAAAAAAAAAAAAGGGAAAGAAAAATGTTTGGTGTTCAAATGAGTCCTCCAAATAC
TTTTTATTCTCCCATTTTATTTTATTGGTGTTATTTCTTTAGATAAATTATTACATTTTA
[A,T]
TTTACTTTTCTTTAAATAAAAGAGCTATTTTTACTCATAATATTAATTTTTATCATAGCCA
AATTAAAATAGAAGACCTGATACATTGTCAACAACTAATATACTGACCTAAAAAATTGAA
CAGGTACCCTGAAACCAGGCACATTTATTTTAGGTCTTAATTAGTTATTGATAACTTTAA
GTAAATCTCATTTATGCATTTGGGCTCTCCTTGCCACAGCAAGGAGTAAATACAGTAAAT
CCAATACAGTAAATCCAAATTTCATTTTATTAGTTGATTTCAAAATCTTTTTTTATCCTG

FIGURE 3BB

58510 CTGAGATCCAGCCCTCCTCTCCTGCTCCATACCCACTCCCTCTTGCAGCTTTGGCTTCTC
CCAGGAGCTCCAGACTTACCAGTCTTTCTCATTGTCTTCTGGGAAGCTCCATGGACAAGT
GTTGCCAGTATCTGAAACTCAGCTGTGTAAAGTCAAGCTCTTCTGTGCTCTTCCCAGTGA
CCCTTTATTTTGGTTAGTGTCACAGATGCAACTGGCTGGGGCCAGTGTTGTGGGCAGTAA
AAGAATTTATCAACACAATTGTAAGTAAAGAAAGGCAGATTTATTAAAGTACAGAGATAC
[A,G]
TTGCAAGAGTGCAATGGGCAGCACAGCAGAGAAGAGGCTGTCTGCTAAGAGGCAGGGGCT
AGAGGGAAGTTTTATAGGGTCATATTGGAGGAGCTACATGCTGATAAGGTGTGCAGATAA
GGTTTTGCTGCTTGGGCTACATGTGGAAGGAATGAGGTATTTGGGAACAGGATGTGACAG
CAGCTTGTCTGTGATGAGTCATCTCTCAGAACAGTTGTTCCCCCATCCCCACCCCCAACC
TGGGACCCCTCCCTTTTTGTTGTTTACTTATCTTATGAGAACTTCACAGTCAGTGCTGTC

60356 CCTGAAATGTTAATCACTGTTTGAAGTGCGAGCTGGGTGGAGAGTCAGGGAGGTCCGCAC
TCCTCCAGGGCTTCACATGCCATCATTTTTGTGATTGAGAAGGATCATGCTGGCTGCAGA
GCAAAGGATGGCATGGAGGGCAAGACTGAAGGCAGGAGAAGAGTCCAAGTGCATGAGCCA
GAGTGGTGCAGGGAGAATAGATACTGAGTGTGGGAACTGAGGAAGAGAAGGGGCTCAAGG
ATATTCCCAGTTTTCTAATTCAAATGCATGAAGCTTTCATCAACCAAAAATACATCACAT
[G,A]
GAGGGTAATGGGGTCGGGAGAGACAAGGTAGTGATCTAAATTTGGAACATGTTGAGATTT
AGGTCTATAGAGCATCAGTTGCAGATTCTATATAAGACTGAAGGCCTGGGGCATATCAGG
GATAAAGATATAGCTTGGTGGCCCTTAGCATATCCGTGGTTTTTAACTTTGGTGATGGTC
AAAATACCTATGCAGAAGGACTGGAGTGAGAAGGAAATGGAGCTTAGGACATAACCCTAC
CACTATATAAACAAACTTTGGAGAATCAGGAGAGAGTAAAGCCAAAGGAGGAGAGACAGG

61643 TCTACTGAAAATGGCATGTTTGTTTTTTTCTTTATAAGACTGATTTAAATCAAACCTTTG
CCTGTAATATGTATTGCAAATGTTTTCCTCAGTTGGTTGTCAGATCTCATTTATAGTAAT
AACAGCAAATATATATGAGTGTGTGTGTGTGTGTGTGTGTGTGTGTGTGTGTATTTGTGT
ATTCATCCACTTAGGAATAAATTTTATGAGAATTGTGCGGCATATAGAAAGAAAACTGTA
AAACCTTACTGAGGTATTTACAGACCACTTGAATAAATGGAGAGAAATAACGGTGCTATA
[C,T]
ATTGGAAATATTTTTTCCAAATAAATATTGCAGTATCGTTGTCTGAGGTATTACCCAGAA
CTCTTTGTCTCACGACCAAAAGAATAAGGAGGGTGGACAGTAAGGGTGAGTTTGGACCGA
AAATTTAATAAACAAAAGAGGAAAGCTCTTCACTGTGGAGAGGGGACCCAAGAGGGTTGC
CATTTCACAGCTGAGTACAAAGGCTTTTATGAGGAACCTGATAGGGCTGGGGGTTTCATT
TGCATAAGGCATGAATTTCTGGCAGCTCCACCCTGTTCTCCTAGTATGCTGACTGGCTAG

62221 CTCCTAGTATGCTGACTGGCTAGGGGTTGTTTTTGGAAAAGGCACCACTCAGAAAATGAC
ATGATGGTTGACCAGGCATGGTAGTTCATGCCTGTAATCCCAGCACTTTGGGAGGCTGAG
GTGGGCAGATCTCTCAAGGCCAGGAGTTCGAGACTAGCCTGGCCAATATGGCTAAAGCCC
ATCTCTACTAAAAATACAAAAATTAGCCAGGTGTGGTGGTGCACACCTGTAATCTCAGCT
ACTTGGGAGGCTGAGCCACAAGAATCACTTGGACCTGGGAGGTGAAGGTTGCAGTGAGAC
[G,A]
AGATTGTGCCACCACACTCCAGTCACACTCCAGCTGGGTGACAGAGCAAGCAAGACTCCA
TCTCAAAAAAAAAAAAAAAAAAAATGACGTGGTGTAAAGACCAGTTGGAGCCTTGGCCCA
CAACCAGCTGAGTGTTGGAGTGATGGTTCACAGAGGCTTGGCTCACAGTCCAAAGTATGC
CCCAAAAAGGAAAGGAATGTGCTCACTGGGGCCCACCATGTACATGCCCACAAAAGGAGA
AGGAACTATTTGCTAGAGGCCCACTGATTGCACAAAGAACAAAGGCATTTCTGTGTTGGA

62306 TCATGCCTGTAATCCCAGCACTTTGGGAGGCTGAGGTGGGCAGATCTCTCAAGGCCAGGA
GTTCGAGACTAGCCTGGCCAATATGGCTAAAGCCCATCTCTACTAAAAATACAAAAATTA
GCCAGGTGTGGTGGTGCACACCTGTAATCTCAGCTACTTGGGAGGCTGAGCCACAAGAAT
CACTTGGACCTGGGAGGTGAAGGTTGCAGTGAGACGAGATTGTGCCACCACACTCCAGTC
ACACTCCAGCTGGGTGACAGAGCAAGCAAGACTCCATCTCAAAAAAAAAAAAAAAAAAAA
[A,-,T]
GACGTGGTGTAAAGACCAGTTGGAGCCTTGGCCCACAACCAGCTGAGTGTTGGAGTGATG
GTTCACAGAGGCTTGGCTCACAGTCCAAAGTATGCCCCAAAAAGGAAAGGAATGTGCTCA
CTGGGGCCCACCATGTACATGCCCACAAAAGGAGAAGGAACTATTTGCTAGAGGCCCACT
GATTGCACAAAGAACAAAGGCATTTCTGTGTTGGACTTTGCTCCCTTATCTGTGCAGCTG
TGGGCATGTTTTAGGCAAGCTTCCTGTGCTAGTTCCCTTATCTGTGTCTGCAGCTTGATT

63224 GAAAGTTAGAAACAGATCCTAGTATGTATCATAATTCAGCACAAATGAAAAGTAACATCA
CAAGTCAGCGTGAAAAGAAAGGATTATTCAGATAAATGCTGCTGGGCCAATTGGTTAACA
GTTTGGGGAAGATTGTGAAATCAGACCCTATATAATATGATACAACAAAATAAATTTTTT
AAAAAAGAGTTATATGTAAAAAGTTATACATTAGAAAATGAAATAAAAGAACATAGGTCA
TTTTTTTTTTTTTTTGAGACAGCGTCTCACTCTGTCACCAAGGCTGGAGTGCAAAGGCGT
[G,T]
ATCTCGGCTCACTGCAAACTCCGCCTTCTGGGTTCAAGCGATTCTCCTGCCTCAGCCTCC
CGAGTAGCTGGGACTACAGGCACCCGCTACCACGCCCAGCTAATTTTTATATTTTTGATA
GAGACGGGGTTTCACCATGTTGGCCAGGATGGTTTCGATCTCTTGACCTTGTGATCCGCC
CGCCTCGGCCTCCCAAAGTGCTGAGATTACAGGCGTGAGCCACTGCACCCGGCCGAGTTA
ATTTTTTTTGAACAGGGAAGAGCTATCTGTTCAAAATACATAGAAAAAAAAACCACAGAA

FIGURE 3CC

63350 GGAAGATTGTGAAATCAGACCCTATATAATATGATACAACAAAATAAATTTTTTAAAAAA
GAGTTATATGTAAAAAGTTATACATTAGAAAATGAAATAAAAGAACATAGGTCATTTTTT
TTTTTTTTTGAGACAGCGTCTCACTCTGTCACCAAGGCTGGAGTGCAAAGGCGTGATCTC
GGCTCACTGCAAACTCCGCCTTCTGGGTTCAAGCGATTCTCCTGCCTCAGCCTCCCGAGT
AGCTGGGACTACAGGCACCCGCTACCACGCCCAGCTAATTTTTATATTTTTGATAGAGAC
[G,A]
GGGTTTCACCATGTTGGCCAGGATGGTTTCGATCTCTTGACCTTGTGATCCGCCCGCCTC
GGCCTCCCAAAGTGCTGAGATTACAGGCGTGAGCCACTGCACCCGGCCGAGTTAATTTTT
TTTGAACAGGGAAGAGCTATCTGTTCAAAATACATAGAAAAAAAAACCACAGAATAAATT
AGTAATAATTCAACTTTAACAACAAAAAGCTGTAATAAAGCAAATCATACTAACCCCT

63517 AAGGCGTGATCTCGGCTCACTGCAAACTCCGCCTTCTGGGTTCAAGCGATTCTCCTGCCT
CAGCCTCCCGAGTAGCTGGGACTACAGGCACCCGCTACCACGCCCAGCTAATTTTTATAT
TTTTGATAGAGACGGGGTTTCACCATGTTGGCCAGGATGGTTTCGATCTCTTGACCTTGT
GATCCGCCCGCCTCGGCCTCCCAAAGTGCTGAGATTACAGGCGTGAGCCACTGCACCCGG
CCGAGTTAATTTTTTTTGAACAGGGAAGAGCTATCTGTTCAAAATACATAGAAAAAAAAA
[C,A]
CACAGAATAAATTAGTAATAATTCAACTTTAACAACAAAAAGCTGTAATAAAGCAAATCA
TACTAACCCCT

FIGURE 3DD

ISOLATED HUMAN KINASE PROTEINS

RELATED APPLICATIONS

The present application is a divisional of U.S. Application Ser. No. 09/873,404, filed on Jun. 5, 2001 and issued on Dec. 31, 2002 as U.S. Pat. No. 6,500,656, which is a continuation-in-part of U.S. Application Ser. No. 09/824,583, filed on Apr. 3, 2001 now abandoned.

FIELD OF THE INVENTION

The present invention is in the field of kinase proteins that are related to the serine/threonine kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high-energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks NK (1992) *Annu. Rev. Cell. Biol.* 8:463–93). Regulation of PTK activity may therefore be an important strategy in controlling some types of cancer.

Kinase proteins, particularly members of the serine/threonine kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the serine/threonine kinase subfamily.

SUMMARY OF THE INVENTION

The present invention is based in part on the identification of amino acid sequences of human kinase peptides and proteins that are related to the serine/threonine kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in lung carcinoma and placenta.

DESCRIPTION OF THE FIGURE SHEETS

FIGS. 1A–1B provide the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in lung carcinoma and placenta.

FIGS. 2A–2C provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3DD provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 33 positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the serine/threonine kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the serine/threonine kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the serine/threonine kinase subfamily and the expression pattern observed. Experimental data as provided in FIG. 1 indicates expression in lung carcinoma and placenta. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known serine/threonine kinase family or subfamily of kinase proteins.

Specific Embodiments

Peptide Molecules

The present invention provides nucleic acid sequences that encode protein molecules that have been identified as being members of the kinase family of proteins and are related to the serine/threonine kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in lung carcinoma and placenta. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988*; Biocomputing: Informatics and Genome Projects*, Smith, D. W., ed., Academic Press, New York, 1993*; Computer Analysis of Sequence Data, Part* 1, Griffin, A. M., and Griffin, H. G., eds., Humana Press, New Jersey, 1994*; Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on chromosome 13 by ePCR, and confirmed with radiation hybrid mapping.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on chromosome 13 by ePCR, and confirmed with radiation hybrid mapping. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in a gene encoding the kinase proteins of the present invention. Thirty-three SNPs were identified. The changes in the amino acid sequence that these SNPs cause can readily be determined using the universal genetic code and the protein sequence provided in FIG. 2 as a base.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in lung carcinoma, as indicated by virtual northern blot analysis, and placenta, which is the cDNA library source from which the cDNA clone came from. A large percentage of pharmaceutical agents are being developed that modulate the activity of kinase proteins, particularly members of the serine/threonine kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in lung carcinoma and placenta. Such uses can readily be determined using the information provided herein, that which is known in the art, and routine experimentation.

The proteins of the present invention (including variants and fragments that may have been disclosed prior to the present invention) are useful for biological assays related to kinases that are related to members of the serine/threonine kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in lung carcinoma, as indicated by virtual northern blot analysis, and placenta, which is the cDNA library source from which the cDNA clone came from.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in lung carcinoma and placenta. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in lung carcinoma, as indicated by virtual northern blot analysis, and placenta, which is the cDNA library source from which the cDNA clone came from.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in lung carcinoma and placenta. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in lung carcinoma and placenta. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in lung carcinoma and placenta. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in lung carcinoma, as indicated by virtual northern blot analysis, and placenta, which is the cDNA library source from which the cDNA clone came from. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in lung carcinoma and placenta. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in lung carcinoma and placenta. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in lung carcinoma and placenta. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof.

The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 13 by ePCR, and confirmed with radiation hybrid mapping.

FIG. 3 provides information on SNPs that have been found in a gene encoding the kinase proteins of the present invention. Thirty-three SNPs were identified. The changes in the amino acid sequence that these SNPs cause can readily be determined using the universal genetic code and the protein sequence provided in FIG. 2 as a base.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45° C., followed by one or more washes in 0.2×SSC, 0.1% SDS at 50–65° C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 33 positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 13 by ePCR, and confirmed with radiation hybrid mapping.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in lung carcinoma, as indicated by virtual northern blot analysis, and placenta, which is the cDNA library source from which the cDNA clone came from. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in lung carcinoma, as indicated by virtual northern blot analysis, and placenta, which is the cDNA library source from which the cDNA clone came from.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in lung carcinoma and placenta. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in lung carcinoma, as indicated by virtual northern blot analysis, and placenta, which is the cDNA library source from which the cDNA clone came from. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in lung carcinoma and placenta.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in a gene encoding the kinase proteins of the present invention. Thirty-three SNPs were identified. The changes in the amino acid sequence that these SNPs cause can readily be determined using the universal genetic code and the protein sequence provided in FIG. 2 as a base. As indicated by the data presented in FIG. 3, the map position was determined to be on chromosome 13 by ePCR, and confirmed with radiation hybrid mapping. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in a gene encoding the kinase proteins of the present invention. Thirty-three SNPs were identified. The changes in the amino acid sequence that these SNPs cause can readily be determined using the universal genetic code and the protein sequence provided in FIG. 2 as a base.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in lung carcinoma, as indicated by virtual northern blot analysis, and placenta, which is the cDNA library source from which the cDNA clone came from. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in a gene encoding the kinase proteins of the present invention. Thirty-three SNPs were identified. The changes in the amino acid sequence that these SNPs cause can readily be determined using the universal genetic code and the protein sequence provided in FIG. 2 as a base.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. Coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharnacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amarm et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufinan et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of S. cerevisiae (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated polypeptide having an amino acid sequence comprising SEQ ID NO:2.

3. A composition comprising the polypeptide of claim 1 and a carrier.

4. A composition comprising the polypeptide of claim 2 and a carrier.

* * * * *

SEQUENCE LISTING

<160> NUMBER OF SEQ ID NOS: 4

<210> SEQ ID NO 1
<211> LENGTH: 2370
<212> TYPE: DNA
<213> ORGANISM: Human

<400> SEQUENCE: 1
cattggagac catggataag tacgatgtga ttaaggccat cgggcaaggt gccttcggga 60
aagcatactt agctaaaggg aaatcagata gcaagcactg tgtcataaaa gagatcaatt 120
ttgaaaagat gcccatacaa gaaaaagaag cttcaaagaa agaagtgatt cttctggaaa 180
agatgaaaca tcccaacatt gtagccttct tcaattcatt tcaagagaat ggcaggctgt 240
ttattgtaat ggaatattgt gatggagggg atctcatgaa aaggatcaat agacaacggg 300
gtgtgttatt tagtgaagat cagatcctcg gttggtttgt acagatttct ctaggactaa 360
aacatattca tgacaggaag atattacaca gggacataaa agctcagaac atttttctta 420
gcaagaacgg aatggtggca aagcttgggg actttggtat agcaagagtc ctgaataatt 480
ccatggaact tgctcgaact tgtattggaa caccttacta cctgtcccca gagatctgtc 540
agaataaacc ctacaacaat aaaacggata tttggtctct tggctgtgtc ttatatgagc 600
tctgcacact taaacatcct tttgagggta acaacttaca gcagctggtt ctgaagattt 660
gtcaagcaca ttttgcccca atatctccgg ggttttctcg tgagctccat tccttgatat 720
ctcagctctt tcaagtatct cctcgagacc gaccatccat aaattccatt ttgaaaaggc 780
cctttttaga gaatcttatt cccaaatatt tgactcctga ggtcattcag gaagaattca 840
gtcacatgct tatatgcaga gcaggagcgc cagcttctcg acatgctggg aaggtggtcc 900
agaagtgtaa aatacaaaaa gtgagattcc ggggaaagtg cccaccaaga tcaaggatat 960
ctgtgccaat taaaaggaat gctatattgc atagaaatga atggagacca ccagctggag 1020
cccagaaggc cagatctata aaaatgatag aaagacccaa aattgctgct gtctgtggac 1080
attatgatta ttattatgct caacttgata tgctgaggag gagagcccac aaaccaagtt 1140
atcaccctat tcctcaagaa aatactggag ttgaggatta cggtcaggaa acgaggcatg 1200
gtccatcccc aagtcaatgg cctgctgagt accttcagag aaaatttgaa gctcaacaat 1260
ataagttgaa agtggagaag caattgggtc ttcgtccatc ttctgccgag ccaaattaca 1320
accagagaca agagctaaga agtaatggag aagagcctag attccaggag ctgccattta 1380
ggaaaaacga aatgaaggaa caggaatatt ggaagcagtt agaggaaata cgccaacagt 1440
acctcaatga catgaaagaa attagaaaga agatggggag agaaccagag gacattgaaa 1500
aagacttgaa acaaatgagg cttcagaaca caaaggaaag taaaaatcca gaacagaaat 1560
ataaagctaa gaaggggggta aaatttgaaa ttaatttaga caaatgtatt tctgatgaaa 1620
acatcctcca agaggaagag gcaatggata taccaaatga aactttgacc tttgaggatg 1680
gcatgaagtt taaggaatat gaatgtgtaa aggagcatgg agattataca gacaaagcat 1740
ttgaaaaact tcactgccca gaagcagcat ttacagaact gacttggctc agtttcctct 1800
tcctggaata ctctctgcct catttccttc tggaaaaatc tccattcagc aggcatctta 1860
ttgaggatct cctttgtgcc aacgactgct cactgaagga ctggagtgag aaggaaatgg 1920
agcttaggac ataaccctac cactacataa acaaactttg gagaatcagg agagagtaaa 1980
gccaaaggag gagagacagg tcatggggag gcacaggaat tggcagcatc aactggaaga 2040

-continued

```
gaaaggccag atgagggttt tccacgcaga ctgtagttgc tgtgggaaac aggaggcagt   2100

gggatggagg agcgcctcag actctgctgc agatgatggc agtggccgac atcacctcca   2160

cctgccccac ggggcctgac agtgagtctg tgcttagtgt cagtcgtcag gaagggaaga   2220

ccaaggaccc gtacagccca gtgctcatcc tgatgtgata gtctacttct cactatacac   2280

cctatagatc ttgtatcaga cactttcaaa tatgttgttt tgatatctca agaaaaaaaa   2340

aaaaaaaaca ctgtcatgcc gttacgagcg                                    2370


<210> SEQ ID NO 2
<211> LENGTH: 640
<212> TYPE: PRT
<213> ORGANISM: Human

<400> SEQUENCE: 2

Met Asp Lys Tyr Asp Val Ile Lys Ala Ile Gly Gln Gly Ala Phe Gly
 1               5                  10                  15

Lys Ala Tyr Leu Ala Lys Gly Lys Ser Asp Ser Lys His Cys Val Ile
            20                  25                  30

Lys Glu Ile Asn Phe Glu Lys Met Pro Ile Gln Glu Lys Glu Ala Ser
        35                  40                  45

Lys Lys Glu Val Ile Leu Leu Glu Lys Met Lys His Pro Asn Ile Val
    50                  55                  60

Ala Phe Phe Asn Ser Phe Gln Glu Asn Gly Arg Leu Phe Ile Val Met
65                  70                  75                  80

Glu Tyr Cys Asp Gly Gly Asp Leu Met Lys Arg Ile Asn Arg Gln Arg
                85                  90                  95

Gly Val Leu Phe Ser Glu Asp Gln Ile Leu Gly Trp Phe Val Gln Ile
            100                 105                 110

Ser Leu Gly Leu Lys His Ile His Asp Arg Lys Ile Leu His Arg Asp
        115                 120                 125

Ile Lys Ala Gln Asn Ile Phe Leu Ser Lys Asn Gly Met Val Ala Lys
    130                 135                 140

Leu Gly Asp Phe Gly Ile Ala Arg Val Leu Asn Asn Ser Met Glu Leu
145                 150                 155                 160

Ala Arg Thr Cys Ile Gly Thr Pro Tyr Tyr Leu Ser Pro Glu Ile Cys
                165                 170                 175

Gln Asn Lys Pro Tyr Asn Asn Lys Thr Asp Ile Trp Ser Leu Gly Cys
            180                 185                 190

Val Leu Tyr Glu Leu Cys Thr Leu Lys His Pro Phe Glu Gly Asn Asn
        195                 200                 205

Leu Gln Gln Leu Val Leu Lys Ile Cys Gln Ala His Phe Ala Pro Ile
    210                 215                 220

Ser Pro Gly Phe Ser Arg Glu Leu His Ser Leu Ile Ser Gln Leu Phe
225                 230                 235                 240

Gln Val Ser Pro Arg Asp Arg Pro Ser Ile Asn Ser Ile Leu Lys Arg
                245                 250                 255

Pro Phe Leu Glu Asn Leu Ile Pro Lys Tyr Leu Thr Pro Glu Val Ile
            260                 265                 270

Gln Glu Glu Phe Ser His Met Leu Ile Cys Arg Ala Gly Ala Pro Ala
        275                 280                 285

Ser Arg His Ala Gly Lys Val Val Gln Lys Cys Lys Ile Gln Lys Val
    290                 295                 300

Arg Phe Arg Gly Lys Cys Pro Pro Arg Ser Arg Ile Ser Val Pro Ile
```

-continued

```
305                 310                 315                 320

Lys Arg Asn Ala Ile Leu His Arg Asn Glu Trp Arg Pro Pro Ala Gly
                325                 330                 335

Ala Gln Lys Ala Arg Ser Ile Lys Met Ile Glu Arg Pro Lys Ile Ala
            340                 345                 350

Ala Val Cys Gly His Tyr Asp Tyr Tyr Tyr Ala Gln Leu Asp Met Leu
        355                 360                 365

Arg Arg Arg Ala His Lys Pro Ser Tyr His Pro Ile Pro Gln Glu Asn
    370                 375                 380

Thr Gly Val Glu Asp Tyr Gly Gln Glu Thr Arg His Gly Pro Ser Pro
385                 390                 395                 400

Ser Gln Trp Pro Ala Glu Tyr Leu Gln Arg Lys Phe Glu Ala Gln Gln
                405                 410                 415

Tyr Lys Leu Lys Val Glu Lys Gln Leu Gly Leu Arg Pro Ser Ser Ala
            420                 425                 430

Glu Pro Asn Tyr Asn Gln Arg Gln Glu Leu Arg Ser Asn Gly Glu Glu
        435                 440                 445

Pro Arg Phe Gln Glu Leu Pro Phe Arg Lys Asn Glu Met Lys Glu Gln
    450                 455                 460

Glu Tyr Trp Lys Gln Leu Glu Glu Ile Arg Gln Gln Tyr Leu Asn Asp
465                 470                 475                 480

Met Lys Glu Ile Arg Lys Lys Met Gly Arg Glu Pro Glu Asp Ile Glu
                485                 490                 495

Lys Asp Leu Lys Gln Met Arg Leu Gln Asn Thr Lys Glu Ser Lys Asn
            500                 505                 510

Pro Glu Gln Lys Tyr Lys Ala Lys Lys Gly Val Lys Phe Glu Ile Asn
        515                 520                 525

Leu Asp Lys Cys Ile Ser Asp Glu Asn Ile Leu Gln Glu Glu Glu Ala
    530                 535                 540

Met Asp Ile Pro Asn Glu Thr Leu Thr Phe Glu Asp Gly Met Lys Phe
545                 550                 555                 560

Lys Glu Tyr Glu Cys Val Lys Glu His Gly Asp Tyr Thr Asp Lys Ala
                565                 570                 575

Phe Glu Lys Leu His Cys Pro Glu Ala Ala Phe Thr Glu Leu Thr Trp
            580                 585                 590

Leu Ser Phe Leu Phe Leu Glu Tyr Ser Leu Pro His Phe Leu Leu Glu
        595                 600                 605

Lys Ser Pro Phe Ser Arg His Leu Ile Glu Asp Leu Leu Cys Ala Asn
    610                 615                 620

Asp Cys Ser Leu Lys Asp Trp Ser Glu Lys Glu Met Glu Leu Arg Thr
625                 630                 635                 640
```

<210> SEQ ID NO 3
<211> LENGTH: 63588
<212> TYPE: DNA
<213> ORGANISM: Human
<220> FEATURE:
<221> NAME/KEY: misc_feature
<222> LOCATION: (1)...(63588)
<223> OTHER INFORMATION: n = A,T,C or G

<400> SEQUENCE: 3

```
cttggcaggc cgccgctgtg gcccaaagag taggaagccg ttccagtctc acgtccacct     60

tttggcaata tttgagacct tgtacaagaa acactcttcc tgtatcagtt tagctcattt    120

gtaaaactgg gagactactg ccttgacggg ttgtaaagaa aagagagaac gtttgcgaag    180
```

-continued

```
cgtctggtgc accttaagca agagcgggga gcgctactgt agactgcaaa gcaaaggaat    240
cccgacccaa ggcaacggga cggttgcggg gtgactctgc cgggtctcca aactccctgg    300
cgcctgaccc tgcctcgagg tggactggtc cccaggccat tccagacccg cgccccgccc    360
gcgtttcctt gcgcggctcc gccccggccg cagggaggcg cagcggcccc gggaacccgg    420
atccttccgg gacgcttcgt tggccccgcg gagccggcgg agcaggtacg cttgcagggg    480
ccgcccttag ttcttgcccg gagccgccac agggcttcgg gagctcggca gggtggggga    540
aagggatgga gtttcggcct ggggcggcgg gggcggccca gaaaaggcct agcgtcctgg    600
gctgtgtggg tgtagcgtcc agggcgcgtc ggtctctatg gcaacgctcc acacgcggag    660
gtcgggtacg ggtaagcgtc ttgccactca cccgcggccg cttccagggg cggccctagg    720
ggagaaggaa ttttcctaat ttgggggctt ccaccctttg gtgccacttg ggcgggaggg    780
tcgcgggccc tcagttcccg gcgagtcacc cccggcccca agtccgtatg cgtctctctc    840
agaacccgat cctccggtgt ctgcagcctc tcctggctgc ggagctggtt cccagccccc    900
tgcaacccag taccgacttc ccaccctgac gtaaaattat tcgaaaacaa gccccctgct    960
caccccatta acaacaacaa caaaactgta ttatgcccta actgtagcat aaagaggaaa   1020
tagaaggaaa gcaataagta agaaagtaca tatttcaatc tgaaaatgct tggcactact   1080
acccttggaa aatgtagaga agtagccagt agccgcgcct ggggagtcgc ctgaacgtga   1140
cggcagcaaa tgcagattgt tgggtctccg ggaccaggag cagcgtggcc agtgaagcgc   1200
gtggttttcc caaatggtga acaattcttg gtaaacctcc aaaccgaagt gcaatcaagc   1260
cttgatttac atgtagttgc attcctcgaa aaaaaaaaga agtgttcatt aaaactgcaa   1320
aaatacttag catttcgatg taaaatagag tttggttcta gccacaaacg gatttttcca   1380
cgcacaggaa tgtataggaa gactctccaa gattgtaggg ccgcggggta atcctttatt   1440
gtgcgggact gtctctcgaa tcgcagaatc ctaccatctc aggccccaac cacctgtaaa   1500
cctcatgcct ctgaatcttg gggaaacagc ttccccaccc ccatatattt ccagaattcc   1560
ccctaggggg cagtacgtcc ccactaagaa aggctgaact ataaaagtgc acaagcctaa   1620
ggacattcct gctttataaa ggtgcgaaac accggatata gtatctttca ttctcagaac   1680
aaacttgcaa aacaggtatt gttattccat tttagaaatt aggaaagtga ggttttgcca   1740
ggttaagtga cttacccgag aatacagggc aaaagtgtat caaagctgag ctatgacccg   1800
tgtctgacca agaaactctg tctcatttca gttatctgtg gccacaaaga aagttatttg   1860
tctctgtctt ggcaaggctg ggaggaaagt tttagctaag tgagttcttt tacactttag   1920
tcatcagttt tctgactttg ttagtcttta tgagacgtgt gtgataaatt tacattactc   1980
taattccagg aaactcagcc cattggagac catggataag tacgatgtga ttaaggccat   2040
cgggcaaggt gccttcggga aagcatactt agctaaaggg aaatcagata gcaagcactg   2100
tgtcataaaa gagatcaatt ttgaaaaggt aaagttaagt tcaaatttct gttaattttc   2160
agtgggatat tcagctggct tttaatccaa tataaaaagg aaatttttat tttttataat   2220
ttcgaatttt aagccataat tgatttttgt taattcaacc tcctaagtcc attgtccaaa   2280
cagcaaccaa tgatctcatt tttaaaaaga ggctggacgc actggctcac ccctgtaatc   2340
ccagcacttt ggatggccaa ggtgggagga ttgtgtgaag ccaggagttc gagatagcct   2400
gggcaacata gcaagaccct gtccctgcta aaaaaaaatt tttttaatga aaatagaaaa   2460
gaaataagat cacatccctg tggctcctat ggccctcctt agggtgccct gcaaggccct   2520
```

-continued

```
gtgagatgcc agcctcctct gttgccctga cttttctctg tggtgcactt cctctctcct   2580
tattcaggtc ctctacgagg ggttttctgc aaacatccta gctagagtag acccccagcc   2640
acaatcacac cttatcacct tatcacacca ccttggttcc tggtttcttt tttgttttct   2700
tttcttttct ttttttagac ggagtctcgc tctgtcacct aggctggagt gcagtggcat   2760
gatcttggct cactgcaatc tccacctccg ggattcaagc aattctccca cttcagcctc   2820
ctgaatagct gggactacag gtgcatgcca ccatgcctgg ataatttttt gtatttttag   2880
tagagatgga gtttcaccat gttgcccagg ctggtcttga actcctgagc tcaagtgatc   2940
tgcccgcctt ggcctcccaa agtgctggga ttacaggctt gagccactgc ttctggcctg   3000
gtttatttc ttactagcat gtataatgct ctgcaattac tttgctctct taattattca   3060
tttgtttatt gcttgtcttc ctcagtatgc agaacagttc ctgtcacata ataggtgcta   3120
aacacattta ttgagtgcac tgaatgaata gagaaaaact atatgtaatt gttggtctaa   3180
tgattttgga aaataaatat agttaattaa aaattaataa tttttgctaa atccaccttg   3240
gtcagtgttt atgtcaccct ctttagtgat atgttcattt cataatatat tgggacaaca   3300
atgtccattg tttgctagaa ttaattctaa ggcaagtctt gttggtcagc ttctagagga   3360
tttataaatg agagtagcat aaaaagttcc atacaaagtg tgtgcaaaat ggactaccca   3420
agttacacca tatgaatata cttaatgcca ttgaactgta cacttaaaaa tcgttaaaat   3480
gatataaatt ttatcttacc acaaaaaatt gcaagaaaac ctacccaaac ttaaagctca   3540
agagtagatg actggcttcc agggataatg atttatttcc caatataggt ctctttttgt   3600
gaatccatgg catattcata ataatgtcct cttattctag tggcccgcaa tagcttcctc   3660
ccatgacatt attctgctca ctctcttttg tttatctgac tgctctccct caggcttatc   3720
tctgtcttcg ccctgtgtat gtcctcaacc atgtgtcctt ttctgatttt ctttttctgt   3780
ccattgtcac ctaaactgcc ccacttcagt gtttaccaat aagtagatct ctcttaaatc   3840
tctgtctcta cccctggcat ctttcagtac cctagttctg catttcttct gccagctaga   3900
taacttcagg taatatctgt ggttttgttt tgaggtggag tctcgctctg tcgcccaggc   3960
tggagtgcag tggtgccatc tcggctcact gcaagctctg cctcccaggt tcatgccatt   4020
ctcctgcctc agcctcccga gtagctggga ctacaggcgc ccgccaccac gcctggctaa   4080
tttttgtat ttttagtaga gacggggttt cactgtgtta gctaggatgg tctcaatctc   4140
ctgacttcgt gatccacccg cctcggcctc ccaaagtgct gggattacag gcatgagcca   4200
ccacacccat ccaacatcta tgttattaat ctattgctgt gtagcatatt accccaaact   4260
tagtggctta aagaataaac atttattgtc tcagagatcc tgtgcatcaa gaatttagga   4320
tgacgatcat tgagaccacc ttggaggctc ggtatcacaa ttgtacccaa aaacaagtat   4380
taatagtgat tcttccttgt tgtaagcaga cccacttcac ctcctatgtg ctgcgctgta   4440
ttaatgtcat cagtgtcctt atggttgcca gcctgaaaac cttgggatcg tttgtgagct   4500
tattccttct ccacattcaa ttatttggcg aatactgttg actcttcctc ttccttgaat   4560
ttgcttcagt ccttttgtcg aggccctggg tcacttggat ccttcaagtg gctccagccc   4620
aattttgata atgctccagc catgcccccca aaccttcact gggacagagg ctgtaaagaa   4680
agagttgcct aggtttgact acataaaaat agaaaacgtt tgtatgtcaa aacaaacact   4740
ataaataaat tcaaagaaat cgagaaggtg ccaaaaatat ttgcaagtat tgacttaatg   4800
gtgttagcct tttattaaat caataaaaag ataaaatcca tatatgaagt catcgtacaa   4860
aaatttgaaa ctcagtagaa aactaagaaa ttaggagttt attcaaagaa aaaccccaca   4920
```

-continued

```
gataaacagt tagaaaacaa atgtccaaca gtaggtaatt tgttaagtaa tttataaaaa   4980
actaagtggc tattagcaat catgttgtag gtgaagcatt gacatgggaa aatttcaatg   5040
tttgcaatgt ttgagaaaat agtaagtgta aaataatata atctttggaa aaatatatat   5100
attctccata tatatgtata cctacaaata tgttcatata tgtacaaaga aagacacaaa   5160
ttgttattat tgaggtagaa agtggggttt gccttgtgca tttttttga gacaggattt    5220
cattctgttg cccaggcagg agtgcagtga catcatcatg gctcactgta accttgaaca   5280
agccatcctc ctgcctcagc ctcctgagta gctaggactg caggcatgcg ccaccacacc   5340
cagctaattt tgaaattgtt tttagagaca ggatcttgct atgttgccca ggctggcctc   5400
aagtgatcct cccactttgg cctcccaaag tgctgggatt acaggtgtta gccactgtgc   5460
ctggtctgcc ttgtgctttt atattgtttc actcttcaga gaagttttga gaccctctct   5520
gatttgctcc aaaactacag ctcctatcac ataccctact ttttttcccc actccagcct   5580
ctgcatttgc ttctggggct acttcttcca aggtcgttgc ctgctgatct cccagcatca   5640
agatcccact tgttcaaggc tgagctctac catacctcca gaatcctccc actctaaaga   5700
atttatcctt ctctgtaaac ttgcataact tttattggaa cctctgttat agtactgact   5760
gctttctttc tggacatgct ttggctgttt attttgtgcc ttctcctcct tatttagctg   5820
taatatgttc tgtgaggacc gagtccatgt gtgttttgtg ctggtattcc acacagcacc   5880
taatgcttgg tgccaggaga tattcaataa cttcttattg gatagatgat tcactggaca   5940
gatgctttca ggccctcttg ctctactgtg aagctggtat atacttagga attataaaac   6000
cattttaatt ctatgtaaag agaaaatatt tgagaggtga atctctataa aaatgtacat   6060
taacattact gcatttcata gcatctctcc cattctttag tataatcaaa aattgactat   6120
atttttctaa tagagcacca atttttcatc actttactca tgaactactc ttgtcactat   6180
gccataaata agtagaatct tatattagac ctcattattc ttgttttccc atatctgttt   6240
atgttatcga atttacctat aacatctgtg tcacaatatt aacatttatt acttctttct   6300
tcctatctac tctcatgtag tttttcatta cttcttatct agagaaattt atatttcttc   6360
tctctaatgc ctccctactc cctacactag accccagaac taaattgctt gttttcttac   6420
aggtaccaaa aagctaatat ttctcttatc atcctaccat tatcaagcat gttcttttcc   6480
ttctgggctc aaataaaagt gttttatctt tcctcaattg tgaaaataaa aatgttcgtt   6540
gtagaaattt tgaaaagagc caaaggagaa aataagacca tttagaggaa aataaaaata   6600
gcatataacc tctttcttaa tcactatgaa cactttgctg aatttctctc tagactattt   6660
ttaatgtata agtatataag ttattagaat gattggtgtc atggtagata tactcttttt   6720
ttttttgag acggagtctc gctctgttgc ccaggctgga gtgcagtggc gtgatctctg    6780
ctcactgcaa tctctgcctc ccaggttcaa acaattctcc tgcctcagcc tcctgagtag   6840
ctgggactac aggcgcatgc caccatgcct ggctaatttt tgtattttta gtagaaacag   6900
gctttcacta tgttggccag gctggtctcg aactactgac ttcgtgatct gcctgccttg   6960
gcctcccaaa gtgctgggat tacaggtgtg agccactgcg cccagcccag gtatactctt   7020
ttgtaacagt tttttatatt agcaatatat tgtgaatatt tcctcatctc attcaatatt   7080
tttatataat aaaatgttgt catttaatga tattaaatgt gttcacacta atgataaagg   7140
gaccacctgc agggtgtcca ttatatgtca caccatcctg ggtgttttat tatgtatatc   7200
aactcaattt aatcttcaca accacttaaa aggtagctct cattactctc actgtacaag   7260
```

-continued

```
tgaaagagct gaggctaaag aggttaagca gttagctcca ggatgcacag taatcagcag   7320
atccatctaa gtctttctct gctctttcca tgatactaca ttgcctccct ttatttttaa   7380
tgactgcata gcattaaagt ggtagcaggt caaaaatacc ataatttagc tgggcatggt   7440
ggcaagtgcc tgtagtccca gctattctgg aggatgagtt gggaggatcc cttgacccca   7500
ggagttaaaa tccagcttag acaacatagc agaactctgt cttaaaaaaa aaaaaaaagc   7560
tagcaaaaca cccctgtaat ttatttaact ctttttctat tttcagataa ttacattgtt   7620
tggttggttt tttggctacg attcaataac atttaatatg taaagtatga ttcattttta   7680
ttaaacaaaa ctatgtatat atgcttgcct atatatgcat gaaataaaaa gctctaacta   7740
ttaacaacag ttatccctag ggaatatagt attaggttgg cgcaaaagta attgcatttt   7800
tgccattaag agtaaggtta ccacctatgg gctttcgtct gtgggctaga tgagaaagaa   7860
agagggaagt ttcactttta ccttattcac ttctatttga cttaaaacaa gcgtgcatta   7920
ttagagtaac ttaaaaacta gcaataaaac actgtaacaa agtcttttgt atgagaactc   7980
ttctgtaccc ttttattatc ttctttggat aaatttctag aagaattagt caaaaatagg   8040
aacatttccc tcatgcctgt aatcccagca ctttgggagg ctgaggcagc tagatcactt   8100
gaggccagga gttcgagagc agcctgggca acatggtgag accccatctc tactaaaaat   8160
acaaaaaatt agccgggtat gatggtgctt gcctgtggtc tcagctactc aggaggctga   8220
ggtgggagga tcacttgagc tcagtgggca gaggctgcag tgaaccaaga tcatgccact   8280
gcactccagc ctgggtgata gagcaagacc ttgtcttaaa aaaaaaaaaa aaaagatttc   8340
ttcagcagga tacagacccc ccacaaaaat gaacatttta aagattcata ttatatattg   8400
taaaactgcc ttcccagaaa tattttatca atttgtgtag ttttaccaga aataaatgag   8460
tgtccatttt gctgctttct ggccaatagt agttattgac attcttttca tctttgccag   8520
tttcatacat ggaatactat attacatttt gttttagctt ttattccttt tttttttttt   8580
ttgcaatgga gtcttactct gtcacccagg ctggagtgca gtggtgtgat tttggcttac   8640
tgcagcctcc atctcccagg ttcaagggat tctcctgcct cagcctcctg agtagctgag   8700
accacaggtg tgtgccacca cgcctggcta attttttgtg tttttagtag agacagggtt   8760
ttgctatgtt ggccaggctg gtcttgaact cctggcctca agtgatctgc ctgccttggc   8820
ttcccaaaga gctgggatta caggcatgag ctaccacacc cagccaaatt ttgctttagt   8880
ttttattcct ttgattactg catgagattg aatatttttt ctatcagcca tttttatttc   8940
tctttttttt tcgagttgac tattcttgta ctttgctatt tttctgttgg ggtgtttgcc   9000
tttttaaaaa ttatttgcca tcaattttta tattataaat atatttgtca tatatggtac   9060
aaatattgta tcttatcctt ttgtttgtct tttaattttg tttataatat tcttttaaat   9120
aaatagtagt taggaatttt ttaagttgct aaatgtatcc agctggtagg agtaatttag   9180
ctgtttttgt tttgaaactc ctatgtactg actatacaat ttaaattggg gcaggaaaca   9240
ctgaagctta gaggggttta aggaacttac tgaaggatcc ttcagctgag atgtagggaa   9300
gctagaattg agaatattaa tttttaagaa gttcttaagt ctaaatgaga atgagaaatc   9360
tggccaatgt tgaagacctc taatgggtgg aggccccgtg gacatcagaa aagcggggca   9420
gtcaggggct ggaagtcagg gtagaaatga caagtcagca aagcatcaag agtgaggaag   9480
aaaaagtaga aatgaggtgt ggccactggt actggcacca aacccccttgg caagtattgt   9540
ctataggtga aagtagaaca agaaaataca cccaaatact tctaaaatga agtcatgcaa   9600
gacaattttt atttgaaaat gaaaaatgta gtcatcttaa tacaaaattt tactgacctg   9660
```

-continued atttctgtgg gatatgacac attttctttt tttagatttc atttgtttct tctcagcagt 9720
gattgctcct ggaatgttgc atttttataa agaattcctt cgctactgaa agatagatat 9780
taaaatatgg ctccatatgg ctagataatg aacacggtac caccagtcca acttttaata 9840
tagcaaaact tcaccagaaa tatttatttt cttgatgatg gttgtcaaca aaccattgat 9900
gagatgtagg gcactctgct aattctagaa atgttgtttc ctgccattga aagatcgttt 9960
tcaaagtgac attaaaagcc agtgaaatcc tagagaattt tagatggaaa tgagcagaaa 10020
gcatgttctt gaaaccaagt tagctttata gactactctg tctcttaatg taatttagat 10080
gcccatacaa gaaaaagaag cttcaaagaa agaagtgatt cttctggaaa agatgaaaca 10140
tcccaacatt gtagccttct tcaattcatt tcaaggtttg attttctaat attcgttaag 10200
tatttttata aagtataggc atgttgacat atgtaaaaag atttgttcct aaggactgtg 10260
tataaattaa tttttgtaaa tgggtcattt ccccatttac ttaaattgca gcttgagacg 10320
tcctcgttat ttcctctcta gtaagttttt gtagacggct ttcttatgtt ttcttgtttt 10380
tctgcctctc cttaattctc actctcccaa aaaattaatg actggcttat tagcttcttt 10440
gctgtagtaa caacccccaa atttaagtga cttacaataa gacacatcta tttctcactt 10500
acattacatg ctagctgtgg tgggctgggg tcttgagtct ggggcccagg ctgaaggagc 10560
agctcagata aggaaccagc tgttctcata agcaagagaa gaggggaaaa cacagagccc 10620
accacactat cgctctcaaa gccctgctag gatgtgtgtg tttgtgtgtg tgtgctgggg 10680
ggtactctgt ttacatgaga tcctgcatat cctcaggcaa cagatgggac tgtgtaatcc 10740
tcttacagag agccagcaaa cagccacgca ccatagccta gcacactgcc acggagaggg 10800
ggagaacttt agggaaggaa gtaccttcct ctgtacacct gaatacaatt ctgctgacaa 10860
ctttagggaa ggaagtccct tcctccatac atctgaatac aattctgcct ccacgcatca 10920
ctgtagtcca aaggtaaaaa ataaataata aatgaaggag cattggtcag acagcattca 10980
ttcactgaac tgatacttat tgagtgctta ctctatgcca ggcattgttc taggtgtcag 11040
gaatatagca gtgaacaaag cagatgaaaa tccctgtttt catgaaattt atattctagt 11100
gggaagagat agacaataaa caaatctaca gtatgtcagg tgtgtcttaa gttgtgacag 11160
ggctgtatgt gctgacagtt ttatgaaggg tcattcccca gcccagcccc cagcgcaggg 11220
ctgttttaag actgataatt agttcatgga gcagaagtgt taacctcaat atcttcaagc 11280
atcatcagtt gggtaaaagt cagtcaataa ataaatacag ccactgtgtc ttgagtatgt 11340
aaactgtgca gagcactgtg ttccttactg attaaaaccg ctacattcaa ggtacttctg 11400
tgtgtatggc ccttctttgg cttctgggta tttaaaaaga gctcttggga ctcttctgag 11460
gtcttcctgg gagcagaaca gtacacatgg tctggaattg ggttgcatgg aataactttc 11520
aaggaaagcc actgaataaa gtgccctgca ttcctgtcca ttggatactg ataatgctat 11580
aagatgatct ttctcttctt tattttgttt gagattattg tgactctctg gctaactcct 11640
acttatcctc aggccttttc tgaactcaca attcaaatta cagctccctt tggttctctt 11700
ccacagcagt tgtacttaca tatgtctatt tatataatta tgaatttgtt tcatatttgt 11760
cgccctttac atggtaaact taatgaattt tggggctcca tctgttttgc tcaccacttg 11820
atccttggca tgtagcacac aatggctgct caatacctat ttactgaatg agcaaatgga 11880
ctggaccact tttagagact ggagtatttc cttataccat gtgagattga tttttgagga 11940
cagtttacca ctggaagctt ttgcagaact aaggtcattt ttacagtata cataacctct 12000

-continued

```
gctgtgtttg ttgatactgt aagtttacat tttcttatga ctctttttaa gtagagcacc  12060

cctgtgttta ggaaagctag agctattgtg atgcctttga gtttgcttgg ctgattgctg  12120

ggacttgaac tactgagctt atctaaaagc ctcagaggcc ttgtagcctc tgtcttttag  12180

agagtgtagg taaaggcttg ttttccctca aatcgcttat ctctgatcat aagaaccatg  12240

gctctaatgt ttgtctatag aaaatagaat gttttggccg ggcgcagtgg ctcatgcctg  12300

taatcccagc accctgggag gccgaggcgg gcagatcacc tgaggtcagg agttcaagac  12360

cagcctggcc atggtgaaac cccgtctcta ctaaaaatac aaaaacgttt agccgggcat  12420

ggtggtgtgc acctgtaatc ccagctactt gggaggctga ggcaggagaa tcgcttgaac  12480

ctgggaggca gaggttgcag tgagctgaga ttgcgccact gcactccagc ctgggcaaga  12540

agagtgaaac tctgtctcaa aaaaaaaaaa agaaaatagg atgtttttat tggtttgaag  12600

caacataaga aaaataatga gaatgtagtg atattttcct aagacaaaat taattccatg  12660

tatattccat caataaacat tcactaagtg tctgttatat gccaggcatg ttctaggtct  12720

tggagatata tcagcaaaca aaataggcaa aaattcccat gctgttgtat ttgttttcta  12780

ttactacata acaaatgaac acaaatttag tggcttaaca acaacaccta tttattatct  12840

cttgatttct gtaggtcaga agcctgaggt tggcttagct ggattctctg cccggagtct  12900

cagctagttg aaatcaaggt gtcagctggg actgttatct gtggctcatg gtcctcttct  12960

aagcttattt aggttgttat agatttcatt tacttgcaat tgggttaatt ggatcatggc  13020

tcactgcagc cttgaactcc tggcctcaag tgatcctctc gccatggcct ccaaaagtgc  13080

tgtgagtact gtgcctggcc agaaagagct cttttacatt tatttaaaca cagagtttta  13140

ttttatatta ctctaatgca cacataaaaa agaaaatata agcaaacaaa gttggttaag  13200

gtattctaaa aattatttag gcagtgaaaa cattaagcct gccgggtcta cagcaagtga  13260

ttggaagatg ccaatgtctg taagaaacaa tcttgatttt tttttttttt ttttttgaga  13320

cagtcttact ctgttgccca ggctggagtg cagtggtgtg attacagctc actgcagcct  13380

tgaccttctg ggcttaaggg atcctcccac ctcagtctcc tgagtactgg gactacaggc  13440

atgtaccccc acacctggct aatttttgaa tattttttca ttatagagcc aggttttcgc  13500

catgttgccc aggctggtct caaacaccta agttcaagca atccacctgc cttagccttg  13560

gcctcccaaa gtgctgggat tacaggagag agctgctgcg ccaggccctt gatttttttaa  13620

aagtgcattt tagaatgaat tataataatt gtttaataaa tgttggaatt tgacaaataa  13680

aaaggttatt tagtgcccct caattgtttt gaagtgtcag tgatccatga gctttacagc  13740

agatggaaaa tttgagagca taaatgattt ttccagacac ttccaataaa tataaaatta  13800

acagtggcta atgggggaaa atccttattt tacagtcaga taatgctaat tgacattaag  13860

tagtttcttt tttttttttt tttttttttt tttgacggag tctcactctg tcacccaggc  13920

tggagtgcag tggcacaatc ttggctcact gcacctccac ctcccgggtt caagcaattc  13980

tcctgcctca gcctcctgag tagctgggat tacaggcgcc cgccaccatg cctgnnnnnn  14040

nnnnnnnnnn nnnnnnnnnn nnnnnnnnnn nnnnnnnnnn nnnntaataa tcagggattt  14100

agaaatagga tgaaatgaca agctaaagtc tttgagtctt agttcctcag ctgtaaagtg  14160

ggcatggtac catttcacag gaattgatac gaggattaga agagattagg gctgtgaagt  14220

gcctgacaca cagatagttc ttgaatcaaa tgagggtaaa ttgtagcact catctgtctc  14280

ataagcctaa actgcacatg tatctatata ttcatgacaa aaatcattcc aacacccagg  14340

ggctgtccaa aatacatctc tatctctctg tatacctatt ccctctccac cccccaaatc  14400
```

-continued

```
ctatacaaat tcctcttcct cggccgggca cggtggctca cgcttgtaat cccagaactt  14460
tgggaggcca aggcgggtgg atcacgaggt caggagatcg agaccacagt gaaaccctgt  14520
ctgtactaaa aatacaaaaa attagccggg catggtggcg ggcgcctgta gtcccagcta  14580
ctcggagagg ctgaggcagg agaatggcgt gaacccagga ggcggagctt gcagtgagcc  14640
gagattgcgc cactgcactc cagcccaggt gacagagcga gattccgtct caaaaaaaaa  14700
aaaaaaggta tctctgtcat gatgaatttt tagtcagttt ctttcaccaa aagccagtgt  14760
aaggttgagt gagttggagg ttggtgaaaa ggaagtgaga tgaaataatg tgtctcctct  14820
gtttcattat tctgattctt ccatggtttt gaaattgcca tcccttcatt gctgtggcag  14880
accttttact gactgagctt caatgacaag aaacatcaat tctcctaaaa gtaacacatt  14940
cctgaaaata accgatctct agacattaag gcatatgggg aagcatcttc tcagaaccct  15000
tcctagatct ccagtcttac ttgcatgcgc tttctcctca ccctccagcc tacagacttc  15060
ttcacagcac ttctcaccca atgctgaggg actccccaac tagacttcgc ctccttaaca  15120
gtagaatgga tggcttcttt gctttttatt cctacacagc attccttgct tttgcatgtc  15180
ctcaatagaa gtttgttaat aactgaatgg atcgtctctt aaagaagaga ggaggaaaaa  15240
ttgaaatatg tgaaagaaga tgcatggttt gtgaattaga agcaaccaag ggtagacact  15300
gccaggttac tgatatccac agtaaagttg gttagggtac tttaaagagt aggatagcaa  15360
aagatagata tttggcaaga gattttggca tttaatgggt actacagggg aaaatgttat  15420
caacaattgc ttataagact gattttggcg cttatgtttt gtgttccttc agggtttttt  15480
tgtttgtttg tttttaatga atccactcaa caaacattta agccccttg atgtgctaac  15540
tactgtttag gtacaaaaga atgaagtgta gacaaacaag tgagtagaaa tccttctttt  15600
ctaacaagat cccagctgtt agttggttgg ctaatgaaga aagctggtta gagcagaaaa  15660
tcatctgttt tagtctattc cagcagctat aacaaaatac cataaactag gtggcttata  15720
aacagcagaa atttatttct ggcagttctg gaggctggga agtgcaagat caaggtgcag  15780
gcagattcag tgtctggtga gggttcactt tctggttcat agatggtccg cctcattgtg  15840
acttcacatg gtggaagggg agagggttct ctcttggaca gcaatccatt aatgtgggct  15900
ccaccctcat gacctagtca ccttccaaaa gccctatacc tcctaatacc atcactgtgg  15960
gggttaaaat ttcaacatat acatttgggg aagacaaaga catttggatc ctagcaatta  16020
tacagacata ttttaacata agaagacata atcatccttt gagtggaaat ggccaggaaa  16080
aaaaaaaaga aaaaaaattt aaggaaatga caagcatttg ttaaaggata atttcttttc  16140
tttaatacgg agcaagtgtt tgtggataat ctgtccacaa tccttttaga agtttctag  16200
ttatatttca ttcatttcat tcaacattta ggtcaatggt tatttattta tttattttta  16260
aactcactga gtcctccaaa atattcagca tagcttttgg aggaataatc acatctttca  16320
ttttctattc atatttcatc agtttatgta ataaagacaa gaataactca ctacagttca  16380
agaaaattca gaattatagt tggtagatta tgagtccact gactatagtt ctgaattttc  16440
tttcttatgt aagttatgtg tcttatttag aatttctagt ctcttttctt taatgtggag  16500
caaggatttg tggatagtct gtacataatc cttttagaag ttttccagtt atatttcatt  16560
catcccatca acatttaggt caatagctat tttttttaaa aactactcac ttttactgag  16620
tcctccaaaa tattcagcat agcttttgga aaataatcac ctttcatttt ctattcatat  16680
ttcatcagtt tatgttacaa agacaagaat aaatggcgta aacatatttg ggaaaaaaca  16740
```

-continued

```
aaatgatctt ggtaagattc agttcaattg gtaagagcag aggtacttgg acatactaga  16800

gagcctagta gtatttagtg gtaacgttga tggggcaata gcaatggaga gtgtcctgta  16860

atctagtgag tggtttaggc agaggtcagt tataagagtt tctattgtat tcaacaacat  16920

agataaataa gtgccatata aatatggctt tatgcccaaa ttcaagaagg ggctattaat  16980

tcttcctggg gtgttatgaa agagtcacag ctgctatttt tacagcagat ttctaacctc  17040

tcaaaggaat gtattaataa aaatagccaa catttcttaa actctcatta tgtacaggca  17100

ttattctaag catctgacat ggattaactc atttaatctt tccaacaatc caaagaagaa  17160

atttctataa tatttccatt ttacagatga ggtaatgagg cacggagaag ttaaagtgac  17220

ttgcccagag tcacagagct aagaaatata aatggtatag tggaattaga acccagtcca  17280

tcttgattcc acagccagaa catggctgat aaatatctga aatccttcca gcaccaaatg  17340

attccttttc ttacagagaa tggcaggctg tttattgtaa tggaatattg tgatggaggg  17400

gatctcatga aaaggatcaa tagacaacgg ggtgtgttat ttagtgaaga tcaggtaaaa  17460

acttctaatt tgctttttaa ttttatgtat gtgtggtggg gggagaatta aatttataat  17520

gtcataagta gtagactatg ttgatataaa gcatgtgttt tggtagacag attgaaacca  17580

taaaatagtg gatcaatatt cttggtagat tcagtccaga acaagtttgc aattgaactt  17640

aaactgaatt gttttttaga gagtgagatt ttcttgagaa aagataatct gtttggaaaa  17700

tctcatgtag gatgcctctg agataagtct tcatggttaa aaaaaaatct gaatgtgagt  17760

gttccttagc catttaacat gtaacatatt tatagcttca ctgttttctc ttttaccatt  17820

tggtgctctg ttttaaacta gatatcccac tttgctaggg aggatagaag cttgtcttgg  17880

caatgcctat ttagtttcat tggttattaa gaggggggaga taaaagatga agaataatgg  17940

cctctcccac tttctctttg cacaaatgta tttctcttct atactccaag cctccctgga  18000

actctcttgg gagtggtact catgaaggag acaggtttgt atgtgtggag aggaatctga  18060

attagctcct ttatgattga tggtaaggcc attgcctcaa gaagcacaca ggaaaggccc  18120

accatctttc ctttggccat tgtttctttg ttctatttta gcatgtaaga gcatcatgcc  18180

catataattt cctcttaaag ttgaatattt tgaatatatg aaggattaaa aaatcaatat  18240

ctctaacttc tgtaagatta atcaagcatt ctttgtatgc tcatttatat tatatattaa  18300

attccatatt gatagaaact ctttttctt atctaggtat tattttgcca cattttataa  18360

aaatgcttct catgacaaaa ttttgagtta catttctttt tgttgggaat gaactaaaat  18420

tacaactgaa tattaatgtc tggaatatag ctttattcct attattttcc tctttctgta  18480

taatttggca gacaaagaac cagtgaaatt ttagaatagt ttaaataaat ctctgtaggc  18540

atagaacaca ttttcataaa gaggctcatg gtcaacaaag ataaaatcaa atcatgactt  18600

agaaataaaa ctaaacttca aaggtaaagt atttgttggt tttatattag atatactgat  18660

attttattac aattcctaac ctcacagatc ccccatttct tcctctttct ctccccaccc  18720

ttgtcaccct ccttccactg taaaggaaga accaatggct cccaggttat caggaaacag  18780

ggctgcttgt gtactattca cgatgcagtt agcaccccag ggttaagtag gaaaaaaaga  18840

aaaacatgaa cggcatgcct ctttcccttg cttctactta tctttttctg catgtggaat  18900

ttcccttgat tttaccagtg atatttggat tacttttctg tgcctccatt tttttagttg  18960

tagaatgaaa ataataatat gataaagtgt acctattaac ttcattccta taaatacaca  19020

tacactatat gtgtgtatgt gtgtgtgtgt gtgtgtataa tttctatctt tttgcatgtt  19080

accatgaaga catttcagtg actaccaggc tattcagtgg ctttgttttg tgttctctct  19140
```

-continued

```
atagatcctc ggttggtttg tacagatttc tctaggacta aaacatattc atgacaggaa  19200
gatattacac agggacataa aagctcaggt aacagctcag agagaagact aagacagaac  19260
tgatcttttc ttgaagtacc tcaaacaaca tgacattttc tccatttata gaacattttt  19320
cttagcaaga acggaatggt ggcaaagctt ggggactttg gtatagcaag agtcctgaat  19380
aagtaagtac tttgaaaata atttttcttt ctagtcaaaa tagcccaaat atgtattttt  19440
agatatcatg gattaagaag atattaaaat cttggttgtc taaataattt taggtagctt  19500
tatgtaaatg cattacatca gatggtactt tgagattaaa attctcaaga taaattgtgg  19560
tgtaatagaa tgatgttgct aatattctgt agtgtgattc cagtttgtca aatatggatg  19620
tgactgtaat atgcataaag ctagagagaa tttcgtgaaa taggcaggtt tacacttctt  19680
aatgaaaaaa gtcaaactct ataaaatatt tgaagagatt tattctgagc caaatacgag  19740
tgaccaaagg tccatgcctg tgacatagcc ctcaggagat cctaagaaca tgtacccaag  19800
gtggccggtc tacaacctgg ttttgtacat tttagggaga tgcaagacat caattagatg  19860
tacatgggtt tggtccagaa aagcaggaca actcaaagct gggaagaatg ggagggagct  19920
tccaggtcat aggtggatta aaaacttttc tgattggcaa ttgattgaaa gagtctatct  19980
gaagacctgg aattagtgga agggagtgtc tgggttaaga taaggggttg tggaaatgaa  20040
ggtttttatt atgcagatga aatctccaag tagcaggcct cagagagaat agattgtaaa  20100
tatttcctct tatcggattt aaaaaggtgc cagactctta gttaactttt tcctggatca  20160
ggaaaaagcc ttggaaaaag aagggaattt tcttcagaat gtagattttc cccacaagag  20220
atacctttgc aggactattt caagatatgg acaaagaaac atgatttggg gtaaaatatt  20280
ttgattcctt tcaggcctgc tatctgtcat gtgatgttat actagagtca ggctggactt  20340
tggtatctta ttgctacaag gagtctgctt tgtcagtctt aaggtctgtt ttaatgttaa  20400
tgctggtcaa ctgtgcctga attccaaagg ggaggaggag ttaatgaggc atatcagacc  20460
ctgcttccca tcatggcctg aactagtttt tcaggttaac tttggaatgt ccttggccaa  20520
agggagggtt tatgagttgg ttggggggct tagaatttta tttttggttt acacactttc  20580
tagcaaaata aatttgtgca cctgtttgga agacaatttg gtggcaatat gtaccaagag  20640
atttttaaat atcctgtttc tgggacttct tccaagggaa taatttgaaa tttggaataa  20700
cgtaaatgcc taaataattg ggaaatggtt aaatttaata aagcttggca tggccatggc  20760
catgtacctg aatatatcat aaacatttat ggttttgaag acttcttgat aactttgtta  20820
tactaagcaa agaaaatgga attctgaatt ttaaatacat tgtgatcacg gttatatgaa  20880
aaatatgtgt ggaaagaaga caggaaggaa atatatcaga attttaacaa tagttgtttt  20940
aggtgctaag attctgggta actttttct ccccttattca tttttgtatt ttccaagttt  21000
taaatcatga ggttgcaatt tgataatctc tacatctgag agatttttat aacatgacaa  21060
tttcatctct ttgtggagtc tttaagccat aaaaaatata ttttaatgtg taaatttttg  21120
ggaggtgaat tgtaagttta aaaatcagct gatttagtta ctttatcaac atacagtgtt  21180
ttgctttctt ctaacacatg tatgcatcaa atcttgtgtt atccattttc acattttttc  21240
ttgcatgtcc atgtcttaag acttttctta ctccaataaa aaatcatgct gatttattat  21300
ttaatataat ttactagttc catggaactt gctcgaactt gtattggaac accttactac  21360
ctgtccccag agatctgtca gaataaaccc tacaacaata aaacgtaagt tgctgactct  21420
tagtttgaaa gtgtcagtaa aatctgatgg atgacactga atgaagattc cagaaactaa  21480
```

-continued aattcaaatc tcttctttct ttcttatggt acttttgtaa tttcatttgc ttcatgtgtg 21540
aaattgttct ggaccaaact gagggttggg ttgctatttc tcgcggtcca atacgagatg 21600
cagatgaact ggggaggaag agagttttta tttctgtaac cagtacaggg agaaggcctg 21660
gaaattatca ccagaccgac tcaaaattac aaagtttttc agagcttata caccttctaa 21720
gctatatgtc tatgtgtaag tgtgcattca tttaaagaca tactgattaa ctccttttaa 21780
tctataacta aggtctgagt cctgaagact ttcttctgga gcctcagtaa gcttacttaa 21840
tctaaatggg tctaggtcct ggggtgatta cccttatttt gtctcctgct aaatcatgga 21900
ggtttaggga gttcctgcag acctccaata aacttgtttg tggaggcctg gggagtttct 21960
tcagaccacc aataaaactt gtttaatctt aaaaggctcc ttgttaagaa ttccttcatt 22020
attttgtcat ggtttaaggc ccaggaaagg cctaggcaaa actcttggtg ggcttttgtt 22080
acattacagc ctttgtataa gggcactggc tttttttttt ttattttttg agatagagtc 22140
ttgctcttgt cacccaggct agagtgcaat ggcacgatct cggctcactg caacctccac 22200
ctcccaggtt caagcgattc tcctgcctca gcctcctgag tatctgggat tacaggtggc 22260
tgccaccatg cccagctaaa gttttgtgtt tttagtagag atggagtttc accatgttgt 22320
ccaggctggt ctcaaactcc tgacctcacg atctgcctgc ctcagcctcc caaagtgttg 22380
agattacagg tgtgagccac tgtgcctggc tgggcactgg ctttttaagc ttttaatatt 22440
taacttcacc actcagttag tatagaaaca gttgtgatgg aggcctgcat tggtaagacc 22500
tggcctgcca caaaatgggg atcccagtga ctatctctga gcagtgttac ctgaaggttt 22560
caaacttgtt tagaagaaag ccatttctct tcatttaaag atacaagtgg tataaaaaat 22620
aacatcgaaa attgcagtca ctgtgatgtc catttttgta ttatatgttc atatctttga 22680
agcactgttt agtctattgc aagaaagatt gaagaggatg aagtagaaga caatgtggtc 22740
tggtgaccgc tcactggatt aggagctagg aatcctagtc ttggctcagt tgctaacttg 22800
accaagtcag ttgacctctg tgggcttcag ttccctaact cataataatg agagtattga 22860
ctaggtaatc ttcaaggtgt cttccagctt taaaacccag ttagttttta tgtatgtgat 22920
atcagagtct ggttctcagc aataattttt tttttttttg agatggagtc tggctctgtc 22980
atccaggctg gagtgcagtg gtgtgatctc ggctcactgc aatctctgcc tcccaggttc 23040
aagcaattct cgtgcctcag tctcccaagt acctgggact gcaagcacgc cccaccatgc 23100
ccagctaata ttttgtattt ttagtagaga tggggtttca ccatgttggt cgggctggtc 23160
ttgaattctt gacctcaggt gatctgcccg cctcagcctc tcaaagtgct gggattgcag 23220
gtgtgagcca ccgcacctgg ccctcagcag taatgctaat gtatactgca agaaaaggtg 23280
aagaggagct tttgcttcct ataaggagaa ggaaaaaaat ttcatttttc aaagctggct 23340
gccattgaac aagttggcga taaggaagat tgagttccct ttggaagtta attgtccttt 23400
tgtttaggaa aaaatgccca agagatactt ggctattgga ctttgaagga gataaatgga 23460
aggcaaagct cagacaatag agatttacaa aaagaatagt aagaatttct ctgcataata 23520
aaataacagg gatttttttt ttttttgaga catcccctgg caccaaggag tttggcctca 23580
agttagttgt gcaggaattc aggtagggtg tgttggacgg aaagtaggct gttcagagca 23640
gggcatgcca cagacagcct tgggtcagct gcattgtttt gtttgcttgt actgcttttc 23700
aagaatttga atcaacattt aaatgctgct ggatatggtg gctcatgcct ataatcccag 23760
cactttggga ggctgagggg gatgattgct tgagtccagg ggttcaagac caacctggac 23820
aacattgtga gaccctgtca ctacatccaa aaaaaaatta aatattgaaa gactttaaaa 23880

-continued

```
tatgcatagt ttgtacctct gaaaattgga agatcttagc aataatcagg tgggtagccg  23940
ctggctccat tagaggactg gttcaccaca gtcctcaata tgcagagtgg tctcaggcct  24000
gcaactggcc ccacccaacc cccaggtggc tgcagtactg cctgagccct gggggcatat  24060
gaattctctg ccctggctgc agagggtcct ctgggaacag aagagaagtt tgggtctgtg  24120
gaagccctag taaagacaaa agtctgtgtg gtgtgaaatg gtcagtgagt ttctagaagg  24180
tctagaaagt tcatgtttgt ttcctgggtc aggtgcaggc ggctcacacc tgtaatccca  24240
gcactttggg aggccaagaa gggagtattg cttgagctca agagtttgag accagcctga  24300
gcaacatggt gaaaccttgt taatgaaaaa aaaaattatt aaaaaaaatc ccacaaattt  24360
gtttcccacc aatcttaccg tctattgtac ttactaccat cttttgtact caaactttta  24420
gtatgagtct atctctctct ccttctctct gacacacaca cacacacaca cacacacaca  24480
cacacactca tgcacaaagc attgctgcta gaggagccat ttacctcact cctcacttta  24540
atgattcctt cttgctttga ctccttgact tctgattaga catttttttga tcttttagat  24600
ttaattgtgc tttttgttct ataaaataac tcctcaaacc aatcacatat aaatatttat  24660
gaagtactaa atctgtaagg agcaaagctc atgatatata ttttaagtat atttttaaat  24720
gtttattgag aatcagatac tatgtttatc acataatata actttggttc tgtcaaaagc  24780
cttgagtagg atatatcttt caaaatcaac caaatattac cttttgagtc aaaacaaatc  24840
catgtttgag ttctgcctgc ctcctccaaa ttgctcaaca tttcatcata catacattgt  24900
ttttgagcag gaagctgaac taaatattaa gccaccaggt tgtagcaaag tttgtgtgcc  24960
tttctttgac tagaaatctg acaaactaca aatggttttc attttacctc ttatcttcta  25020
ataagaattg atgatatatc tgaaagcatt tgtaaaagct gatcaactta cataaaattg  25080
taaagcgaca caaatttaag gcactgtaag gataaaagct tttattaaga attatggata  25140
ttttcttggc atgtaaactc ttatcttctt tagggatatt tggtctcttg gctgtgtctt  25200
atatgagctc tgcacactta aacatcctgt aagtatgctc attgtcagac taatcttgaa  25260
ttattggaat tgtagaaaag aaattaactt ctgggagaaa aaggttaatg tttggtttta  25320
ttagattgtt aaaaattata tggataagct acttaaaata atgatagatg acatggaaag  25380
ctgtccaagc aatattataa agtaaaaagt ccaagttgga gaatagtatg tgtagcatat  25440
ttccattaaa aataaattgt gtgggcttgg cgtggtggct catgcctgta atcccagcac  25500
tttgggaggc tgaggcgggt ggatcacttg aggtcaggag ttggagacca acctggccaa  25560
catgatggtg acaccccgtc tctactaaaa atacaaaaat tagccaggca tggtggcatg  25620
tgcctgcagt cccagctagt tgggaggctg aggcacgaga attgctagaa cccaggaggc  25680
agaggctgca gtcagctgag attgcgccac tgcactccag cctgggtgac agcgagactc  25740
catctaaaaa aaataattaa ttaattaatt actgtatgaa tagatacgtt cagcaaaaga  25800
aaaatgtaca tgggcaaagt tcataggaaa ccaggcacaa gcttttaaga gtcttttccc  25860
agaggtcaca tgggatgtgc caaatcctcc agcattgtta cccacgtcac ctgtgaaatg  25920
tgatctataa gaaagctcat cggatatacc cagtgcccag gatttttact ggggactggt  25980
cacataggca ccctctacct ggcatatgcc aaacttccag actcctggaa agaaagcccg  26040
tgttcagcat aaaccatttt gttcacataa atagctgagg caaagatagc cactcttgac  26100
attcagggaa tggtgggaat tcttctgaaa tcttagttcc cagacaccag ccacgggcca  26160
acattgtaag caggcctttc tgaggagagc ttgctacatc aactcttttc tccacagctg  26220
```

-continued

```
tcatcattgt tattaattat tgtcaagggt tgcacagcca gtgtctgacc aaaatgtgta  26280
ctccattgtt tttttgagat ggagtcccgc tctgttgccc agactggagt gcggtggcac  26340
gatctcagct cactgcaacc tctgactcct gggtacaagc aattctcttg cctcagcctc  26400
ccgaggagct gggattacag gcacccacca ccacacccgg ctaatttttt tgtattttta  26460
gtagagtcag ggttttgcca tgttggccag gttggtcttg aactcctgac cttgggtgat  26520
ctgcccacct tggcctccca gagtgctggg attacaggcg tgagccacca tgcccggcca  26580
atgtgtacct ttattgctac accatggagt tgaatattat tatgtataaa taactattgg  26640
tttcatacaa tagaagattt ctggtctatg aagcatttta gaggaaatta aacgatgttt  26700
atgttaattt taaaaagcaa gagataaaat ttcatatcaa tatgacctca actttgtaaa  26760
ataaacatca tttttaaaag agatcagaag gagctatacc tctgagtggt aaaattatac  26820
atattttccc ctgtctttat aacttcctat accttccagt ttttttatta tgagtaaaca  26880
ttattttgat aataagacag aattaaaaca aaataaaaac ttgttttaaa taacatggca  26940
tcttgttgaa taactgcagt atctgctcat gaaagattag ttgatgaaaa caatttaagg  27000
tggaccacag tgcttctttt ttattttttg attgagacag ggtctcactc tgtcacccag  27060
gctggagtgc agtgacgcaa tcacggctta ctgcagcttt gaccgcctgg gcttagacaa  27120
tcctcttgcc tcagcctccc aagtagctgg gaccacaggc tcatgccacc aagcccagca  27180
aatgtttaaa aaccatgatt tggagagatg aggtctaact atgtttccca ggctggtctt  27240
gaactcctgg gctcaagtga tcctcctgcc ttggcctccc aaattgctgg gattacaggt  27300
gaccctagtg cttctaacta caatttaaaa acattgtttt gcttcttggt atatttgtta  27360
ctttaacact tttattattt gttactttag taacttttct ctgatttagt gtcatttctc  27420
cttgtccttt cagtttgagg gtaacaactt acagcagctg gttctgaaga tttgtcaagc  27480
acattttgcc ccaatatctc cggggttttc tcgtgagctc cattccttga tatctcagct  27540
ctttcaagta tctcctcgag accgaccatc cataaattcc attttgaaaa ggcccttttt  27600
agagaatctt attcccaaat atttgactcc tgaggtaagt tttgaggtga ctgtttggat  27660
tttggcagag attttgggtt gcaggtcctt gacacgtgtg ttcggtttta ggtcattcag  27720
gaagaattca gtcacatgct tatatgcaga gcaggagcgc cagcttctcg acatgctggg  27780
aaggtggtcc agagtaagtg tgactttggc atgcaatcaa aagtatttat tacacatgtc  27840
tcacacagag agtaatgcaa ggaaatttca ccaaacatat tgaaagtgga cattttaaaa  27900
aatacaagca gtataagcag gagaaaaatc atcttgtcaa atggcaacta gtgagtgtgc  27960
ctgaaagttg tatatctagc tcatgcatga cctgcagggt tccttctcgt tagtcaggaa  28020
acctccatga agcagaggac atgctaatag agatgcttga agaggttgag cccaaactta  28080
acttttgtgt agtgaaggga cagagtggga gaaggttgca gatagacatg gatgatgaga  28140
tgaaacttat ttttctaaaa gaggatagac tggcaattaa gaattctgtt gcaaaggacc  28200
attggagctg aagttaggat cttggggcct aattgataac agtaagaact gttactttgt  28260
ggttcccaaa gaaggcagga gatattttat ggtagtaata aatacagaaa actttttttt  28320
ttttccgaga cggagtctcg ctctgtcgcc caggctggag tgcaatggcg cgatctctgc  28380
tcactgcaaa ctccacctcc cgggttcatg ccattctcct gcctcagcct cccgagtagc  28440
tgggactaca gccgcccatc accactcccg gctaattttt tgtatttttt tagtagagac  28500
gaggtttcac tgtgttagct aggatggtct cgatctccgg acctcgtgat ccgcccgcct  28560
ctgcctccca aagtgctggg attacaggcg tgagccaccg cgccaggccg gagaaaacta  28620
```

-continued ttttagtcct ggtgtcaaga atcagctaag ctgtgtgtca gagggagggg tacgttaaga 28680
aagagaaaat tactaattca tttgatgctg tgaaagtcaa agccccagaa tttagctgta 28740
actgaatgcc tggacttaca atatcaggag gagcagaaag cctctcaaag gaatccatga 28800
cagggaaatg ttatccattg agacagagat tctaaaatca aggaaagtta aagagaaagt 28860
gaatgagcct ctttgccatt taatttgact aacattgttg tataccagtc tagattgaga 28920
atgtttagaa aatagacaag tacagagtat gggactgtgt attgtccata tttctaatct 28980
aggtaagata ggagaacaag aacaattttt tttttattga gatggggtct cactgtgttg 29040
cccaggctgg tctcgaactc ctgagctcaa acaatcctcc taccttggcc tcccaaattg 29100
ctgggattac aggtgcgagc caccttactc agcccaagaa caaattttga tggagataaa 29160
gacaagcatt agaagatcta ctcatacctc agtcctggca ctttgggagg ccaaggaggg 29220
caggtcaccg gaggccagga gtttgatgcc agtctggcca acatggccaa accatgtctt 29280
tactaaaaat acaaaaatta gctggacctg gtggcccatg cctgtaatcc cagctccttg 29340
ggtggctgag gcacaagaat cgcatgaact cgggaggtga aggttgcagt gagctcagac 29400
cctgccactg caccgtagcc cgggtgacag agtgagactg tctcaacaaa aaaaaaagag 29460
agaagatcta ctcataaatt ccaaacaatg tggcatgaat ggagtggcct gataacccaa 29520
gctctaatga ccaaatttaa taacttttat tattacccca tacatattgt ttctgtaaat 29580
gttaatatta atttctattt ttctgaaaaa aagtgatgtt atatattact agaaatatgc 29640
aaagggactc tgaaaaaatg gtttttttca tttaaagaaa ttgcatatta atttttcatc 29700
agtactctca ctgtgtgtaa aatatctctg gctaaaaagt aaacttactg tgttatgaaa 29760
tgtagcttat gtttatactc ttacaagtat cagtattaat ggtgtacaat ttttaaaaaa 29820
ttgaagctgt tttattttgg ttaattaaga gtgtaaaata caaaaagtga gattccaggg 29880
aaagtgccca ccaagatcaa ggatatctgt gccaattaaa aggaatgcta tattgcatag 29940
aaatgaatgg agaccaccag ctggagccca gaaggccaga tctgtaagtc attctaaacc 30000
ctcctttgtg ttttttagct atggtatatg ctttttgttt gtttgtttgt ttgttttgag 30060
acggagtctc gctctgtcgc caggctggag tgcagtggcg cgatctcggc tcaccgcaaa 30120
ctccacctcc cgggttcaag caattcttct gccccagcct cctgagtagc tgggactaca 30180
gacgtgtgcc actatgccca gctaattttt gtatttttgg tagagatggg gtttcaccat 30240
attggccaga atggtctcca tctcttgacc tcgtgatcca cctgcctggg cctcccaaag 30300
tgctgggatt acaggtgtga gccatggcgc ccggccccgg ctaattttta tacttttagt 30360
agagacaggg tttcaccatg ttggtcagac tggtctcgaa ctcctgacct tgcgatcagc 30420
ctgcctcggc ctcccaaagt gctggtatta caagcataag ccactgcacc cagctgttat 30480
attctttttc tttaattttt taattaaaaa aaaaattttt gtgggtacat agtaagtgta 30540
tatatttatg gggtatatga gatgttttga tacaggcaag caatgtgaaa taagcacatc 30600
atggagaata gggtgtttgt cccctcaagt atttatcctt tgagttacaa acaacccagt 30660
tatactctgt aacttatttc aaaatgtaca attaagttac tattgaccat aggcagtcta 30720
ttgtgctatc aaatagtagg tcttattcat tcttttgttt ttttaaccca ttaagctatg 30780
gtatattctg acagacctat ctgcacatgt tcatgaggta caagcttatt gtttggagtc 30840
cacaaatttt gtacttaaaa tgaagtattc tgtactgagc attataatgg tattttgttg 30900
gacaacttct agtttttata ttttatgaaa caatgctgta tgctcttata agtatacttt 30960

-continued

```
aggcttaatt ttctttttat aactgaaatt cttctaattt ctaataaata agatttttct  31020

gtataggaaa agtgagtaac atagcaacag aaaacactct gcatttaata ttcttaattc  31080

taacatatta tgtataggat tgagaagttt ttatgatata ataattgata tttccctagt  31140

gattctttgt gtttaattat ttgaattcac ttcagcagag tgttgaatct tttaggtcat  31200

actagtgaaa tgcttctggt atgtaaatga taaaatggct actgtctttt aattaaagaa  31260

ttgtattttt aaagaaggct catggttaaa ttaagaacca tttggaagtg tatttactaa  31320

gtgtttactt gatatataga cattttagaa aatgtgttgg tatataaaca tttttttaaa  31380

aaccgattgt ttaagttatt gcccttcatt tgataaaggg ctttatttat ttatttattt  31440

atttatttat ttatttattt atttatttga aagagggtcc tgctgtgtca cccaggctag  31500

agggcagtgg catgtctcag ctcactgcag cctggatgta ttagtctgtt ctcatactac  31560

tataaagaac tgcttgagac tgggtagttg ataaagacaa gaggtttaat tggcttacag  31620

ttctgcaggc tgtacaggat gcattgctgg ggaggccgca ggaaacttat aatcatggca  31680

gaaggggaag caggctcatc ttaaatggcc agagcaggag aaagagagca aagggggagg  31740

tgctacacac ttgtaaacaa ccagatctct ggagaactta ctatcacaag aacagtaaga  31800

gggaaatctg tccccataat ctaatcacct tccaccaggc ccctcctcca acatcaggga  31860

ttacaattca acatgaaatt tgggcaggga cacaaatcca aaccatatca ttccaccttt  31920

ggcccctccc aattcccata tccttctcac attgcaaaat acaattatcc cttctcaaca  31980

gtcccccaag gcttaactca tttcagcatt aactcaaaag tccacaattc aaggtctctc  32040

tgagacaagt caagtccctt ccacctgtga ggctgtaaaa taaaaaacaa gttagttact  32100

tccaaaatac aatgagggta caggcattgg gtaaatacac ccatttcaaa agggagaaat  32160

cagccaaaac aaagggttta tagaccccat gcaaattcaa aacctagcag ggcagtcatt  32220

aaatcttaaa gctccaaatt cctttgaccc catgtctcac atccagggca tactggtgtg  32280

aggagtgggc tctcaaggcc ttgggcagct ctgctcctga ggctttgcag gctacagccc  32340

ctgcggctgc tctcacaggc tgctgttgag tgtctgcggc ttttccaggt gcgtggtgca  32400

agctgtcgtt caatctaccg tttttggagt caggagaatg gtggccctct tctcacagct  32460

ccactaagca gtgccccagt ggggactctg tgtggaggct ccaatgccac atttcccctc  32520

tgcactgccc tagtagaggg tccccctgaa acaggcttct gcctggacga ctaggctttt  32580

ccatacatct tctgagatct tggtggaggc tcccacgcct caactcttgc actctgtgca  32640

tctgcagact taacaccatg tggaagccac caagatttac ggcttgcacc ctctgaagca  32700

atggcctgag ctgtaccttg ggccgtttta accatggctg gagctggagc agccacaata  32760

caggacacca tgtcctgagg ctgcacagag cagtggggcc ctgggcttgg tcctcaaagc  32820

cattcttccc tcctaggcct ctgggcctgt gatgagaggg gctgcctcaa aggtctctga  32880

aatgccttca aggcatttcc cccattatct tggctaacaa catttgactc ctctttattt  32940

ttgaaaattt ctgcagctgg tttgaattgc tccccagaaa atgggttttt ctttctaggc  33000

tgcaaacttt cctaactttt acactctgct tctcttttaa gtataagctc tggttttaca  33060

tcatttattt gctcacaaat atgaccatag ggtgctagag cagccaggcc acatcttgaa  33120

tactttgttg cttagaaatt ttttctgtca gacgccttaa atcatcactc tcaaagttca  33180

aagttccaca gatcccctag ggtagtggca caatgcctcc aacctctttg ctaattcata  33240

acaaaagtgt cctttgctgc atttctcaat aagttcctca tctccatctg agacctcctt  33300

agcctggact ttattgacca tatcactatc agcattttgg tcactatgat tttaagaagt  33360
```

-continued

```
ctctagggca ttccaaactt tccatcatct tcctatcttc ttctgagccc tccacgctct  33420
tccaacctcc gcccattacc cagttccaaa gtcactttca cattttcagg tatctttata  33480
caatacccca ctcctggtat caatgtactg tgttagtcca ttctcatact gctataaaga  33540
acacctgaga ctgggtaatt tataaagaaa atacatttaa ttggctcaca gttctgcagg  33600
ctgtacagga agtatggctg gggaggcctc aggaaattta taatcatagc agaaggggag  33660
gcaggctcat cttacatgca ggaggaaaag agtgaagggg tagccgctac aaacttttga  33720
acaaccagat ctcatgaaaa ctcactcact atcacaagaa cagcaagggg ggaatctgcc  33780
ccaacgatcc atttaccagg cctcgtctcc caacattggg gattacagtg caacatgaga  33840
ttgggcagag acacaaatcc aaagcatatc actcgacctc ccaggctgag acacaaatcc  33900
aaagcatatc actcgacctc ccaggctcaa gtgatcctac cgtctcagcc tcctgaatag  33960
ctatactacc ggtatgcacc atgatgccca gctagttttt actttttgta gagtcagggt  34020
ctcactgtgt tgcccaggct gttcttgaat tcctgggctc tagtgatatg cccgcctcag  34080
cctcccaaag tgctgggatt ataggcgtga gccactgtgc ccagcctaag ggcttaattt  34140
tattaaagaa ataagaaaag tatgttgtga ttcagaggac tctttatcag acctgtagaa  34200
gggaaaacac atctaaaaga tttgaggatg aattaaatta cgaactgttg aacacgctga  34260
catttttcca gttccttgaa aaggtaaaat tgatttccac aggaactacc tctgatattc  34320
ctattactgt tgggatgtta gagaacattt taaagaaaat gtttattgcc tttcaatact  34380
tttctatatt ttttaccact tttcaacaag tcattagtag cattttcttc taggttgtat  34440
ataggtgaaa ttgtaaaaca aagaaaacta cttcttgttt taaaagattt taaaaatagg  34500
caggtgcagt ggctcacgcc tataatccaa cactttggga ggctgaggca ggaggatcat  34560
ttcagcccag gagttcgaga ccagcctggt caacacattg agaccccacc tctacaaaaa  34620
gtaaaattaa aaaaaaaatt ttttgttttt tactggacac agtagcatgt gcctgtagtc  34680
ccagttactt gggaggatga ggcaggagat ccctggatcc caggagtttg aagctgcgat  34740
gagctatgat cacaccacag tcctgcaggc tgggtgacag agtgagatcc tgtctcagaa  34800
tttaaaaaga aaagaaaata ttttaaaaat aaacatataa tttgtattta gattaatgaa  34860
ctaaatttta tacatttact taaatattta aatagaacta tatgaaagtg ccatttttct  34920
agattaatta tggtcaattc tgggcaattt cttttttga gacggagtct cactctgtca  34980
cccaggctgg agtgcagtgg tacgatcttg gctcactgca agctccgcct cccgggtttg  35040
tgccattctc ccgagtagct gggactatag gcacccgcca tcacgcccag ctaattttgt  35100
ttttgtgttt ttagtagaga cggggtttca ccttgttagc catggtggtc tcgatctcct  35160
gacctcgtga tccgcctgcc tcagcctccc aaagttctgg gattacaggc atgagccact  35220
gcgcccagcc aattatgtgc aatttcatat ggtccaatct aacatatatg tgaaccatat  35280
agcagtaaaa acaacaaaga atataacatg ttacctcttt acatgaggac attttggttt  35340
taattgttct tgttattcat attcccaact attagttcct aggtctttcc agtagtttta  35400
tctttttttc tctttttatt attaactgta aactgtaaac tagacagagt tgccacgctt  35460
taggttaaat tgaccccact ttgctcttta gcaagaaggt cttgactggc ttttatatct  35520
taatttgatc tgtttcttgt cttctagctc agtggcttct actcagttgg aagataaact  35580
gtcatttctg gttctcctat tctcattctg ttctggttgg gaagggtggt gagggctggg  35640
atggtgatat gcccatcatg gctgttatat gaccttttt aatattttct ctggaagaat  35700
```

-continued

```
gattctgatt cagcatcttc tttcctttaa gtcatgatgc cattttgcat ttagtcaatt  35760
tatcagaaac taaaaatgtt gcaaatcccc atatgtgtga gtttcactat gctttttatt  35820
tccctgtaaa gtatggtaag gtataaatga gtttatgaaa aatagaaaac aataattctg  35880
agtttagttt tggatcttgg gttgcctggg catactcact agctaagtat ttttcacata  35940
ctagccatga agtatgcatg attcatatcc ataccttagc aaaattgtaa accactatac  36000
tatctagtac ttaggtcttt ttgtactcta ggatttgggg actcttaaga ttattctgga  36060
aaaaaaagta tagaagaaaa acagcaaaaa tacaccttca gtgccttatc ttagctatgg  36120
tcactgttat attgtcaagt attataaatt tgtattatgg tttttttttt tgagatggag  36180
tctcgctcac attgtgcagg ttggagtgca gtggcatgat ctcagctcac tgcaacctcc  36240
acctcctggg ttcaagtgat tctccttcct cagcctccca agtagctggg attacaggcg  36300
tgcgccacca tgcctggata atttttgtat ttttagtaca gacgaggttt tgccatgttg  36360
gccaggctgg tcttgaactc ctgacctcag gtgatccacc cgcctcagcc tcccaaagtg  36420
ctagggttac aggtgtgagc cactgcaccc agcctgtatt atggttttta aaaacatccc  36480
ctcttgtttt cttcagataa aaatgataga aagacccaaa attgctgctg tctgtggaca  36540
ttatgattat tattatgctc aacttgatat gctgaggagg agagcccaca aaccaagtta  36600
tcaccctatt cctcaagaaa atactggagt tgaggattac ggtcaggaaa cgaggcatgg  36660
tccatcccca agtcaatggt aatattgtgg tctagcttaa gctttggtta atctaaaaat  36720
atctttatat attaacattt attattctga aatccaaatt ctcctaacac aaataatcca  36780
agaagaactt tccaaatctt cattttaaac acatagttcc cttgaccttt ttcttttgtt  36840
tgcttttgta gacagtctca ctctgatgcc taggctagag tgcggtggcg caatctcagc  36900
tcactgcaac ctctgccttc tgagttcaag cgattctcgt gcctcggcct ctccagtagc  36960
tgggactaca ggcgtgcacc accatgccca actgattttt atatttttag taaagacagg  37020
gtttcaccat gttggccaac ctgatcttga actcctgacc tcaggtgatc tgcccgcctc  37080
agcctcccaa agtgctggga ttacaggcat gagccaccat gcctggccat gttagtccct  37140
tctttctatg tcagccctat acctgcttgt tagttggttc ttcaaattct caggtaccct  37200
ctcaccaggc agccactgac ctcatgtgat ccacctgcct tggcctccta aagtgctggg  37260
actacaggca agagccacta ttcccagcct ttctttcttt ttttttgtt agaaagattt  37320
tgtttttatt tccatcagaa tgtcatatat gttacacaaa tcaaatctgt tgacatctca  37380
agcttataac aattacgtgt tcttataaat tacgtgggaa ttacatgtac tgtgagaagt  37440
gttgtaatta tgatgtaatg tatattataa tttagcctac agaagtaaca aagtcttgta  37500
attaaataaa gcaataaatg tgttgataga ttattacaat tgataagtaa ttgataaatt  37560
atcttctttt tcctgtaacc cttcttcatc tcaagtctga tctagcttat tttcttattc  37620
atagagctgc ttaactgtag gcacagaccc atacccttgc tcttttaata ttctttcttc  37680
ctcctactaa attccactat atggcaggtg aaaaaatagt tgtgtatatt tcatttctca  37740
aagaggttac taatatgaat caataattga atcattaaaa tcaaatgatc atttgagaca  37800
ttttgagaaa taagatatat ttcattcggc atttatgttc tagggatttt caaaatatgg  37860
acatgttaga aagaaaatag tattcttaaa ttggtcttat ggtagatttt caaaaaattt  37920
actccataat agatttctgc agatctacaa tattttcaaa tttttttcac actgatgttg  37980
acattcctgt gttcagaata attgacacct aacagaggcc tgaagactta agtctaagag  38040
ttctatttta aaaatgtttt gtcatcaatt ttttttgttc agggttaaga atttgttact  38100
```

-continued ttggcgactc tgattgttta ttgttgaaat tttggatgaa ttatgaaaaa cacaagatac 38160
tatgggatgg caatctcatt aatagtgaaa atgagataag caagaatgat aagagaataa 38220
tttcttcaga aacatataac gggaaaagca tatgttttat ctttaaagat attgggcact 38280
gttgtggttt ttatcgatct tcataacaca tttttaatta tctccacaat tatcaaaagt 38340
tatgtcttct gtccgttcaa attgtaatat ccatattgga ctcaattagt gagggacata 38400
gattttacag aagaactgga gcagccacaa aactcccttt ctcttttctc aaccactggg 38460
aaaatatatc ttccactctt tgtctagatt tgagagctgt caagctatca attattttga 38520
ccacatgtga ttttatatct cccaagctct cacatgaaac agtaggaagg gtccttctct 38580
ttcctggatg cccctttgat gcctggtaac ccctcctctt tgtatactcc ctcatcccca 38640
gctttctgtc tgctggaggt ccaattacag gccatgggat ggaggaaaag gattttttt 38700
ttttttgaga cagagtctcg ctctgtcgcc caggctggag tgcagtgacg cgatcttggc 38760
tcactgcaag ctccgccccc tgggttcaca ccattctcct gcctcagtct ccagagtagc 38820
tgggactaca ggcgcctgcc acgacacctg gttaattttt ttgtattttt agaagagaca 38880
gggtttcact gtgtcagcca ggagggtctc aatctcctga ccttgtgatc cacccgcctc 38940
ggcctcccaa agtgctggca ttacaggcat gagccaccat gcccggccga ggaagaggaa 39000
tttgtatagg atttgggggg tggagaggga ataggtagac agagagatag agaatgtctt 39060
ttggacagcc cctgggtgtt ggaatcattt ttctcatgaa gatattgata catgtgccag 39120
ttaggcttat gagacagatg agtgctacaa tttaccctca tttgattcaa gaactatctg 39180
tgtgtcaggc acttcacagc cctaatctct tctaatcctc gtatcaattc ctgtgaaatg 39240
gtaccatgcc cactttacag ctgaggaact aagactcaaa gactttagct tgtcatttca 39300
tcctatttct aaatccctga ttattaactt gcctctttgt aaattgggga tgcttatcat 39360
gatgttcctt cctaaaggag ttatttctga aattacagtt ctgtctttgg agccttagaa 39420
gttactcgta ttccaaaaaa cttatggtct gaaatgcggt ttttatttag caaccaataa 39480
ttacagaaat gttttacagg aaattctgcc aaaaaaaaga tacataaaat gtgagtataa 39540
acttgaaaat tgtttgactg gaattgacta aaattgtgct ggaaaaatac cttaaacatt 39600
tggagagaca gctaaaccat tatttctttc ctcattaagc atttatgtgc ggagataaag 39660
ggatggatgg agggacacat tctgctctca gggagctcag tatgtggtgc aggaaacaga 39720
tatgcagcca ttcttttttt tcttttcttt tctttttttc tttttttttt gagatggagt 39780
ctcactctgt cactcaggct ggagtgcagt ggtgcgattt tggcttactg caacctctgc 39840
ctccctgctc agcctcccca gtagctggga ttacaggtgc ccaccaccac gccccactaa 39900
ttttttttag cagagacggg gtttcaccat gttggccagg ctgatctcga actcctgacc 39960
tcgtgatcca cccacctcgg cctcccaaag tgctggggtt acaggtgtga gccaccacat 40020
ctagccacta ttgttaaatc aggagcgaca acctgtacat tagacaccta cacaaagcgt 40080
gagaacttct gggtgtgggt ctgttttcct ccccacaaca tattatagag aatggaagga 40140
ctgaatcttg tcctgaagaa aaatcactgg ataagaatat ttttctgttt aatcctctcc 40200
tgtatcccca cttgttactc ttcatccttt tttccttttg attccaaaat tttcttttcc 40260
aatgtaaaga ttctgtaact gtgaactact tcttgaactt ggaacttcaa gccactggtg 40320
aattgtgaat ctcattacta aactgaaaat tactcgtcaa attggtgcct aagattcgtt 40380
caagtttcta cttaagctga acattcttat tttctaaggc ctgctgagta ccttcagaga 40440

-continued

```
aaatttgaag ctcaacaata taagttgaaa gtggagaagc aattggtaag taaaatacca  40500
aatatgggaa gcaattagga atttcctaat agtttttctg ttcacagatt ttcaagtcaa  40560
agttcattcc accagaaggt caagaatact ctctactagt ccccagtttt ttttgttttt  40620
gtttttgttg ttgttgttgt tgttgttttc tgagacagag tctcgctctg tcaccaggct  40680
ggagtgcagt ggtgtgatct tggctcactg caacctctgc ctcccaggtt caagcaattc  40740
tccttcccca gcctcctgag tagctgggat tacaggcgcc caccaccacg cccagctaac  40800
ttctgtattt ttagtagaga cagggtttca ccatgttgtc caggctggtc tcgaactcct  40860
gatctcgggt gatccaccca cctaggcctc ccaaagtgct ggggttacag acgtgagcca  40920
ctgcacctgg cccgagtccc cagtttttaa tagctaaata aaataatggg aacaggcttg  40980
aatcaccccc ttagcagtcc ggtttcttcc ttggctctat ctcttctgtg ggaccttgga  41040
cagttcattc agcctatctg agccttaatt tccttttcta taaatgacaa tttttagagt  41100
agatgagctt caaatttcct tgcagtgctg tagtgctttg gttctatttt gttaaagatt  41160
ctgctgcaca ttaaaaaaag tgacaagggg ccaggtgcgg tggctcatgc ctgtaatccc  41220
agcactttgg gaggccaagg tgggcggatc ataagatcag gagttcaaga tgagcctgac  41280
caacatggtg aaagcccgtc tctactaaaa atacaaaaat tagccaggca tgatggtgca  41340
cacctgtaat cccagctact tgggaggctg aggcaggaga attacttgaa cccaggagga  41400
ggaggttgca gtgagccgag atcgccctac tgcactctag cctgggcgac agaacgagac  41460
tctgtctcaa aaaaaacaaa aaaaacaaaa accaacaaca aaaaagtgat taggccagat  41520
attatggctc atgcctgtaa tcccagcact ttgggaggct gaggtgggtg gattgcttga  41580
gcccaggagt tcgagactag cctaggcaac ataatgagac cttatctcta ccaaaaaaaa  41640
caaaaattac ccaggtgttg tggtgtgtgc ctgtagtccc agctactgag gggctgagg  41700
ccggaggatt gcttaagctt gggaggcaaa ggttacagtg agctaagatt gcgccactgt  41760
actccagcct gggtgacaga gtgagactct gtcttaaaaa aaaaaaaaaa aagaaaggct  41820
gggcttgatg gctcatgcct gtaatcccag cactttggga ggccaaggcg ggcagatcac  41880
gaggtcagga gattgagacc atcctggcta acacagtgaa accctgtctc tactgaaaat  41940
acaaaaaatt agccgggtgt ggtggcgggt gcctgtagtc ccagctactc ggaaggctga  42000
gacaggacaa ttgcttgagc ctaggagttg gaggctgcag tgagccaaga tcatgccgct  42060
gtactccagc ctgggtgaca gagtgagacg ctctcaaaca gaaaaaaata tatatttttt  42120
aatgctttat aattaagaaa attctactac ttaccacaaa aaaaactccc aaatactgag  42180
tttgcttagt gatataattc ttatttatag gaaaaagtca atgtcaaatc agaagatgtt  42240
tccgaaatca aagtatgcat tataaattat ttcattcaat aaatagggtc ttcgtccatc  42300
ttctgccgag ccaaattaca accagagaca agagctaaga agtaatggag aagagcctag  42360
attccaggag ctgccattta ggaaaaacga aatgaaggaa caggttaaaa actgtttaat  42420
tccagggcta cccttgtatt tctttgtatt actgtctttt gtactgtaat agggagttac  42480
ttctatttcc tacagtgccc ctgaatatgt caacaccatg ctgagtgtta taggggatac  42540
agagttaggt atttcacttt ctcagataat gcgatatggc taagttcata aagcttttca  42600
ccttgagatt catagagtaa ctgtccatca gtaacaggtt tgggatttgt attagtttcc  42660
tgggctgctg taacagagtt caacaaacta ggtggcttaa cacaatagaa atgtattgtc  42720
tcacaattct ggaagagtgg aaatagaaaa tcaaggtgtc agcaggacca agtgccctct  42780
gaaacctgta ggggaatcct tccttgcctc ttcctagctt ctggtgcgtc actggcaatc  42840
```

-continued

```
tttggcattt ctttacttgc agtcgcatca ctccattctc tgccttcatc acatgctgtt  42900
cttcctgtgt gtccctgtct tcacatggcc atcttcttgc aaggacatca gtcatattga  42960
actaagggcc cactggtatg atctcatctt aagtagtctc atctgcagcg accctgtttt  43020
caaatggggt cacattctaa ggcactgggg gttaggactt caacatatct ctttttgggg  43080
aggaacaaac ttcagtgcat aagagggtta tatataaaag tgggatttat aaagtaagtg  43140
tacatcatga acacatttgg gttatatata aaattgagct ctgtagctaa agccactgtc  43200
tcacagggag tgaagtactg cagccaaaac ataaggcaga ttatcatctt taggagcaac  43260
atatttttct aaccttattt tatattacac acttttgaaa ttgtaggctg cagaaagatt  43320
atttttgtta tggtgttcat aaacatttaa agtttctgga ttgggtttgc tttccaggaa  43380
tattggaagc agttagagga aatacgccaa cagtaccaca atgacatgaa agaaattaga  43440
aagaagatgg ggagagaacc agaggtaaat tcattcttct aggggaaaca ttgttctatc  43500
gatttagagc taactaaatt gagctggtat taaaagtaat gatttcctta tagaaaagat  43560
aaagttttat catagagata atcatgtaga cttctttttt aataggaaag ctgtcagacc  43620
tcattggagc ttcagtttat tatggtttat gagagactac acaagataat aaggatatct  43680
gagattctca ggaatggcta ttattaaaag tacttattga ttgtttcctt catgaatcac  43740
tcaatacata tttattgagt ggcaacttta gacaagagct ggattagatg cagaaagtcc  43800
aaaatgagtg taagttcatg cccagaaggt gggaaaaaaa caaacccaac acactagcat  43860
tttttcaact ctctgcaggg taaggttcta aaggctattt aaggcaaaat ctgagtgcag  43920
ttgaactgat tcttaaaaat ctcttaaagg cgccacattg gaaattcatc cttccatctc  43980
ccaagaaggt ctctagagtt ggcacagatc actgcttctt cagaagagct tcacatgaaa  44040
tagccagcct gtgtttggaa accatgttgt aagaaagaca catggctatt gaaacactag  44100
gaacacactc agtgccctgg aatgctctcc taggagaagc ttgcaggcac tgagacagct  44160
gtctcccatc ccacatgcac ttggccacac actcattgag tagagctacc atgctgctga  44220
aattgatctc tctctctctt tctcccaccg cagtgcatac agataaattc atataagtca  44280
aatgaatgta tggtgcaatt cagttgtgtt tgccaggcca tgaactagag ctttcacata  44340
ctgtattagt ctgctctcat actgctaata aagacatacc caagactggg taatttataa  44400
agaaaaagag gtgtaataga cgcacagttt cacatggctg gggaggcctc acaatcatgg  44460
cagaaggcaa aggaggagca aagtcatgcc ttacatgaag gcaggcaaga gagcttgtgt  44520
aggggaactc ctatttacaa aaccatcaga tcttgtgaga cttactcact accattaaaa  44580
tagtatggga gaaaccaccc cgatgattca gttatctcca cctggcccca cccttgacaa  44640
atgaggatta ttacaattca aggtgagatt tgggtgggga tacagagcca aaccatatca  44700
cgttcatact ttcttttatt taccoctgta cagagaagtt aagtagctca tccaaagtca  44760
cgtagctatt acaaggcaga cgaaatattt aaatatctga ctctaggctg ggcacggtag  44820
ctcatgcctg taatcccagc aatttgaaag gctgaggtgg gaggattgct tgagcctagg  44880
agtttgagac cagcctgggc aacataggga aaccctagct ctaaacacac acacacacac  44940
acacacacac acacacacac acacacacac acacacacac tctctctctc tctctctctc  45000
tctctcactc tctctctctc tctctctctc tttaaattag ccggacatgg tggtttgcac  45060
ctgtagtcct agctacttgg gaggctaaag cagaaggatt gcttgagcta ggagctaaag  45120
gctgcagtga gccatgattg tgccactgta ccccagcctg ggatacagag caagactcgg  45180
```

-continued tctcaaaaaa ataaagtaaa ataaaatgaa aatctgactc taaaacccct actcatgttc 45240
atgcctgtaa tcctagcatt ttgggaggcc aaggcagaag gatcgcttga gcccaggagt 45300
ttgagaccgg cctgggcaac ataatgagac tccatatgta caaaaaattt aaaaaattag 45360
tgggtcatgg tggcaaatgc ttgtagtccc agctactcag gaggctgagt tgggaggctg 45420
aggttgaagc tgctgtgaac tgtgattttt ccactgcact ccagcctggg caacagaggg 45480
aggccctgtc ccaaaaaata aaaaaataca attataacca ctattctttc tggcatatgc 45540
agttctactt ataaatggtt ggaatgacga gacacatgta taaaacaatc atagagtaag 45600
ccctgtaggt gcacaggagc caagatgagc agaatgagca ggtagcgggt atttatggaa 45660
gaagtgggtg gggcctaaag agtggaattt ggagaggcag agttaaagga ggagagtggg 45720
cattctgaaa gaaccatgca aaggttggga cagaggactg tgtgtgctgg gaggggcagc 45780
ctggaggttg ttctctctgg agcagaggcc tggctcatgg gcagcctgga gccatcatca 45840
gccttatgtc taaggctgat ctgggatggg cagcctgagc cctgcaaaaa tggatagcag 45900
acattggtca ggcgcggtag ctcacgcctg taatccccag cactttggga ggctgaggtg 45960
ggcggatcac gaggtcggga gatcgagatc atcctggcta acacagtgaa accctgtctc 46020
tactaaaaag ccaaaaaatt agccaggcgt ggtggtgcgt gcctatagtc ccagctactt 46080
gggaggctaa ggcaggagaa tggcatgaac tcaggaggca gagcttgcag tgagccaaga 46140
tcgcaccact gcactccagc ctgggtgaca gagtgagact ccatctcaaa aaaaaaaaaa 46200
tggtggatat cagacatttc tacagaggct atggaggaag gatttgggaa atactgaagc 46260
tgtggcgggg aaaaggagct ataaaaaggg ttctgtccag ccatttcatc attgatcgcg 46320
catcagccaa gtagccttca gagctcactc agaaccaatc ttgttgactg tgtataattt 46380
gtgttaaagg agaactcaaa aataagtcat aaaacctatt tggtgaagaa gagtaacctg 46440
cctgtccatc aagatgcatc tgagggagaa gcacctgtgc aggtaatgat ggctatgatc 46500
agatgtgtgt gcttgcagtg tgtgtgctct accccaagtg gctcttaccc ttctctgtgc 46560
agcagaacca cgtagggaac tttttttttt tttctatgag acggagtctc actctgtcgc 46620
caggttggag tgcagtcgtg cgatcttggc tcactgcagt gtctgcctcc tgggttcaag 46680
tgatttcctg cttcaggctc ccgagtagct gggactacag gcatgcgcca ccatgcccag 46740
ctaatttttg tatttttagt agagacagga tttcaccatg ttggccagga tggtctttat 46800
ctcttgacct cgtgatccac cagcctcggc ctcctaaaat gctgggatta taggcatgag 46860
ccaccgcctt tttaccagaa cttttaaaaa ctcagatgcc tctctctgcc ccagatggtc 46920
tgggatgagg cccaggcatt ctgtctgcag aagcttgctg ggtgatttag taagcagcca 46980
agtttgagaa ctgctgctat ttagtataag aacgttccac tctctggagg gtctaagtca 47040
gtgtatcaga cacattggtc aggaaatctg agtcaagttc tcttccattt caaccttatg 47100
tttttggtgg aggtaagagc ctgggcagag ttgaaataac aaataaatct caagagagtt 47160
tttttccctt ctgagaaaag ataatgcaat tataatacaa gatgaatctg ttgatttcaa 47220
ccaattctga gaattattaa acctgtgaaa tgacctgata aacaatgctt ttatggttac 47280
ataaaataat tacataaaat gttttacttt ccaaggagtt atatttattt tgcgaataag 47340
aagcccaagt gtgcttttat ttttgcttag taagaagatt ctcaatgatt tggcccatac 47400
taagaattat tattatcttt tttttttaga tggaatttcg ctcttgttgc ccaggctgga 47460
gtgcaatggc acgatcttgg ctcaccgcaa cctccgcctc ccaggttcaa gcgattctcc 47520
tgcctcagcc tcctgagtag ctggaattat aggcgcctgc caccgcgccc agctaatttt 47580

-continued

```
tgtattttag tagagacagg gtctcaccat gttggccagg ctggtcttga actcctgacc  47640
tcgggtgatc cacctgcctc agcctcccaa agtgctggga ttataggcat gagccacccc  47700
gcctgagcga attattatta tctttataat tagagtaatt ctctgtgttt taaattatat  47760
ttattattag agcttggtcc agagtcaact agaaatggaa aatcctcaag gtattataaa  47820
cttgtcattt aaaggtgcca gtaggatcac agtcacattc cataaaaaca cggctcagat  47880
gttacagaca tgtttttctc tcacattttt taacctggtt agagtaaatc cagtgcctta  47940
aagtttttaa taagtcaggt aattaaaaat aaaccactgg aagcctcaaa aagtttgtat  48000
caggaattgg gtgaataaaa tcttgtatat tttatgcaag aggagtaact ttgaaagaaa  48060
acacaccaaa atgccaatgg tggtaattgg tggtatctgg attggtgtga gtaggaatga  48120
ttattgtctc tctacttttt agatttttta taagaaggtt acagaacttt tactacaaat  48180
atgtataata aagtatccgt tccttagttc tgtcagcact ctaatcaata tcttcaaaca  48240
aaaaagccat ctgaaagaca gaaatggtgg cacgagacta tagttccagc tatttaggag  48300
gccgaggatc ccttgagctc aggagtttga gaccagcctt ggtaatatag tgagacccca  48360
tctctaaaaa aaaagaaaag gcatctgata tttcctgaag gctcctccag agcaatccag  48420
cagcagatac ctttgcaaac ttttgtaaag gaaataatta tcacttaatt tgtctaattt  48480
ttggatttag gttttaatta tcttttttga agggaatatg cagctatata ataagacact  48540
ttaaaaaagt ctctacttgt agagttatct ttccaaaata ctgatttgaa cattatttct  48600
ctacacgaca atcaatggcg actgccattt ctcttagcat ggcatgctag acttttgtga  48660
gttgttccta acagaatgtt ccagcctcat tgctcacatt tcccccaaac atacccaaag  48720
ctctaaatgt ctcagattac cttttttttt tttaaatgac atatttttta tttctttaag  48780
tgattttttt cactgtggta aaatacatat aacatcgcct ttaccaccct aaccattttt  48840
tttttttttt ttaattgatc attcttgggt gtttctcgca gaggggtatt tggcagggtc  48900
ataggacaac agtggaggga aggtcagcag acaaacaagt gaacaaaggt ctctggtttt  48960
cctaggcaga ggaccctgcg gccttccgca gtgtttgtgt ccctgggtac ttgagattag  49020
ggagtggtga tgactcttaa cgagcatgct gccttcaagc atctgtttaa caaagcacat  49080
cttgcaccgc ccttaatcca tttaaccctg agtggacaca gcacatgttt cagagggcac  49140
agggttgggg gtaaggtcac agatcaannn nnnnnnnnnn nnnnnnnnnn nnnnnnnnnn  49200
nnnnnnnnnn nnnnnnnnnn nnnnnnnnnn nnnnnnnnnn nnnnnnnnnn nnnnnnnnnn  49260
nnnnnnnnnn nnnnnnnnnn nnnnnnnnnn nnnnnnnnnn nnnnnnnnnn nnnnnnnnnn  49320
nnnnnnnnnn nnnnnnnnnn nnnnnnnnnn nnnnnnnnnn nnnnnnnnnn nnnnnnnnnn  49380
nnnnnnnnnn nnnnnnnnnn nnnnnnnnnn nnnnnnnnnn nnnnnnnnnn nnnnnnnnnn  49440
nnnnnnnnnn nnnnnnnnnn nnnnnnnnnn nnnnnnnnnn nnnnnnnnnn nnnnnnnnnn  49500
nnnnnnnnnn nnnnnnnnnn nnnnnnnnnn nnnnnnnnnn nnnnnnnnnn nnnnnnnnnn  49560
nnnnnnnnnn nnnnnnnnnn nnnnnnnnnn nnnnnnnnnn nnnnnnnnnn nnnnnnnnnn  49620
nnnnnnnnnn nnnnnnnnnn nnnnnnnnnn nnnnnnnnnn nnnnnnnnnn nnnnnnnnnn  49680
nnnnnnnnnn nnnnnnnnnn nnnnnnnnnn nnnnnnnnnn nnnnnnnnnn nnnnnnnnnn  49740
nnnnnnnnnn nnnnnnnnnn nnnnnnnnnn nnnnnnnnnn nnnnnnnnnn nnnnnnnnnn  49800
nnnnnnnnnn nnnnnnnnnn nnnnnnnnnn nnnnnnnnnn nnnnnnnnnn nnnnnnnnnn  49860
nnnnnnnnnn nnnnnnnnnn nnnnnnnnnn nnnnnnnnnn nnnnnnnnnn nnnnnnnnnn  49920
```

-continued

```
nnnnnnnnnn nnnnnnnnnn nnnnnnnnnn nnnnnnnnnn nnnnnnnnnn nnnnnnnnnn  49980
nnnnnnnnnn nnnnnnnnnn nnnnnnnnnn nnnnnnnnnn nnnnnnnnnn nnnnnnnnnn  50040
nnnnnnnnnn nnnnnnnnnn nnnnnnnnnn nnnnnnnnnn nnnnnnnnnn nnnnnnnnnn  50100
nnnnnnnnnn nnnnnnnnnn nnnnnnnnnn nnnnnnnnnn nnnnnnnnnn nnnnnnnnnn  50160
nnnnnnnnnn nnnnnnnnnn nnnnnnnnnn nnnnnnnnnn nnnnnnnnnn nnnnnnnnnn  50220
nnnnnnnnnn nnnnnnnnnn nnnnnnnnnn nnnnnnnnnn nnnnnnnnnn nnnnnnnnnn  50280
nnnnnnnnnn nnnnnnnnnn nnnnnnnnnn nnnnnnnnnn nnnnnnnnnn nnnnnnnnnn  50340
nnnnnnnnnn nnnnnnnnnn nnnnnnnnnn nnnnnnnnnn nnnnnnnnnn nnnnnnnnnn  50400
nnnnnnnnnn nnnnnnnnnn nnnnnnnnnn nnnnnnnnnn nnnnnnnnnn nnnnnnnnnn  50460
nnnnnnnnnn nnnnnnnnnn nnnnnnnnnn nnnnnnnnnn ntacgaaaac cagtcaggcg  50520
tggcggtgcg cccctgcaat cgcaggcact cggcaggctg aggcaggaga atcaggcagg  50580
gaagttgcag tgagccgaga tggcagcagt acagtccagc ttcggctcgg catcagaggg  50640
agaccgtgga aagaggggag agggagaggg agagggagag ggagagggat cagattactt  50700
tttaaagccc tacttattta aaaagacatc ttcctttttaa cctccaggct tttgtaaaat  50760
gcttatttct ctactgaaat atcccttccc tctcttctct tcttgcagaa cacatctatc  50820
agacctcctg gtgaagtttc tagcacagct tttttctctt tctcccttag aattaataac  50880
tgcctcatct gtatttccac agcatttcca agtacttcat acaccagcct gtgtcagttt  50940
gaagcattat tagctatttg ccctgcaaac ttgggaaggg tttttctgcc ttgcagtagt  51000
atgaagtctg aaatcaggac tatgacttat ctatcttact tatatttgtg aagttggttg  51060
tctgatttgc ttggatagtc tggtcatctc aattgtacaa taagtgctcc attactttac  51120
tttccttaaa atacaacgat ctcagattcc aaccccaatc tactccagtg ggtgggacat  51180
tcaaccttag tgtgctgtca agctctccag ggtcatgtca tctgaaaggc cctcttggcc  51240
ctgtgaagac tgattaactg tgtagccatg gagtctggga tcttgaggca ggaactctag  51300
gctggtgtgc agtctcttgc tcactactcc aatgtactgc cacagattag gacttgagtc  51360
cgccatctct ttaaaaaaaa aaacagtttt attgagatat aattgatcat aataaaccac  51420
acatatttaa tgtatatact ttataaaatt tggcaggcac acccatgaaa cccatcacca  51480
caatcaatat agtgaacata tccatcacct gcaaaagttt gttgcgccct tttgtaaact  51540
cctctctctt attctcccta cctctcctcc catctcatcc ccatgcaatc acggatctgc  51600
tttctgtcgc tgtaggttgg tttgaatttt ctagatttgt ttggattaca taaatggagt  51660
cgtgctgtat gtgctctttt ttctggctac tttcattcac ataataatgt tgagatttat  51720
ctatgttgca catattaata gttcattatt attctttatt gctgagtata ttctattgta  51780
tgaatgtatc aaaatttatt gatccattca ctgtagatgg atatttgggt tgtctccagc  51840
ttttggctat tataaataaa gctgctagga acattcatat acaaatcttt tttttttttt  51900
ttgagacaag tttcgccctt gttgcccagg ctggagtgca atggcacaat ctcagttcac  51960
cacaacctct gcctgctgga ttcaagtgat tcttctgcct cagcctccca agtagctggg  52020
attacaggca tgcgccacca cgcctgacta attttgtatt tttaatagag acagggtttc  52080
accatgttgg tcaggctggt ctcgaactcc cgacctgagg tgatccaccc acctcagcct  52140
cccaaagtgc tgggattaca ggtgtgagcc actgtgcctg gctatcatgt acaaatcttt  52200
atgtggtcat gtgcttcttt tctttctttt gggtaaatac attggactgg gatggatgga  52260
tcatatagta ggtgtatatt taactttcag agaactacca aatggtgttc cagaatggtc  52320
```

-continued

```
gcactgtgtt acactcccct tgacattgta tgagtgtttc agttctctct gtgcagctct  52380
ctcctctttg ggtctttgtc tttcagactc tagcacctta ataccccca agccttgtct  52440
tatcaactca gggagttggc cacactcatc ttcggtttcc atccctgcac ctcttcagtt  52500
ccccatcccc gcaccatggc ttgcaaactc tctcaagaca ggaggctggg gcagttgcag  52560
ggcttgtctc attggttttc tgtttcttag ggattactgt ctttcattgc tggatgtcta  52620
atgtattaaa aaccatttat ctattatatg tttgatttgg ctctttggtt gtttcaggtg  52680
cggaattaaa tctggtttct gatactctgt cttggctgaa agcatacgtt ttcagtgccc  52740
actgctggag aggggtggag ggcactcaag agttccattt ggacattgag ttagagaagt  52800
tgtgagagtt tacatacctg ctctggagcc tttaccccac tgttccctct gcatggaaaa  52860
tgctctcccc agactggcat atgccaaggt ccaatatcat tccagggctt aaattgattg  52920
ccagataagc tttgcctgta ttactctcac tccctactca ttttctgtcc tgttatccta  52980
ttttgttccc ttgatagcac ttaacacttt ctgaaattat gtcattcgtt aactcattta  53040
ttacctatcc tactccagta aaatgtaatt ttcgtgtcag cagggacctt tctggtcatg  53100
tccactgtgc taacccattt tgagggtttc tggcccctgg ggagtgctca gtgtgaattt  53160
gtggagtgaa tattaagatg aagataatgc taagtaggca gttggatatg tgagtctgga  53220
gctcagagga gaggaaaagt gaagcctgaa gatacacatt taagagtctc tgcttaacag  53280
tggcatttaa atccatagga atgaatgaaa ccccttgtat tagggaatag aagagcagat  53340
ggcccaagat aggatgctaa gaaacctccg aatatggagt tcacatctca gttgtgcctt  53400
tgaaattctt gtcatccact tttagttttc ttctcttcct acttgaaatt gcctaccaat  53460
tttcagagcc ctctccttcc tttataccgt catgagttgc gcactttgct tattttcctg  53520
attaagatca taagcctctt aagggaaaga tcctgtagtc aaaattacat tcttgaattg  53580
aattgggttg gactggagtg gactggagtg ataagtattg tcacattata gaattccacc  53640
cactgaagtg caagtgttaa atgtattaat atttcaagtt aatggatact ctgcccaagt  53700
ttttagttaa ttattattaa ctttccatta taaaagcttg tttttgttat taaatcaatc  53760
atcagattta acgcagaaat caactcatgt aaacatacag tgagagaatt gtatttttct  53820
ctaaattttc aggacattga aaaagacttg aaacaaatga ggcttcagaa cacaaaggaa  53880
agtaaaaatc cagaacagaa atataaagct aaggtaagaa atacttttgt ctttgggttc  53940
catattaaat agctggctgg ggagccacct tgtgatctcg gttgcctgca tgattttccc  54000
cctagtattt tatagaattg ctctattttg tgatatgaga ccaatggttt taagaatcta  54060
taatgtcaaa caaaattgac ctagggagtt gtaattttaa ggcttttact gaattgctaa  54120
actttttttt tttttttgct ttctcctaga agggggtaaa atttgaaatt aatttagaca  54180
aatgtatttc tgatgaaaac atcctccaag aggaagaggt atgccattaa gtctaaattt  54240
ccattagtag gtatcagaaa atgcatatat cttaatagca tgtttcatga aattatttca  54300
caggctgtag ggataatttt tttcaacttt tattttagat tcaggtggta catgtgcagg  54360
tttgttacct ggatatgttg tgtgatgttg aggtttggga tatgaatgat cccgtcaccc  54420
aggtattgag cataataccc agtagttagt ttttcaagcc ttgcttccct cctttcttac  54480
ccccactgta gtagctccca gtatctattg ttgctatctt tatgtccatg agtacccaat  54540
gtttagctcc cacttataag tgagaacatg cagaatttgg ttttctatcc ctatgtaatt  54600
ggttttctat ccctatgtaa tttgcttagg atagtagcct ccagctgcat ccatgttgca  54660
```

-continued

```
tggacatgat ttcattcttt tttatggctg catagtatcc catggtgtat atgtaccaca  54720
ttttctttat ccagaccacc actgatgggc acctaggttg attccatgac tttgctattg  54780
tgaatagtgc tgggatgaac atgtgagtat atgtgtcttt ttggtagaat ggtttgtttt  54840
cttttggata tatacccagt aatgggattg ctgggttgaa cagtagttct aagttctttg  54900
agaaatatcc aaactgcttt ctacagtggt tgaactaatt tacattacat ttccgccaac  54960
actacataag cattcccttt tctctgcagc ctcgccaata tttgtttttt gacttttttag 55020
taatagccat tctgactcgt gtgagatggt gtctcattgt ggttttgatt tgtagttctc  55080
tgataattag tgatgatgag tattctttta tatatttgtt ggctgcttgt atgtcttctt  55140
ttgagaagtg tctctttcta tcttttgtcc actttaaaat ttgggttgtt ttttcttgtt  55200
cagttaagtt ccttatagag tctggatatt agacctttgt tggatgcata gtttgcaaat  55260
attttcttct attctgtagg ttgtctattt actctgttga tagtttcttt tgctgtgcag  55320
aagctcctta gtttaattag gttccacttg tcaattttgt ttttgttgca attgcttttg  55380
aggacttaat cacaaattct ttcccaaggc ccatgttcat aatggtgttt cctaggtttt  55440
cttttaggat tcttatagtt taaggtctta cttttaaatt gttaagtcat ctttagctga  55500
tttttgtata cagtgaaagg taggggtcca gtttcattct tctgcatgta gctaaccagc  55560
tatcccagca ccacttattg gataggaagt cctttcccca ttgcttattt ttgtcgattt  55620
tgtcaaagat tatatggctg tagatgagtg gctttatttc tgggttctct attctgttcc  55680
ttggtttatg tgtttgtttt tgaaccagta ccatacagtt ttgattactg tagtcttatg  55740
gtatagtttg aagttgggta atgtgacgac tctggcgttg ttctttttgc ttagaattac  55800
tttggctatt tgggctcttt tttgtttaca tatgaatttt agaatagttt tttttttctc  55860
caatcctgtg aaaagttaca ttggtagttt gacaggaata gtgttgaatc tatagattac  55920
tttgggcagt atggccattt taatgatatt gattattcca atccatgcat gtggcatgtt  55980
tttccatttg tttatgtcat gtatgatttc tttctgtgtt gtgtagctct tcttgtagag  56040
atctttcacc tccttggtta gatgtactcc taggtatttt attttatttt ttggtggcta  56100
ttgtaaatgg gattacgttc ttgatttggc tctctgcttg aatgttattg gtgtatagga  56160
atcctattga ttattgtact tcgatattgt atcctgaaac tttgctgaag ttgttcatca  56220
gttccaggaa cctttgggtc gagtctttgg gttttcaacc tatagtatca taagcgtgaa  56280
gagatggttt gacttcttct tttcttattt ggatgcctag aattttagaa aatatttcta  56340
gaaaaatgtt tggtgctcaa ggccagggaa cggtggctca cagctgtaat cccagcactt  56400
tgggaggctg agacgggcag atcatgagat caggagattg agaccatcct ggctaacatg  56460
gtgaaacccc atctctacta aaaatacaaa aaattagctg ggtgtggtgt cacccacctg  56520
tagtctcagc tacttaggag gctgaggcag gagaatcact tgaacccagg aggcagaggt  56580
tgcagtgagc tgagatcgct gtactgcact cgagcctggg caacagagtg agacactgtc  56640
tcaaaaaaaa aaaaagggaa agaaaaatgt ttggtgttca aatgagtcct ccaaatactt  56700
tttattctcc cattttattt tattggtgtt atttctttag ataaattatt acattttaat  56760
ttacttttct ttaaataaaa gagctatttt actcataata ttaattttta tcatagccaa  56820
attaaaatag aagacctgat acattgtcaa caactaatat actgacctaa aaaattgaac  56880
aggtaccctg aaaccaggca catttatttt aggtcttaat tagttattga taactttaag  56940
taaatctcat ttatgcattt gggctctcct tgccacagca aggagtaaat acagtaaatc  57000
caatacagta aatccaaatt tcattttatt agttgatttc aaaatctttt tttatcctgg  57060
```

-continued

```
ttttatcaga cctataacaa atgtcaaaat taattggttt atttttccat tttacctttt  57120
ctgaattcac cttttaagtc aatataagta tgaataatta tacctgatgc tcagttttta  57180
tttaatgttc tttattagct taaaacattt tcatgttagc atttcttatt tttatgagca  57240
tttgctacat aaagacttca ttagagtggt gatagttagc attcacctct gttcaaccat  57300
aaattcctaa atgccccaga ggtgagacat cagagtggag cagatctggg gacctgcttc  57360
tgagtgggaa cttgagaagt ggtactctca cagagcttct gtgaagtgag gtgctgacgt  57420
tgccctgctg aaatgaaaga atggagtcca aaaagtttta actgccactc tttcttattc  57480
tttgctttga tctgcgtgaa acagaagtgt tcattttggt attgactaca aaatactagg  57540
agcagattta gggagctggt taagaatgtt gtacacttaa aacagggcat gaatgagaaa  57600
agcttgagag cactgtagaa tggagctgaa gtggaatact attgaagtca gaaagtctag  57660
ataaaattaa gttgccttat gaccagtgct tgacactgtt aacatggaga agaaatgaaa  57720
acatttctgt ttttatctaa catagctcta gttttaaaac tctatggatt tatttgttta  57780
gtaaacattt gttgaatatt tactatatac cttgctaatt aattttacta ggaacacgaa  57840
aatatggttt ttctttcttt caaaatatgg ctaatttatc atgaaacact gtggaattga  57900
tttaggcaat ggatatacca aatgaaactt tgacctttga ggatggcatg aagtttaagg  57960
aatatgaatg tgtaaaggag catggagatt atacagacaa agcatttgaa aaacttcact  58020
gcccagaagc aggtatgtgt ttcttgaaag ttgtaaatga gaaggaactg ttttattagc  58080
aacccatttt gaactctgtc cccatgcatc tgcctcggct ccactgttac ttgacccctt  58140
tctgccctct ctaagcaagg cagaaacaca cttattattc tcctgccacc catgcagtgg  58200
ccacactccc tgagatccag ccctcctctc ctgctccata cccactccct cttgcagctt  58260
tggcttctcc caggagctcc agacttacca gtctttctca ttgtcttctg ggaagctcca  58320
tggacaagtg ttgccagtat ctgaaactca gctgtgtaaa gtcaagctct tctgtgctct  58380
tcccagtgac cctttatttt ggttagtgtc acagatgcaa ctggctgggg ccagtgttgt  58440
gggcagtaaa agaatttatc aacacaattg taagtaaaga aaggcagatt tattaaagta  58500
cagagatacg ttgcaagagt gcaatgggca gcacagcaga gaagaggctg tctgctaaga  58560
ggcaggggct agagggaagt tttatagggt catattggag gagctacatg ctgataaggt  58620
gtgcagataa ggttttgctg cttgggctac atgtggaagg aatgaggtat ttgggaacag  58680
gatgtgacag cagcttgtct gtgatgagtc atctctcaga acagttgttc ccccatcccc  58740
acccccaacc tgggacccct ccctttttgt tgtttactta tcttatgaga acttcacagt  58800
cagtgctgtc accagggtgc acccttagca tagtgtctat tctgagatgt ctctggagtc  58860
ttcctcttcc ttcattctct ctgttactgg tttagggctc tgtcatctct cagtagtgtg  58920
gtgtaggctt cagagacaga tgggaattga atctcagctg ttgctgccac cttctggtta  58980
tgtgaccttt ctttcacaag ttattccaac actgaatctc agtttcacct taggaacagg  59040
ggataatagt agtaggaata accacacagg gtaattgtga ggaccaaagt gagttttgat  59100
gtataaacga cctggcacat actaggtgcc taaattaagt gctgtctttt cattttccct  59160
tttccttccc cttgctgtat tgccttattt gcttatgtga ccttctttct ctagtatttc  59220
cccttcattc tctaaatggt tactgtatta gtccattttc ttgctgctga taaagacata  59280
cctgagactg agcaatttac aaaagaaaga ggtttaattg gacttacagt tccacatggc  59340
tggggaagcc tcacaatcat ggtggaaggc aaggaaaagc aagtcacatt ttacatggat  59400
```

-continued

```
ggcagcaggc aaagagaaag aacttgtgca gaggaactcc tctttttaaa accatcttat  59460
ctcgtgagac tcattcacca tcacgagaac agcatgggaa agatccgccc ccatgattca  59520
accacctccc tctgggtcac cccacaacac acaggaattc aagatgagat ttgggtggga  59580
cacagccaaa cgatatcagt tactaaagtt atcttggcat attattactc tgctcagatt  59640
ttttttttgg ataatacctg cagaataagg tccattccac atattatcac atttaacact  59700
acatggccta attctgctgt gacccacttt tctcatccca gcatggcctc tttccttcca  59760
tggaaaatgg gatccataca gcctgctgga atgcccattt tctcctacag ctggaatgcc  59820
cattttctcc tacagcattt acagaactga cttggctcag tttcctcttc ctggaatact  59880
ctctgcctca tttccttctg gaaaaatctc cattcagcag gcatcttatt gaggatctcc  59940
tttgtgccaa agactgctca ctggtaggga gctcaaagat gaatgaaatc tgggccctgt  60000
tctcaatatc acagaagtgt tatgagcaaa aaagtcacaa aacatgtttt ctgagcctga  60060
aatgttaatc actgtttgaa gtgcgagctg ggtggagagt cagggaggtc cgcactcctc  60120
cagggcttca catgccatca tttttgtgat tgagaaggat catgctggct gcagagcaaa  60180
ggatggcatg gagggcaaga ctgaaggcag gagaagagtc caagtgcatg agccagagtg  60240
gtgcagggag aatagatact gagtgtggga actgaggaag agaaggggct caaggatatt  60300
cccagttttc taattcaaat gcatgaagct ttcatcaacc aaaaatacat cacatggagg  60360
gtaatggggt cgggagagac aaggtagtga tctaaatttg gaacatgttg agatttaggt  60420
ctatagagca tcagttgcag attctatata agactgaagg cctggggcat atcagggata  60480
aagatatagc ttggtggccc ttagcatatc cgtggttttt aactttggtg atggtcaaaa  60540
tacctatgca gaaggactgg agtgagaagg aaatggagct taggacataa ccctaccact  60600
atataaacaa actttggaga atcaggagag agtaaagcca aaggaggaga gacaggtcat  60660
ggaggaggca caggaattgg cagcatcaac tggaagagaa aggccagatg aggtgagtgg  60720
gatttggccc ttcaggagcc gttaatggcc tcagggaaag cagtcaactg tgtaaggggt  60780
aaattcaatg gttatctttg catcagtttg ctgggaaaag cagagggggt tggctgtttt  60840
ttagatgaaa gaaaaaaaaa ccttcatcag tagtatactg aaaattgtct ctcattttaa  60900
tctgtattcc tgtaattatt atttaggctg aaggattttt ccgtatgttt gttgaccatt  60960
catatttctc cttttttttt cttttttctt tttttgtttt ttttttgaga gggagtctcc  61020
ctctgtcgcc caggctggag tgcagtggca caatcttggc tcactgtaac ctccgcctcc  61080
tgggttcaag cgattctcct gcctcagcct ccctgagtag ctggcatagg tgcgcgccac  61140
cacgcctagc tgatttttaa aatattttta gtagagatga ggtttcacca tgtttgccag  61200
gctggtattt gaactcttga tctcaggtga tctgcccacc ttggcctccc aaagtgctgg  61260
gattacaggc atgagccacc acgcctggcc aacccttcat atttctgtta tgaattatgt  61320
actcatgccc ttcatccttt tttctactga aaatggcatg tttgtttttt tctttataag  61380
actgatttaa atcaaacctt tgcctgtaat atgtattgca aatgttttcc tcagttggtt  61440
gtcagatctc atttatagta ataacagcaa atatatatga gtgtgtgtgt gtgtgtgtgt  61500
gtgtgtgtgt gtgtatttgt gtattcatcc acttaggaat aaattttatg agaattgtgc  61560
ggcatataga aagaaaactg taaaacctta ctgaggtatt tacagaccac ttgaataaat  61620
ggagagaaat aacggtgcta tatattggaa atattttttc caaataaata ttgcagtatc  61680
gttgtctgag gtattaccca gaactctttg tctcacgacc aaaagaataa ggagggtgga  61740
cagtaagggt gagtttggac cgaaaattta ataaacaaaa gaggaaagct cttcactgtg  61800
```

-continued

```
gagaggggac ccaagagggt tgccatttca cagctgagta caaaggcttt tatgaggaac  61860
ctgatagggc tgggggtttc atttgcataa ggcatgaatt tctggcagct ccaccctgtt  61920
ctcctagtat gctgactggc taggggttgt ttttggaaaa ggcaccactc agaaaatgac  61980
atgatggttg accaggcatg gtagttcatg cctgtaatcc cagcactttg ggaggctgag  62040
gtgggcagat ctctcaaggc caggagttcg agactagcct ggccaatatg gctaaagccc  62100
atctctacta aaaatacaaa aattagccag gtgtggtggt gcacacctgt aatctcagct  62160
acttgggagg ctgagccaca agaatcactt ggacctggga ggtgaaggtt gcagtgagac  62220
gagattgtgc caccacactc cagtcacact ccagctgggt gacagagcaa gcaagactcc  62280
atctcaaaaa aaaaaaaaaa aaaaatgacg tggtgtaaag accagttgga gccttggccc  62340
acaaccagct gagtgttgga gtgatggttc acagaggctt ggctcacagt ccaaagtatg  62400
ccccaaaaag gaaaggaatg tgctcactgg ggcccaccat gtacatgccc acaaaaggag  62460
aaggaactat ttgctagagg cccactgatt gcacaaagaa caaaggcatt tctgtgttgg  62520
actttgctcc cttatctgtg cagctgtggg catgttttag gcaagcttcc tgtgctagtt  62580
cccttatctg tgtctgcagc ttgatttttc agactgttct tttgtttgaa agaattctga  62640
ggacctgccc taactgcctg cctaactgat tctttctttc tcctccctca atatgtggat  62700
ttatggctat ttcaatcaaa accacagtag gatttttttt ttaatggtat agggagatct  62760
tggcaggttg gagaatcctg gagcttctta agtggccaaa aattttgaaa aagaagaaca  62820
gtgaagtggt acttacattt ccaaatgtca aaatatatta cagaaattat agtcattcac  62880
acaatatgat agtagcaccc aaatagttaa aacagtgaga agagaaagtt agaaacagat  62940
cctagtatgt atcataattc agcacaaatg aaaagtaaca tcacaagtca gcgtgaaaag  63000
aaaggattat tcagataaat gctgctgggc caattggtta acagtttggg gaagattgtg  63060
aaatcagacc ctatataata tgatacaaca aaataaattt tttaaaaaag agttatatgt  63120
aaaaagttat acattagaaa atgaaataaa agaacatagg tcattttttt ttttttttga  63180
gacagcgtct cactctgtca ccaaggctgg agtgcaaagg cgtgatctcg gctcactgca  63240
aactccgcct tctgggttca agcgattctc ctgcctcagc ctcccgagta gctgggacta  63300
caggcacccg ctaccacgcc cagctaattt ttatattttt gatagagacg gggtttcacc  63360
atgttggcca ggatggtttc gatctcttga ccttgtgatc cgcccgcctc ggcctcccaa  63420
agtgctgaga ttacaggcgt gagccactgc acccggccga gttaattttt tttgaacagg  63480
gaagagctat ctgttcaaaa tacatagaaa aaaaaaccac agaataaatt agtaataatt  63540
caactttaac aacaaaaagc tgtaataaag caaatcatac taacccct               63588
```

<210> SEQ ID NO 4
<211> LENGTH: 616
<212> TYPE: PRT
<213> ORGANISM: Mouse

<400> SEQUENCE: 4

```
Met Glu Lys Tyr Val Arg Leu Gln Lys Ile Gly Glu Gly Ser Phe Gly
 1               5                  10                  15

Lys Ala Val Leu Val Lys Ser Thr Glu Asp Gly Arg His Tyr Val Ile
            20                  25                  30

Lys Glu Ile Asn Ile Ser Arg Met Ser Asp Lys Glu Arg Gln Glu Ser
        35                  40                  45

Arg Arg Glu Val Ala Val Leu Ala Asn Met Lys His Pro Asn Ile Val
```

-continued

```
    50                  55                  60

Gln Tyr Lys Glu Ser Phe Glu Glu Asn Gly Ser Leu Tyr Ile Val Met
65                  70                  75                  80

Asp Tyr Cys Glu Gly Gly Asp Leu Phe Lys Arg Ile Asn Ala Gln Lys
                85                  90                  95

Gly Ala Leu Phe Gln Glu Asp Gln Ile Leu Asp Trp Phe Val Gln Ile
            100                 105                 110

Cys Leu Ala Leu Lys His Val His Asp Arg Lys Ile Leu His Arg Asp
        115                 120                 125

Ile Lys Ser Gln Asn Ile Phe Leu Thr Lys Asp Gly Thr Val Gln Leu
    130                 135                 140

Gly Asp Phe Gly Ile Ala Arg Val Leu Asn Ser Thr Val Glu Leu Ala
145                 150                 155                 160

Arg Thr Cys Ile Gly Thr Pro Tyr Tyr Leu Ser Pro Glu Ile Cys Glu
                165                 170                 175

Asn Lys Pro Tyr Asn Asn Lys Ser Asp Ile Trp Ala Leu Gly Cys Val
            180                 185                 190

Leu Tyr Glu Leu Cys Thr Leu Lys His Ala Phe Glu Ala Gly Asn Met
        195                 200                 205

Lys Asn Leu Val Leu Lys Ile Ile Ser Gly Ser Phe Pro Pro Val Ser
    210                 215                 220

Pro His Tyr Ser Tyr Asp Leu Arg Ser Leu Leu Ser Gln Leu Phe Lys
225                 230                 235                 240

Arg Asn Pro Arg Asp Arg Pro Ser Val Asn Ser Ile Leu Glu Lys Gly
                245                 250                 255

Phe Ile Ala Lys Arg Ile Glu Lys Phe Leu Ser Pro Gln Leu Ile Ala
            260                 265                 270

Glu Glu Phe Cys Leu Lys Thr Leu Ser Lys Phe Gly Pro Gln Pro Leu
        275                 280                 285

Pro Gly Lys Arg Pro Ala Ser Gly Gln Gly Val Ser Ser Phe Val Pro
    290                 295                 300

Ala Gln Lys Ile Thr Lys Pro Ala Ala Lys Tyr Gly Val Pro Leu Thr
305                 310                 315                 320

Tyr Lys Lys Tyr Gly Asp Lys Lys Leu Leu Glu Lys Lys Pro Pro Pro
                325                 330                 335

Lys His Lys Gln Ala His Gln Ile Pro Val Lys Lys Met Asn Ser Gly
            340                 345                 350

Glu Glu Arg Lys Lys Met Ser Glu Glu Ala Ala Lys Lys Arg Arg Leu
        355                 360                 365

Glu Phe Ile Glu Lys Glu Lys Lys Gln Lys Asp Gln Ile Arg Phe Leu
    370                 375                 380

Lys Ala Glu Gln Met Lys Arg Gln Glu Lys Gln Arg Leu Glu Arg Ile
385                 390                 395                 400

Asn Arg Ala Arg Glu Gln Gly Trp Arg Asn Val Leu Arg Ala Gly Gly
                405                 410                 415

Ser Gly Glu Val Lys Ala Ser Phe Phe Gly Ile Gly Gly Ala Val Ser
            420                 425                 430

Pro Ser Pro Cys Ser Pro Arg Gly Gln Tyr Glu His Tyr His Ala Ile
        435                 440                 445

Phe Asp Gln Met Gln Arg Leu Arg Ala Glu Asp Asn Glu Ala Arg Trp
    450                 455                 460

Lys Gly Gly Ile Tyr Gly Arg Trp Leu Pro Glu Arg Gln Lys Gly His
465                 470                 475                 480
```

-continued

| | | | | | | | | | | | | | | | |
|---|---|---|---|---|---|---|---|---|---|---|---|---|---|---|---|
| Leu | Ala | Val | Glu | Arg | Ala | Asn | Gln | Val | Glu | Glu | Phe | Leu | Gln | Arg | Lys |
| | | | | 485 | | | | | 490 | | | | | 495 | |
| Arg | Glu | Ala | Met | Gln | Asn | Lys | Ala | Arg | Ala | Glu | Gly | His | Val | Val | Tyr |
| | | | 500 | | | | | 505 | | | | | 510 | | |
| Leu | Ala | Arg | Leu | Arg | Gln | Ile | Arg | Leu | Gln | Asn | Phe | Asn | Glu | Arg | Gln |
| | | 515 | | | | | 520 | | | | | 525 | | | |
| Gln | Ile | Lys | Ala | Lys | Leu | Arg | Gly | Glu | Asn | Lys | Glu | Ala | Asp | Gly | Thr |
| | 530 | | | | | 535 | | | | | 540 | | | | |
| Lys | Gly | Gln | Glu | Ala | Thr | Glu | Glu | Thr | Asp | Met | Arg | Leu | Lys | Lys | Met |
| 545 | | | | | 550 | | | | | 555 | | | | | 560 |
| Glu | Ser | Leu | Lys | Ala | Gln | Thr | Asn | Ala | Arg | Ala | Ala | Val | Leu | Lys | Glu |
| | | | | 565 | | | | | 570 | | | | | 575 | |
| Gln | Leu | Glu | Arg | Lys | Arg | Lys | Glu | Ala | Tyr | Glu | Arg | Glu | Lys | Lys | Val |
| | | | 580 | | | | | 585 | | | | | 590 | | |
| Trp | Glu | Glu | His | Leu | Val | Ala | Arg | Val | Lys | Ser | Ser | Asp | Val | Pro | Leu |
| | | 595 | | | | | 600 | | | | | 605 | | | |
| Pro | Leu | Glu | Leu | Leu | Glu | Thr | Gly | | | | | | | | |
| | 610 | | | | | 615 | | | | | | | | | |